(12) United States Patent
Eul

(10) Patent No.: US 8,822,660 B2
(45) Date of Patent: Sep. 2, 2014

(54) CELL DEATH PRE-MRNA-ENCODING DNA

(75) Inventor: Joachim Eul, Berlin (DE)

(73) Assignee: Andreas Ney, Berlin (DE)

( * ) Notice: Subject to any disclaimer, the term of this patent is extended or adjusted under 35 U.S.C. 154(b) by 92 days.

(21) Appl. No.: 12/511,510

(22) Filed: Jul. 29, 2009

(65) Prior Publication Data

US 2010/0081198 A1 Apr. 1, 2010

Related U.S. Application Data

(60) Division of application No. 10/777,492, filed on Feb. 12, 2004, now abandoned, which is a continuation of application No. PCT/EP02/09082, filed on Aug. 13, 2002.

(30) Foreign Application Priority Data

Aug. 13, 2001 (DE) ................... 101 39 492

(51) Int. Cl.
*C07H 21/02* (2006.01)
*C12N 15/00* (2006.01)
*C12N 15/10* (2006.01)

(52) U.S. Cl.
CPC ............ *C12N 15/10* (2013.01); *C12N 15/1027* (2013.01); *C12N 15/102* (2013.01)
USPC ........................... 536/23.1; 435/440; 435/455

(58) Field of Classification Search
None
See application file for complete search history.

(56) References Cited

U.S. PATENT DOCUMENTS

| | | | | |
|---|---|---|---|---|
| 5,677,274 A | * | 10/1997 | Leppla et al. | 514/2 |
| 5,945,100 A | * | 8/1999 | Fick | 424/93.21 |
| 6,013,487 A | | 1/2000 | Mitchell | |
| 6,897,016 B1 | | 5/2005 | Sullenger et al. | |
| 2004/0167066 A1 | * | 8/2004 | Marzioch et al. | 514/12 |

FOREIGN PATENT DOCUMENTS

WO 02/053581 A2 7/2002

OTHER PUBLICATIONS

Wu et al., Adenovirus-expressed human hyperplasia suppressor gene induces apoptosis in cancer cells, 2008, Molecular Cancer Therapy, vol. 7, pp. 222-232.*
Wei et al., Tumor-suppressive functions of leucine zipper transcription factor-like 1, 2010, Cancer Research, vol. 70, pp. 2942-2950.*
Parihar et al., mAtNOS1 regulates mitochondrial functions and apoptosis of human neuroblastoma cells, 2008, Biochimica et Biophysica Acta, vol. 1780, pp. 921-926.*
Saeki et al., Gasdermin, suppressed frequently in gastric cancer, is a target of LMO1 in TGF-beta-dependent apoptotic signalling, 2007, Oncogene, vol. 26, pp. 6488-6498.*
"Thymidine Kinase Human Herpesvirus 1", GenBank No. BAA93078.1, Jul. 29, 2000, accessed and retrieved from www.ncbi.nlm.nih.gov on Aug. 26, 2013.*
"Thymidine Kinase Human Herpesvirus 1", GenBank No. BAA23729.2, May 8, 2001, accessed and retrieved from www.ncbi.nlm.nih.gov on Aug. 26, 2013.*
"Thymidine Kinase Human Herpesvirus 2", GenBank No. AAL73990.1, Feb. 20, 2002, accessed and retrieved from www.ncbi.nlm.nih.gov on Aug. 26, 2013.*
International Search Report for PCT/EP2002/009082 filed Aug. 13, 2002 published Jan. 29, 2004.
International Preliminary Examination Report for PCT/EP2002/009082 filed Aug. 13, 2002 published Mar. 17, 2004.
Joachim Eul et al., Experimental evidence for RNA trans-splicing in mammalian cells, The EMBO Journal, 1995, pp. 3226-3235, vol. 14, No. 13.
Richard Conrad et al., Insertion of Part of an Intron into the 5' Untranslated Region of a *Caenorhabditis elegans* Gene Converts It into a trans-Spliced Gene, Molecular and Cellular Biology, Apr. 1991, pp. 1921-1926, vol. 11, No. 4.
Concha Caudevilla et al., Localization of an exonic splicing enhancer responsible for mammalian natural trans-splicing, Nucleic Acids Research, 2001, pp. 3108-3115, vol. 29, No. 14.
J. Eul et al., Trans-splicing and alternative-tandem-cis-splicing: two ways by which mammalian cells generate a truncated SV40 T-antigen, Nucleic Acids Research, 1996, pp. 1653-1661, vol. 24, No. 8.
M. Puttaraju et al., Splicesome-mediated RNA trans-splicing as a tool for gene therapy, Mar. 1999, Nature Biotechnology, vol. 17, pp. 246-252.
J. L. Reyes et al., The canonical GU dinucleotide at the 5' splice site is recognized by p220 of the U5 snRNP within the splicesome, 1996, RNA, vol. 2, pp. 213-225.
James Bruzik et al., Enhancer-dependent interaction between 5' and 3' splice sites in trans, Jul. 1995, PNAS, vol. 92, pp. 7056-7059.

* cited by examiner

*Primary Examiner* — Dana Shin
(74) *Attorney, Agent, or Firm* — Fleit Gibbons Gutman Bongini & Bianco PL; Martin Fleit; Paul D. Bianco

(57) ABSTRACT

Methods and products for the repair of genetically defective DNA in the region of a mutated exon, for the specific destruction of tumor cells, and for the identification of naturally trans-spliced RNA. The methods inter alia are based on the utilization of cellular RNA splicing components.

10 Claims, 15 Drawing Sheets

FIG. 1A
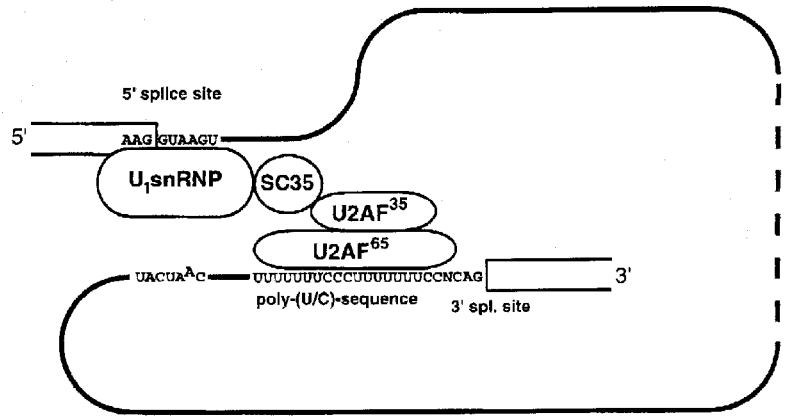
association between the 5' splice site and the 3' splice site in the E-complex
FIG. 1B
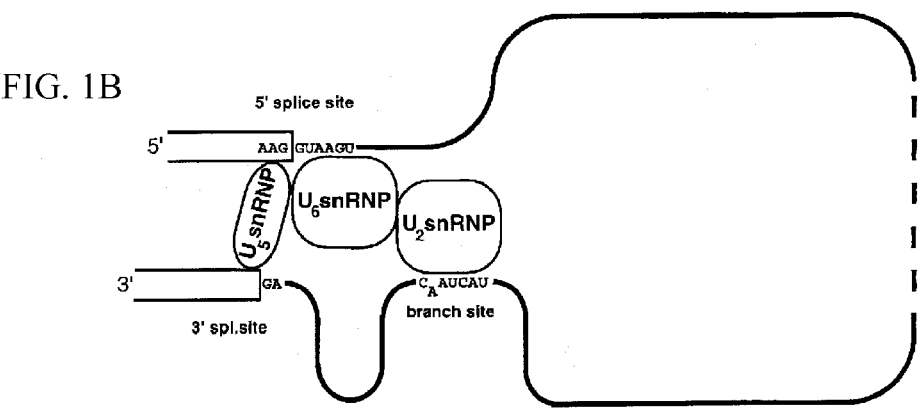
association between the 5' splice site and the 3' splice site in the B/C-complex
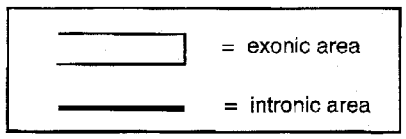
association between the 5' and 3' splice site at different points during splicing

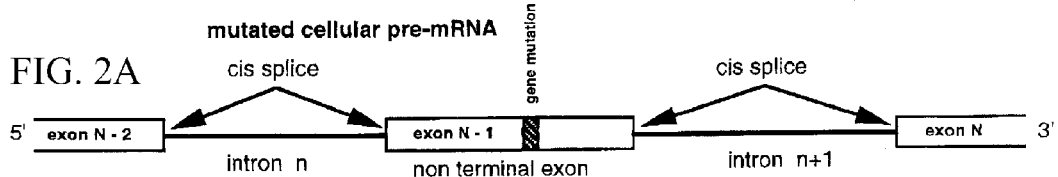
FIG. 2A
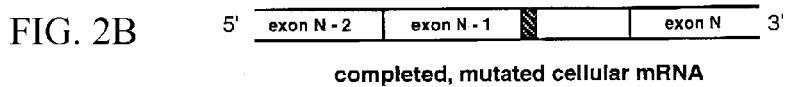
FIG. 2B
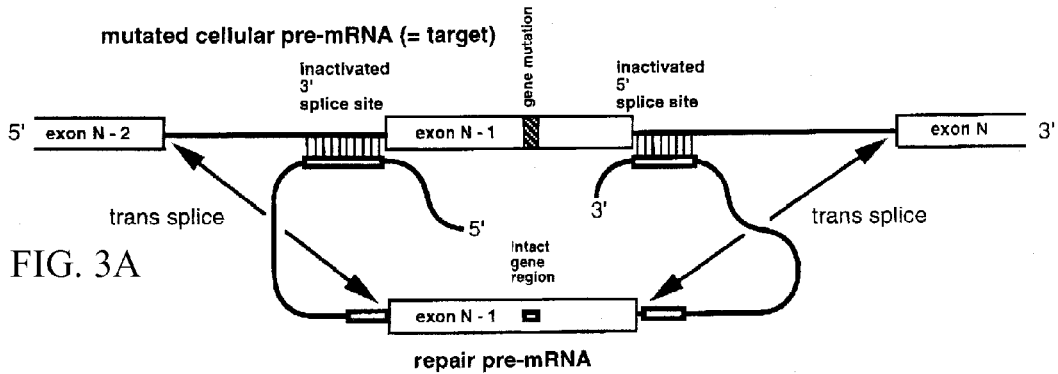
FIG. 3A
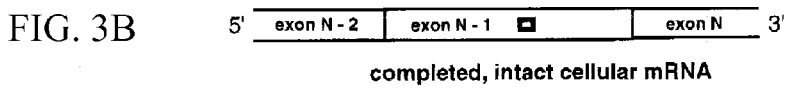
FIG. 3B
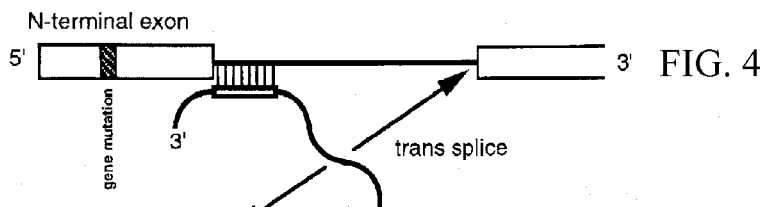
FIG. 4
FIG. 5
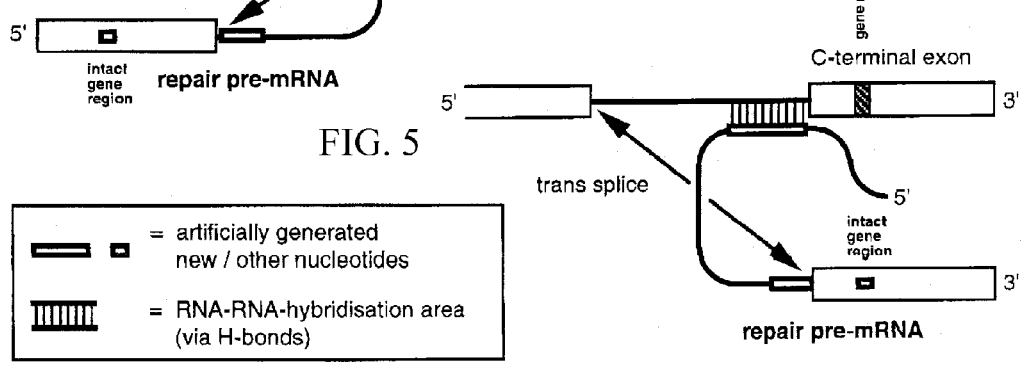
repair of internal, N- or C-terminal gene mutated exons by trans splicing

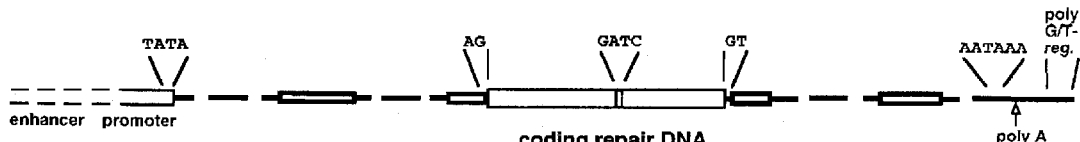
FIG. 6A coding repair DNA
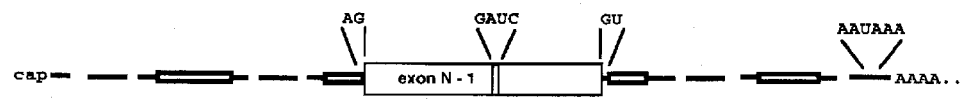
FIG. 6B repair pre-mRNA
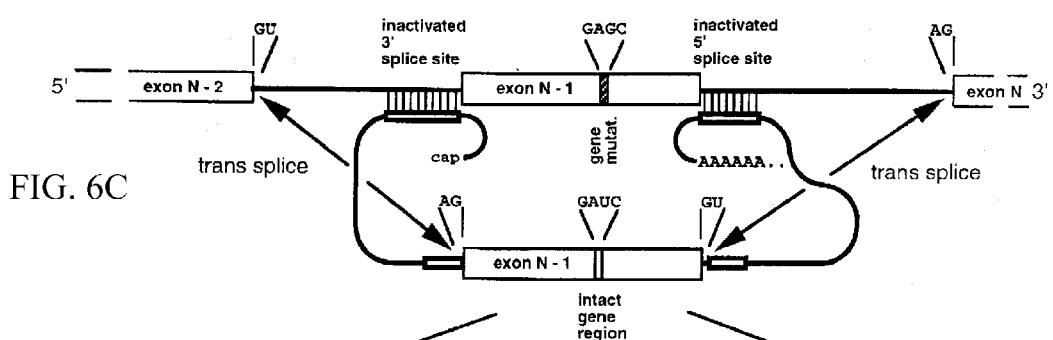
FIG. 6C
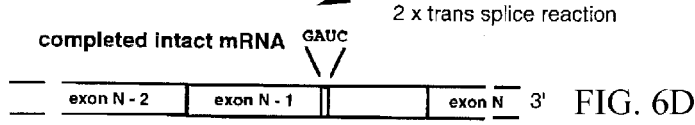
FIG. 6D
FIG. 6E
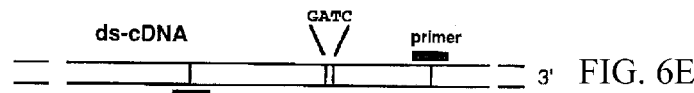
FIG. 6F completed, mutated mRNA
FIG. 6G
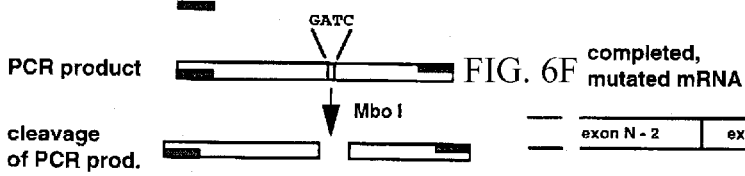
FIG. 6H
FIG. 6I
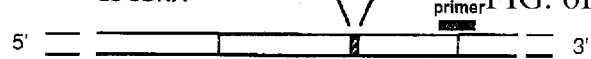
FIG. 6J
identification of repaired (intact) and not repaired (mutated) mRNA
no cleavage of PCR prod.
FIG. 6K

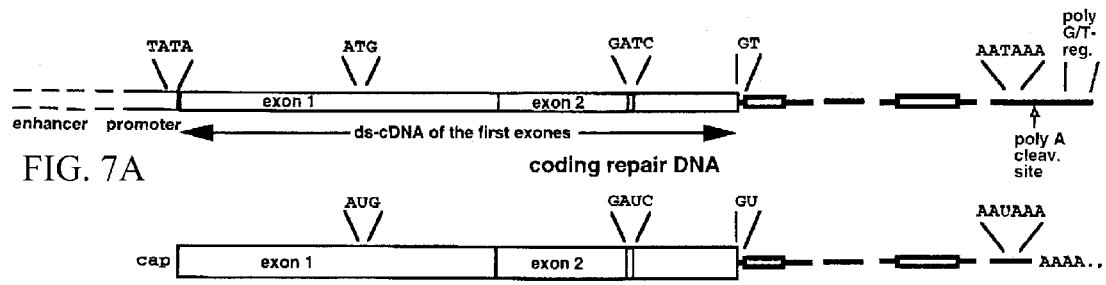
FIG. 7A
FIG. 7B repair pre-mRNA (with the first exons) and with a potent 5' splice site
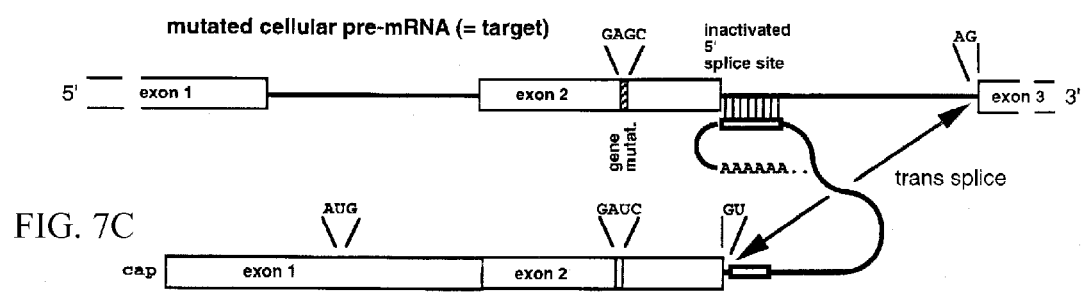
FIG. 7C
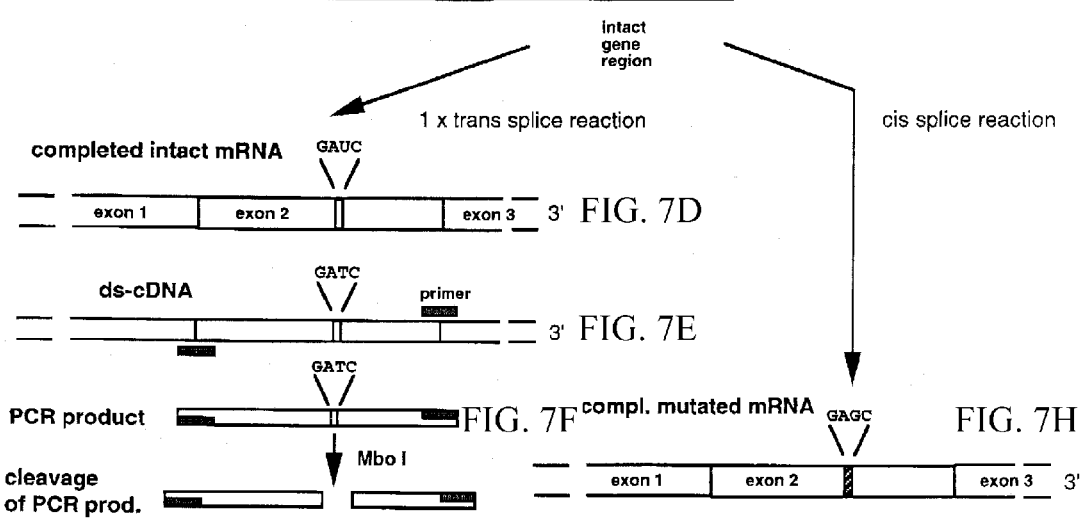
FIG. 7D
FIG. 7E
FIG. 7F
FIG. 7G
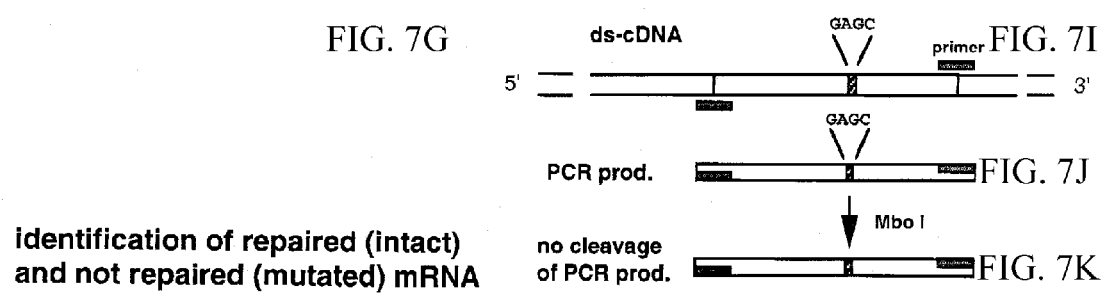
FIG. 7H
FIG. 7I
FIG. 7J
FIG. 7K
identification of repaired (intact) and not repaired (mutated) mRNA

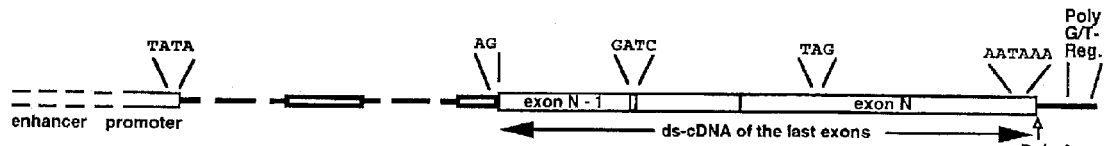
FIG. 8A  coding repair DNA
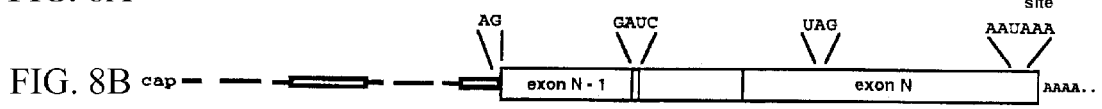
FIG. 8B
repair pre-mRNA (with the last exons) and with a potent 3' splice site
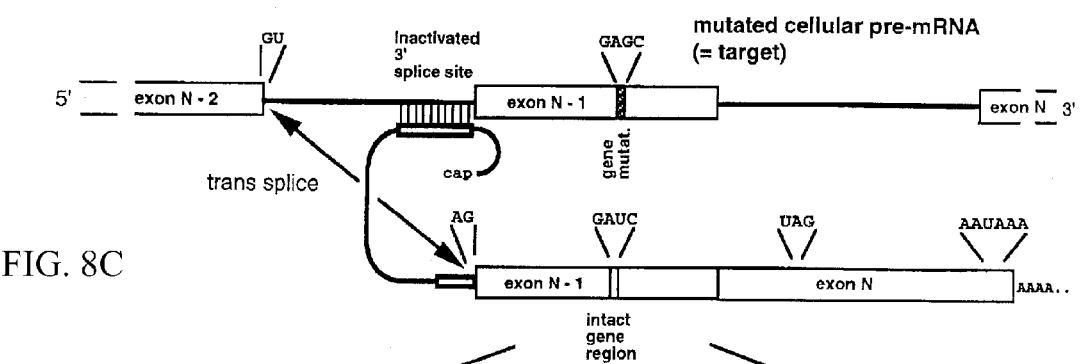
FIG. 8C
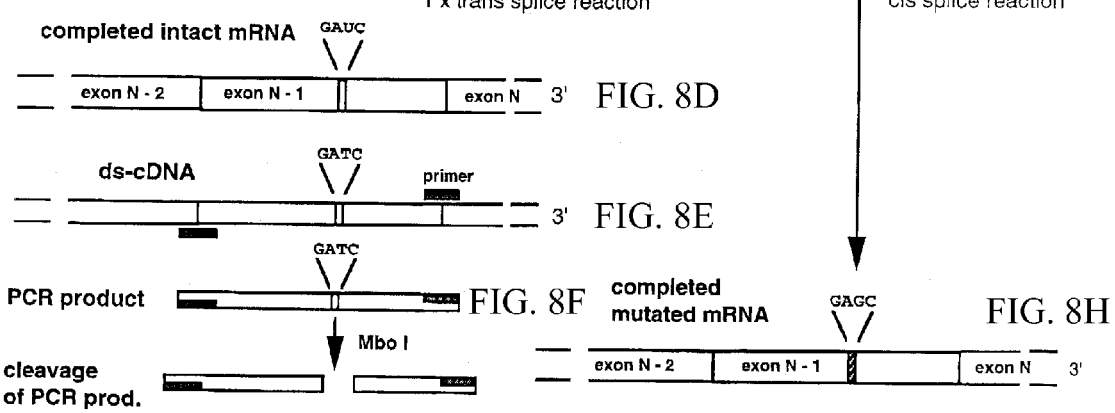
identification of repaired (intact) and not repaired (mutated) mRNA methods to prefer the use of a 5' splice site on a trans-splice RNA methodes to prefer the use of a 3' splice site on a trans-splice RNA

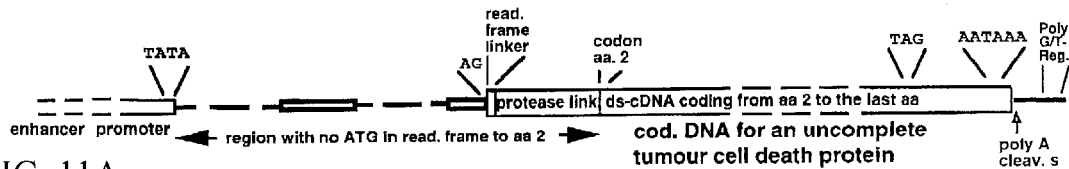
FIG. 11A
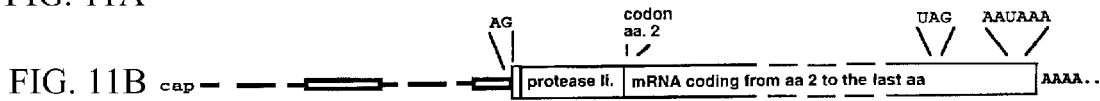
FIG. 11B
(yet) uncomplete tumour cell death pre-mRNA (with 2 linkers and codons for aminoacid (aa) 2 an the follow. aa and with a potent 3' splice site)
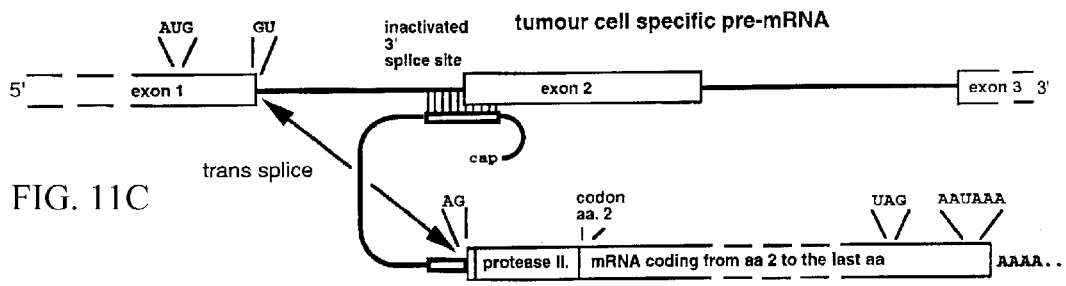
FIG. 11C
FIG. 11D
completed (active) hybrid mRNA with AUG start codon
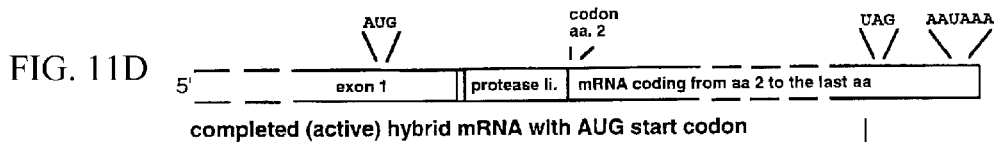
FIG. 11E
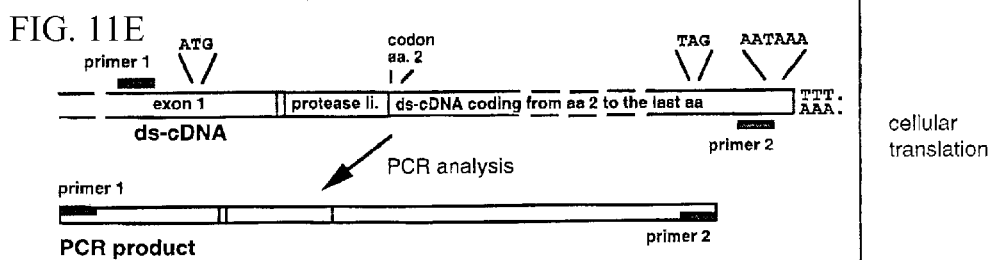
FIG. 11F
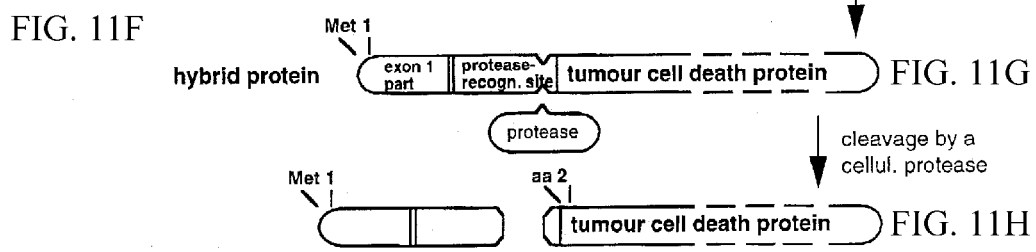
FIG. 11G
FIG. 11H
generation of deadly proteins in tumour cells after trans splicing

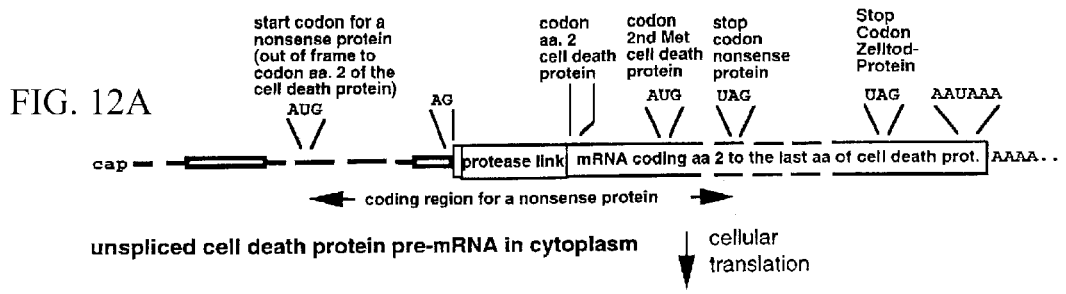
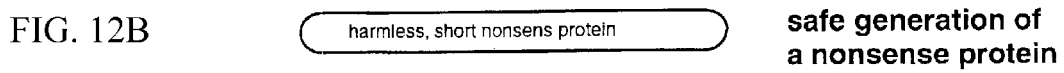
FIG. 12B  safe generation of a nonsense protein
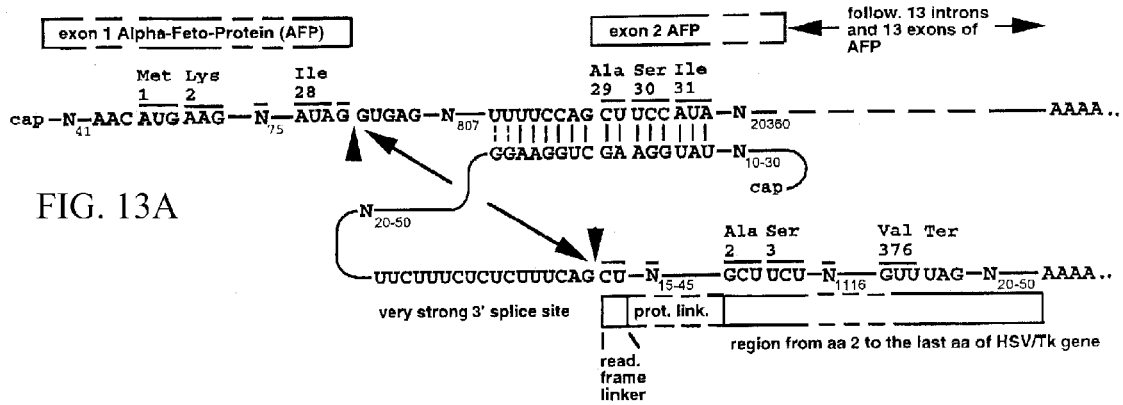
FIG. 13A
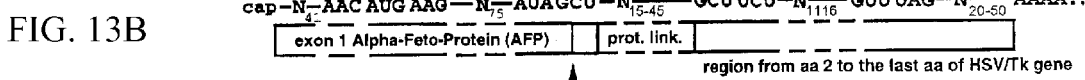
FIG. 13B
active hybrid mRNA with AUG start codon
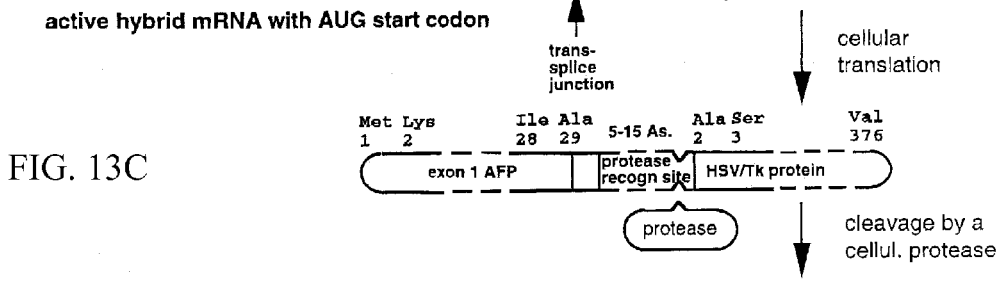
FIG. 13C
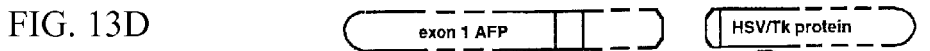
FIG. 13D
generation of active HSV/Tk protein after RNA trans-splicing stimulation of trans-splicing
by mutations in the cis splice sites in N- or C-terminal introns stimulation of trans-splicing
by activating cryptic splice sites in N- or C-terminal exons stimulation of trans-splicing by activating a cryptic splice site in N- or C-terminal exon and a mutation in a cis-splice site in a N-terminal intron step 1: idendification potential pre-mRNAs for RNA trans-splicing step 2: idendification of potential natural cellular trans-splice products principle of identification of yet unknown cellular mRNA trans-splice products

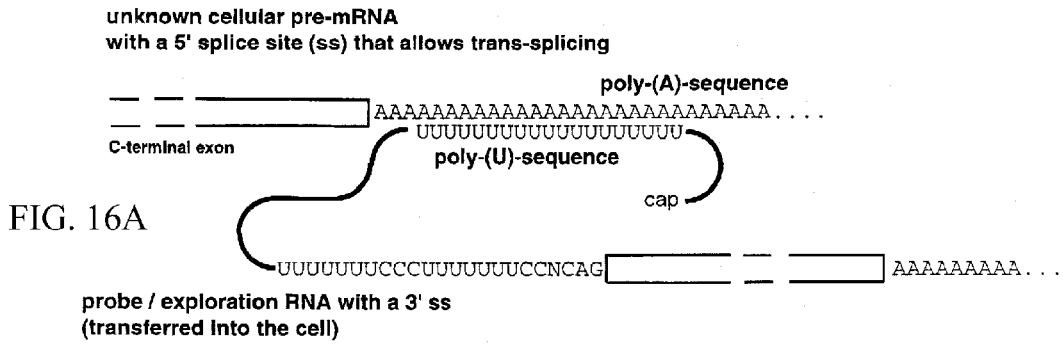

FIG. 16A association between a probe / exploration RNA and a cellular pre-mRNA that allows trans-spling by antisense pairing between a poly-U-region on the probe / exploration RNA and the poly-A-tail-region on the cellular pre-mRNA

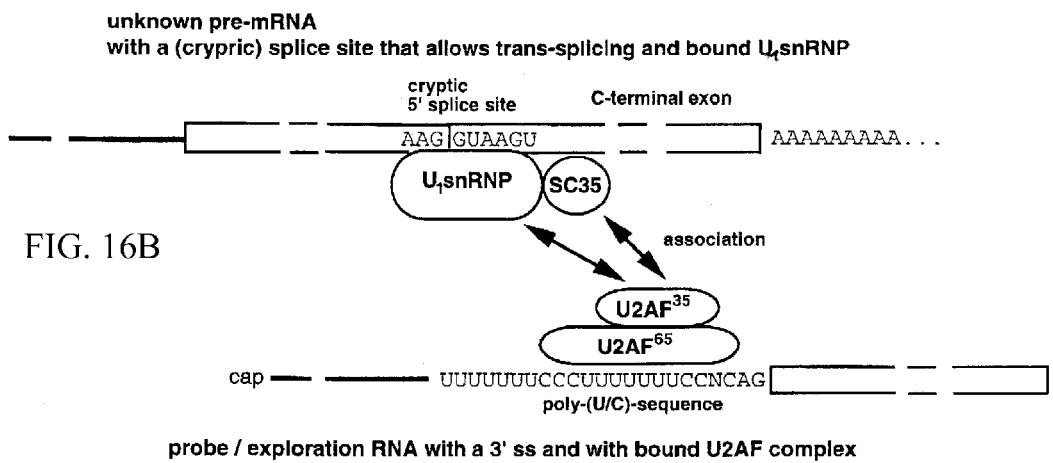

FIG. 16B association of the 3' splice site on a probe / exploration RNA
to a cryptic 5' splice site in a cellular pre-mRNA that allows trans-splicing
by previously bound splice proteins in the E-complex

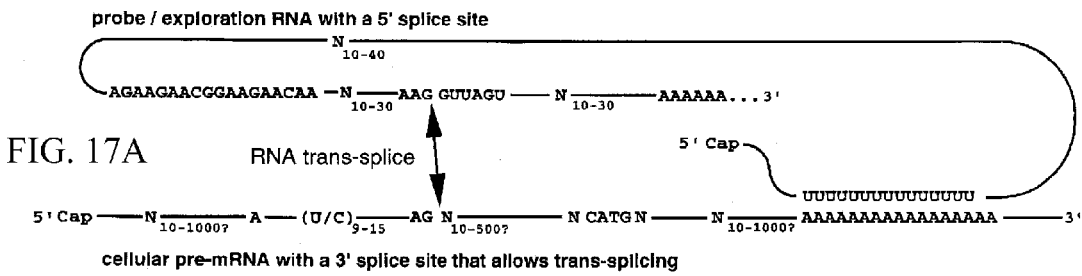
FIG. 17A
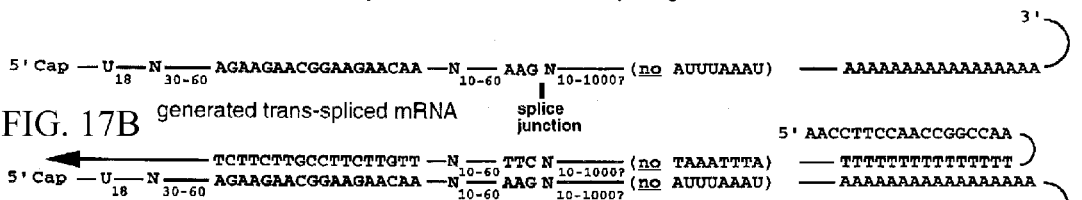
FIG. 17B
FIG. 17C
FIG. 17D
FIG. 17E
FIG. 17F
FIG. 17G
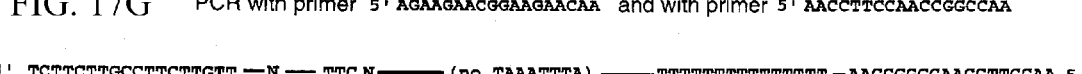
FIG. 17H (case of unspliced probe / explorat. RNA)
FIG. 17I
FIG. 17J cleaved ds-cDNA
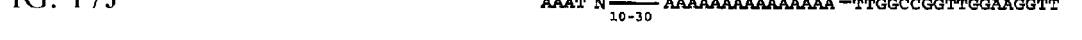
FIG. 17K  PCR with primer AGAAGAACGGAAGAACAA and primer AACCTTCCAACCGGCCAA is unpossible after DNA cleavage

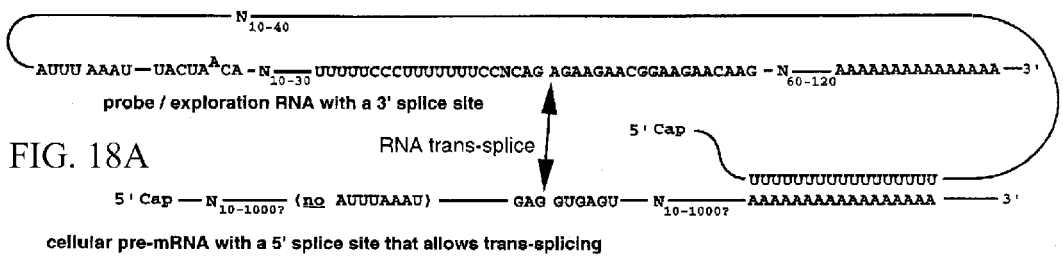

FIG. 18A   probe / exploration RNA with a 3' splice site

RNA trans-splice cellular pre-mRNA with a 5' splice site that allows trans-splicing

FIG. 18B   generated trans-spliced mRNA   splice junction

FIG. 18C   cDNA-synthesis with primer: TTTTTTTTTTTTTTT and after that terminal elongation with cytosins (C)

FIG. 18D   annealing of primer: GGTTGGAAGGTTGGAAGGGGGG   FIG. 18E   complete nucleot. completion to the primer sequence

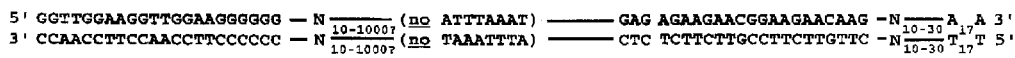

FIG. 18F   2nd strand ds-cDNA synthes. (1 x PCR) with primer:5' GGTTGGAAGGTTGGAAG

FIG. 18G   digest with Swa I: no cleavage possible (no ATTT/AAAT)

FIG. 18H   so far uncleaved ds-cDNA

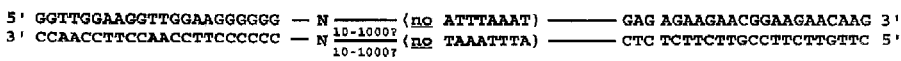

FIG. 18I   PCR with primer 5' GGTTGGAAGGTTGGAAG   and with primer 5' CTTGTTCTTCCGTTCTTCT

FIG. 18J   sequencing with primer GGTTGGAAGGTTGGAAG

(case of unspliced probe / explorat. RNA)

FIG. 18K + FIG. 18L   ▲ DNA cleavage with Swa I

PCR with primer GGTTGGAAGGTTGGAAG and primer CTTGTTCTTCCGTTCTTCT is unpossible after DNA FIG. 18M   cleavage cellular pre-mRNA A with a 5' splice site that allows trans-splicing

sequenced, known nucleotide sequence A

FIG. 19A
RNA trans-splice ?

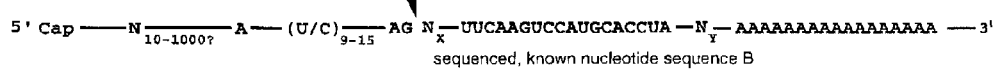
sequenced, known nucleotide sequence B cellular pre-mRNA A with a 3' splice site that allows trans-splicing

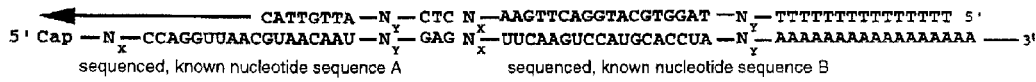
sequenced, known nucleotide sequence A    sequenced, known nucleotide sequence B FIG. 19B if RNA trans-splice occurs in vivo: generated cellular hybrid mRNA ←——————— CATTGTTA —N_Y— CTC N_X—AAGTTCAGGTACGTGGAT —N_Y— TTTTTTTTTTTTTTTT 5'
5' Cap —N_X—CCAGGUUAACGUAACAAU—N_Y— GAG N_X—UUCAAGUCCAUGCACCUA—N_Y— AAAAAAAAAAAAAAAA ——3'
sequenced, known nucleotide sequence A    sequenced, known nucleotide sequence B FIG. 19C cDNA synthesis with primer TTTTTTTTTTTTTTTT 5' CCAGGTTAACGTAACAAT —N— GAG N —TTCAAGTCCATGCACCTA 3'
3' GGTCCAATTGCATTGTTA —N_Y—CTC N_X—AAGTTCAGGTACGTGGAT 5'

FIG. 19D PCR with primer 5' CCAGGTTAACGTAACAAT and primer 5' TAGGTGCATGGACTTGAA

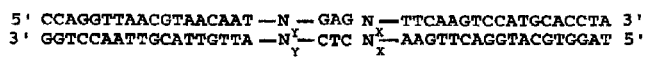

FIG. 19E confirming sequencing with primer CCAGGTTAACGTAACAAT final evidence on natural cellular trans-splice products
generated by trans-splicing between two pre-mRNAs that both allow trans-splicing

SEQUENCE LISTING

```
<160> NUMBER OF SEQ ID NOS: 62

<210> SEQ ID NO 1
<211> LENGTH: 39
<212> TYPE: RNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (15)..(15)
<223> OTHER INFORMATION: branch A site
<220> FEATURE:
<221> NAME/KEY: misc_feature
<222> LOCATION: (36)..(36)
<223> OTHER INFORMATION: n is a, c, g, or u

<400> SEQUENCE: 1
aagguaaguu acuaacuuuu uuucccuuuu uuuccncag                         39

<210> SEQ ID NO 2
<211> LENGTH: 18
<212> TYPE: RNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (15)..(15)
<223> OTHER INFORMATION: branch A site

<400> SEQUENCE: 2
aagguaaguu acuaacag                                                18

<210> SEQ ID NO 3
<211> LENGTH: 5
<212> TYPE: PRT
<213> ORGANISM: Artificial Sequence
<220> FEATURE:
<223> OTHER INFORMATION: artificially synthesized

<400> SEQUENCE: 3

Lys Gly Arg Arg Arg
1               5

<210> SEQ ID NO 4
<211> LENGTH: 61
<212> TYPE: RNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (13)..(40)
<223> OTHER INFORMATION: n is a, c, g, or u
<220> FEATURE:
<221> NAME/KEY: misc_feature
<222> LOCATION: (44)..(45)
<223> OTHER INFORMATION: 5' splice site (moderate, strong)
```

-continued

```
<400> SEQUENCE: 4
aaggguagaa ggnnnnnnnn nnnnnnnnnn nnnnnnnnnn cggguagugc cuuccaaccu    60
u                                                                    61

<210> SEQ ID NO 5
<211> LENGTH: 61
<212> TYPE: RNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (13)..(40)
<223> OTHER INFORMATION: n is a, c, g, or u
<220> FEATURE:
<221> NAME/KEY: misc_feature
<222> LOCATION: (44)..(45)
<223> OTHER INFORMATION: 5' splice site (very strong)

<400> SEQUENCE: 5
aagggaagaa ggnnnnnnnn nnnnnnnnnn nnnnnnnnnn agguaaguc cuuccaaccu     60 u                                                                    61

<210> SEQ ID NO 6
<211> LENGTH: 59
<212> TYPE: RNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (13)..(40)
<223> OTHER INFORMATION: n is a, c, g, or u
<220> FEATURE:
<221> NAME/KEY: misc_feature
<222> LOCATION: (44)..(45)
<223> OTHER INFORMATION: inactivated 5' splice site

<400> SEQUENCE: 6
aaggguagaa ggnnnnnnnn nnnnnnnnnn nnnnnnnnnn cggguagugc cuuccaacc     59

<210> SEQ ID NO 7
<211> LENGTH: 661
<212> TYPE: RNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (1)..(500)
<223> OTHER INFORMATION: n is a, c, g, or u
<220> FEATURE:
<221> NAME/KEY: misc_feature
<222> LOCATION: (513)..(541)
<223> OTHER INFORMATION: n is a, c, g, or u
<220> FEATURE:
<221> NAME/KEY: misc_feature
<222> LOCATION: (545)..(546)
<223> OTHER INFORMATION: splice site
<220> FEATURE:
<221> NAME/KEY: misc_feature
<222> LOCATION: (561)..(600)
<223> OTHER INFORMATION: n is a, c, g, or u
<220> FEATURE:
<221> NAME/KEY: misc_feature
<222> LOCATION: (601)..(615)
<223> OTHER INFORMATION: extended antisense region
<220> FEATURE:
<221> NAME/KEY: misc_feature
<222> LOCATION: (616)..(655)
<223> OTHER INFORMATION: n is a, c, g, or u
```

-continued

```
<220> FEATURE:
<221> NAME/KEY: misc_feature
<222> LOCATION: (656)..(661)
<223> OTHER INFORMATION: poly A sequence

<400> SEQUENCE: 7
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn aagggaagaa ggnnnnnnnn nnnnnnnnnn nnnnnnnnnn     540
naggguaagu ccuuggaacc nnnnnnnnnn nnnnnnnnnn nnnnnnnnnn nnnnnnnnnn     600
gguuggaagg cacuannnnn nnnnnnnnnn nnnnnnnnnn nnnnnnnnnn nnnnnaaaaa     660
a                                                                     661

<210> SEQ ID NO 8
<211> LENGTH: 89
<212> TYPE: RNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (6)..(6)
<223> OTHER INFORMATION: branch A site (moderate, strong)
<220> FEATURE:
<221> NAME/KEY: misc_feature
<222> LOCATION: (9)..(29)
<223> OTHER INFORMATION: n is a, c, g, or u
<220> FEATURE:
<221> NAME/KEY: misc_feature
<222> LOCATION: (30)..(49)
<223> OTHER INFORMATION: U/C region (moderate, strong)
<220> FEATURE:
<221> NAME/KEY: misc_feature
<222> LOCATION: (47)..(48)
<223> OTHER INFORMATION: splice site
<220> FEATURE:
<221> NAME/KEY: misc_feature
<222> LOCATION: (50)..(77)
<223> OTHER INFORMATION: n is a, c, g, or u
<220> FEATURE:
<221> NAME/KEY: misc_feature
<222> LOCATION: (78)..(89)
<223> OTHER INFORMATION: A/G region (not extended, not strong)

<400> SEQUENCE: 8
uguuaaacnn nnnnnnnnnn nnnnnnnnnu uguuugugua uuuuagauun nnnnnnnnnn      60
nnnnnnnnnn nnnnnnnaag gguagaagg                                        89

<210> SEQ ID NO 9
<211> LENGTH: 89
<212> TYPE: RNA
<213> ORGANISM: Artificial Sequence
<220> FEATURE:
<223> OTHER INFORMATION: artificially synthesized
```

```
<220> FEATURE:
<221> NAME/KEY: misc_feature
<222> LOCATION: (6)..(6)
<223> OTHER INFORMATION: branch A site (very strong)
<220> FEATURE:
<221> NAME/KEY: misc_feature
<222> LOCATION: (9)..(29)
<223> OTHER INFORMATION: n is a, c, g, or u
<220> FEATURE:
<221> NAME/KEY: misc_feature
<222> LOCATION: (30)..(49)
<223> OTHER INFORMATION: U/C region (very strong)
<220> FEATURE:
<221> NAME/KEY: misc_feature
<222> LOCATION: (50)..(77)
<223> OTHER INFORMATION: n is a, c, g, or u
<220> FEATURE:
<221> NAME/KEY: misc_feature
<222> LOCATION: (78)..(89)
<223> OTHER INFORMATION: A/G region (extended, strong)

<400> SEQUENCE: 9
uacuaacann nnnnnnnnnn nnnnnnnnnu ucuuucucuc uuucagauun nnnnnnnnnn    60
nnnnnnnnnn nnnnnnnaag ggaagaagg                                     89

<210> SEQ ID NO 10
<211> LENGTH: 49
<212> TYPE: RNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (6)..(6)
<223> OTHER INFORMATION: branch A site
<220> FEATURE:
<221> NAME/KEY: misc_feature
<222> LOCATION: (9)..(29)
<223> OTHER INFORMATION: n is a, c, g, or u
<220> FEATURE:
<221> NAME/KEY: misc_feature
<222> LOCATION: (47)..(48)
<223> OTHER INFORMATION: inactivated 3' splice site

<400> SEQUENCE: 10
uguuaaacnn nnnnnnnnnn nnnnnnnnnu uguuugugua uuuuagauu               49

<210> SEQ ID NO 11
<211> LENGTH: 244
<212> TYPE: RNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (1)..(50)
<223> OTHER INFORMATION: n is a, c, g, or u
<220> FEATURE:
<221> NAME/KEY: misc_feature
<222> LOCATION: (69)..(160)
<223> OTHER INFORMATION: n is a, c, g, or u
<220> FEATURE:
<221> NAME/KEY: misc_feature
<222> LOCATION: (166)..(166)
<223> OTHER INFORMATION: branch A site (very strong)
<220> FEATURE:
<221> NAME/KEY: misc_feature
<222> LOCATION: (169)..(190)
<223> OTHER INFORMATION: n is a, c, g, or u
<220> FEATURE:
<221> NAME/KEY: misc_feature
<222> LOCATION: (191)..(210)
<223> OTHER INFORMATION: U/C region (very strong)
```

```
<220> FEATURE:
<221> NAME/KEY: misc_feature
<222> LOCATION: (208)..(209)
<223> OTHER INFORMATION: splice site
<220> FEATURE:
<221> NAME/KEY: misc_feature
<222> LOCATION: (211)..(232)
<223> OTHER INFORMATION: n is a, c, g, or u

<400> SEQUENCE: 11
nnnnnnnnnn nnnnnnnnnn nnnnnnnnnn nnnnnnnnnn nnnnnnnnnn ucuaaaauac      60
acaaacaann nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn uacuaacann nnnnnnnnnn     180
nnnnnnnnnn uucuuucucu cuuucagauu nnnnnnnnnn nnnnnnnnnn nnaagggaag     240
aagg                                                                 244

<210> SEQ ID NO 12
<211> LENGTH: 21315
<212> TYPE: RNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (1)..(42)
<223> OTHER INFORMATION: n is a, c, g, or u
<220> FEATURE:
<221> NAME/KEY: misc_feature
<222> LOCATION: (52)..(127)
<223> OTHER INFORMATION: n is a, c, g, or u
<220> FEATURE:
<221> NAME/KEY: misc_feature
<222> LOCATION: (137)..(944)
<223> OTHER INFORMATION: n is a, c, g, or u
<220> FEATURE:
<221> NAME/KEY: misc_feature
<222> LOCATION: (961)..(21311)
<223> OTHER INFORMATION: n is a, c, g, or u
<220> FEATURE:
<221> NAME/KEY: misc_feature
<222> LOCATION: (21312)..(21315)
<223> OTHER INFORMATION: poly A sequence

<400> SEQUENCE: 12
nnnnnnnnnn nnnnnnnnnn nnnnnnnnnn nnnnnnnnnn nnaacaugaa gnnnnnnnnn      60
nnnnnnnnnn nnnnnnnnnn nnnnnnnnnn nnnnnnnnnn nnnnnnnnnn nnnnnnnnnn     120
nnnnnnnaua ggugagnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
```

-continued nnnnnnnnnn nnnnnnnnnn nnnnnnnnnn nnnnnnnnnn nnnnnnnnnn nnnnnnnnnn 900
nnnnnnnnnn nnnnnnnnnn nnnnnnnnnn nnnnnnnnnn nnnnuuuucc agcuuccaua 960
nnnnnnnnnn nnnnnnnnnn nnnnnnnnnn nnnnnnnnnn nnnnnnnnnn nnnnnnnnnn 1020
nnnnnnnnnn nnnnnnnnnn nnnnnnnnnn nnnnnnnnnn nnnnnnnnnn nnnnnnnnnn 1080
nnnnnnnnnn nnnnnnnnnn nnnnnnnnnn nnnnnnnnnn nnnnnnnnnn nnnnnnnnnn 1140
nnnnnnnnnn nnnnnnnnnn nnnnnnnnnn nnnnnnnnnn nnnnnnnnnn nnnnnnnnnn 1200
nnnnnnnnnn nnnnnnnnnn nnnnnnnnnn nnnnnnnnnn nnnnnnnnnn nnnnnnnnnn 1260
nnnnnnnnnn nnnnnnnnnn nnnnnnnnnn nnnnnnnnnn nnnnnnnnnn nnnnnnnnnn 1320
nnnnnnnnnn nnnnnnnnnn nnnnnnnnnn nnnnnnnnnn nnnnnnnnnn nnnnnnnnnn 1380
nnnnnnnnnn nnnnnnnnnn nnnnnnnnnn nnnnnnnnnn nnnnnnnnnn nnnnnnnnnn 1440
nnnnnnnnnn nnnnnnnnnn nnnnnnnnnn nnnnnnnnnn nnnnnnnnnn nnnnnnnnnn 1500
nnnnnnnnnn nnnnnnnnnn nnnnnnnnnn nnnnnnnnnn nnnnnnnnnn nnnnnnnnnn 1560
nnnnnnnnnn nnnnnnnnnn nnnnnnnnnn nnnnnnnnnn nnnnnnnnnn nnnnnnnnnn 1620
nnnnnnnnnn nnnnnnnnnn nnnnnnnnnn nnnnnnnnnn nnnnnnnnnn nnnnnnnnnn 1680
nnnnnnnnnn nnnnnnnnnn nnnnnnnnnn nnnnnnnnnn nnnnnnnnnn nnnnnnnnnn 1740
nnnnnnnnnn nnnnnnnnnn nnnnnnnnnn nnnnnnnnnn nnnnnnnnnn nnnnnnnnnn 1800
nnnnnnnnnn nnnnnnnnnn nnnnnnnnnn nnnnnnnnnn nnnnnnnnnn nnnnnnnnnn 1860
nnnnnnnnnn nnnnnnnnnn nnnnnnnnnn nnnnnnnnnn nnnnnnnnnn nnnnnnnnnn 1920
nnnnnnnnnn nnnnnnnnnn nnnnnnnnnn nnnnnnnnnn nnnnnnnnnn nnnnnnnnnn 1980
nnnnnnnnnn nnnnnnnnnn nnnnnnnnnn nnnnnnnnnn nnnnnnnnnn nnnnnnnnnn 2040
nnnnnnnnnn nnnnnnnnnn nnnnnnnnnn nnnnnnnnnn nnnnnnnnnn nnnnnnnnnn 2100
nnnnnnnnnn nnnnnnnnnn nnnnnnnnnn nnnnnnnnnn nnnnnnnnnn nnnnnnnnnn 2160
nnnnnnnnnn nnnnnnnnnn nnnnnnnnnn nnnnnnnnnn nnnnnnnnnn nnnnnnnnnn 2220
nnnnnnnnnn nnnnnnnnnn nnnnnnnnnn nnnnnnnnnn nnnnnnnnnn nnnnnnnnnn 2280
nnnnnnnnnn nnnnnnnnnn nnnnnnnnnn nnnnnnnnnn nnnnnnnnnn nnnnnnnnnn 2340
nnnnnnnnnn nnnnnnnnnn nnnnnnnnnn nnnnnnnnnn nnnnnnnnnn nnnnnnnnnn 2400
nnnnnnnnnn nnnnnnnnnn nnnnnnnnnn nnnnnnnnnn nnnnnnnnnn nnnnnnnnnn 2460
nnnnnnnnnn nnnnnnnnnn nnnnnnnnnn nnnnnnnnnn nnnnnnnnnn nnnnnnnnnn 2520
nnnnnnnnnn nnnnnnnnnn nnnnnnnnnn nnnnnnnnnn nnnnnnnnnn nnnnnnnnnn 2580
nnnnnnnnnn nnnnnnnnnn nnnnnnnnnn nnnnnnnnnn nnnnnnnnnn nnnnnnnnnn 2640
nnnnnnnnnn nnnnnnnnnn nnnnnnnnnn nnnnnnnnnn nnnnnnnnnn nnnnnnnnnn 2700
nnnnnnnnnn nnnnnnnnnn nnnnnnnnnn nnnnnnnnnn nnnnnnnnnn nnnnnnnnnn 2760
nnnnnnnnnn nnnnnnnnnn nnnnnnnnnn nnnnnnnnnn nnnnnnnnnn nnnnnnnnnn 2820
nnnnnnnnnn nnnnnnnnnn nnnnnnnnnn nnnnnnnnnn nnnnnnnnnn nnnnnnnnnn 2880
nnnnnnnnnn nnnnnnnnnn nnnnnnnnnn nnnnnnnnnn nnnnnnnnnn nnnnnnnnnn 2940
nnnnnnnnnn nnnnnnnnnn nnnnnnnnnn nnnnnnnnnn nnnnnnnnnn nnnnnnnnnn 3000
nnnnnnnnnn nnnnnnnnnn nnnnnnnnnn nnnnnnnnnn nnnnnnnnnn nnnnnnnnnn 3060
nnnnnnnnnn nnnnnnnnnn nnnnnnnnnn nnnnnnnnnn nnnnnnnnnn nnnnnnnnnn 3120
nnnnnnnnnn nnnnnnnnnn nnnnnnnnnn nnnnnnnnnn nnnnnnnnnn nnnnnnnnnn 3180
nnnnnnnnnn nnnnnnnnnn nnnnnnnnnn nnnnnnnnnn nnnnnnnnnn nnnnnnnnnn 3240

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 3300 |
| nnnnnnnnnn | nnnnnnnnnn | nnnnnnnnnn | nnnnnnnnnn | nnnnnnnnnn | nnnnnnnnnn | 3360 |
| nnnnnnnnnn | nnnnnnnnnn | nnnnnnnnnn | nnnnnnnnnn | nnnnnnnnnn | nnnnnnnnnn | 3420 |
| nnnnnnnnnn | nnnnnnnnnn | nnnnnnnnnn | nnnnnnnnnn | nnnnnnnnnn | nnnnnnnnnn | 3480 |
| nnnnnnnnnn | nnnnnnnnnn | nnnnnnnnnn | nnnnnnnnnn | nnnnnnnnnn | nnnnnnnnnn | 3540 |
| nnnnnnnnnn | nnnnnnnnnn | nnnnnnnnnn | nnnnnnnnnn | nnnnnnnnnn | nnnnnnnnnn | 3600 |
| nnnnnnnnnn | nnnnnnnnnn | nnnnnnnnnn | nnnnnnnnnn | nnnnnnnnnn | nnnnnnnnnn | 3660 |
| nnnnnnnnnn | nnnnnnnnnn | nnnnnnnnnn | nnnnnnnnnn | nnnnnnnnnn | nnnnnnnnnn | 3720 |
| nnnnnnnnnn | nnnnnnnnnn | nnnnnnnnnn | nnnnnnnnnn | nnnnnnnnnn | nnnnnnnnnn | 3780 |
| nnnnnnnnnn | nnnnnnnnnn | nnnnnnnnnn | nnnnnnnnnn | nnnnnnnnnn | nnnnnnnnnn | 3840 |
| nnnnnnnnnn | nnnnnnnnnn | nnnnnnnnnn | nnnnnnnnnn | nnnnnnnnnn | nnnnnnnnnn | 3900 |
| nnnnnnnnnn | nnnnnnnnnn | nnnnnnnnnn | nnnnnnnnnn | nnnnnnnnnn | nnnnnnnnnn | 3960 |
| nnnnnnnnnn | nnnnnnnnnn | nnnnnnnnnn | nnnnnnnnnn | nnnnnnnnnn | nnnnnnnnnn | 4020 |
| nnnnnnnnnn | nnnnnnnnnn | nnnnnnnnnn | nnnnnnnnnn | nnnnnnnnnn | nnnnnnnnnn | 4080 |
| nnnnnnnnnn | nnnnnnnnnn | nnnnnnnnnn | nnnnnnnnnn | nnnnnnnnnn | nnnnnnnnnn | 4140 |
| nnnnnnnnnn | nnnnnnnnnn | nnnnnnnnnn | nnnnnnnnnn | nnnnnnnnnn | nnnnnnnnnn | 4200 |
| nnnnnnnnnn | nnnnnnnnnn | nnnnnnnnnn | nnnnnnnnnn | nnnnnnnnnn | nnnnnnnnnn | 4260 |
| nnnnnnnnnn | nnnnnnnnnn | nnnnnnnnnn | nnnnnnnnnn | nnnnnnnnnn | nnnnnnnnnn | 4320 |
| nnnnnnnnnn | nnnnnnnnnn | nnnnnnnnnn | nnnnnnnnnn | nnnnnnnnnn | nnnnnnnnnn | 4380 |
| nnnnnnnnnn | nnnnnnnnnn | nnnnnnnnnn | nnnnnnnnnn | nnnnnnnnnn | nnnnnnnnnn | 4440 |
| nnnnnnnnnn | nnnnnnnnnn | nnnnnnnnnn | nnnnnnnnnn | nnnnnnnnnn | nnnnnnnnnn | 4500 |
| nnnnnnnnnn | nnnnnnnnnn | nnnnnnnnnn | nnnnnnnnnn | nnnnnnnnnn | nnnnnnnnnn | 4560 |
| nnnnnnnnnn | nnnnnnnnnn | nnnnnnnnnn | nnnnnnnnnn | nnnnnnnnnn | nnnnnnnnnn | 4620 |
| nnnnnnnnnn | nnnnnnnnnn | nnnnnnnnnn | nnnnnnnnnn | nnnnnnnnnn | nnnnnnnnnn | 4680 |
| nnnnnnnnnn | nnnnnnnnnn | nnnnnnnnnn | nnnnnnnnnn | nnnnnnnnnn | nnnnnnnnnn | 4740 |
| nnnnnnnnnn | nnnnnnnnnn | nnnnnnnnnn | nnnnnnnnnn | nnnnnnnnnn | nnnnnnnnnn | 4800 |
| nnnnnnnnnn | nnnnnnnnnn | nnnnnnnnnn | nnnnnnnnnn | nnnnnnnnnn | nnnnnnnnnn | 4860 |
| nnnnnnnnnn | nnnnnnnnnn | nnnnnnnnnn | nnnnnnnnnn | nnnnnnnnnn | nnnnnnnnnn | 4920 |
| nnnnnnnnnn | nnnnnnnnnn | nnnnnnnnnn | nnnnnnnnnn | nnnnnnnnnn | nnnnnnnnnn | 4980 |
| nnnnnnnnnn | nnnnnnnnnn | nnnnnnnnnn | nnnnnnnnnn | nnnnnnnnnn | nnnnnnnnnn | 5040 |
| nnnnnnnnnn | nnnnnnnnnn | nnnnnnnnnn | nnnnnnnnnn | nnnnnnnnnn | nnnnnnnnnn | 5100 |
| nnnnnnnnnn | nnnnnnnnnn | nnnnnnnnnn | nnnnnnnnnn | nnnnnnnnnn | nnnnnnnnnn | 5160 |
| nnnnnnnnnn | nnnnnnnnnn | nnnnnnnnnn | nnnnnnnnnn | nnnnnnnnnn | nnnnnnnnnn | 5220 |
| nnnnnnnnnn | nnnnnnnnnn | nnnnnnnnnn | nnnnnnnnnn | nnnnnnnnnn | nnnnnnnnnn | 5280 |
| nnnnnnnnnn | nnnnnnnnnn | nnnnnnnnnn | nnnnnnnnnn | nnnnnnnnnn | nnnnnnnnnn | 5340 |
| nnnnnnnnnn | nnnnnnnnnn | nnnnnnnnnn | nnnnnnnnnn | nnnnnnnnnn | nnnnnnnnnn | 5400 |
| nnnnnnnnnn | nnnnnnnnnn | nnnnnnnnnn | nnnnnnnnnn | nnnnnnnnnn | nnnnnnnnnn | 5460 |
| nnnnnnnnnn | nnnnnnnnnn | nnnnnnnnnn | nnnnnnnnnn | nnnnnnnnnn | nnnnnnnnnn | 5520 |
| nnnnnnnnnn | nnnnnnnnnn | nnnnnnnnnn | nnnnnnnnnn | nnnnnnnnnn | nnnnnnnnnn | 5580 |
| nnnnnnnnnn | nnnnnnnnnn | nnnnnnnnnn | nnnnnnnnnn | nnnnnnnnnn | nnnnnnnnnn | 5640 |

| | |
|---|---|
| nnnnnnnnnn nnnnnnnnnn nnnnnnnnnn nnnnnnnnnn nnnnnnnnnn nnnnnnnnnn | 5700 |
| nnnnnnnnnn nnnnnnnnnn nnnnnnnnnn nnnnnnnnnn nnnnnnnnnn nnnnnnnnnn | 5760 |
| nnnnnnnnnn nnnnnnnnnn nnnnnnnnnn nnnnnnnnnn nnnnnnnnnn nnnnnnnnnn | 5820 |
| nnnnnnnnnn nnnnnnnnnn nnnnnnnnnn nnnnnnnnnn nnnnnnnnnn nnnnnnnnnn | 5880 |
| nnnnnnnnnn nnnnnnnnnn nnnnnnnnnn nnnnnnnnnn nnnnnnnnnn nnnnnnnnnn | 5940 |
| nnnnnnnnnn nnnnnnnnnn nnnnnnnnnn nnnnnnnnnn nnnnnnnnnn nnnnnnnnnn | 6000 |
| nnnnnnnnnn nnnnnnnnnn nnnnnnnnnn nnnnnnnnnn nnnnnnnnnn nnnnnnnnnn | 6060 |
| nnnnnnnnnn nnnnnnnnnn nnnnnnnnnn nnnnnnnnnn nnnnnnnnnn nnnnnnnnnn | 6120 |
| nnnnnnnnnn nnnnnnnnnn nnnnnnnnnn nnnnnnnnnn nnnnnnnnnn nnnnnnnnnn | 6180 |
| nnnnnnnnnn nnnnnnnnnn nnnnnnnnnn nnnnnnnnnn nnnnnnnnnn nnnnnnnnnn | 6240 |
| nnnnnnnnnn nnnnnnnnnn nnnnnnnnnn nnnnnnnnnn nnnnnnnnnn nnnnnnnnnn | 6300 |
| nnnnnnnnnn nnnnnnnnnn nnnnnnnnnn nnnnnnnnnn nnnnnnnnnn nnnnnnnnnn | 6360 |
| nnnnnnnnnn nnnnnnnnnn nnnnnnnnnn nnnnnnnnnn nnnnnnnnnn nnnnnnnnnn | 6420 |
| nnnnnnnnnn nnnnnnnnnn nnnnnnnnnn nnnnnnnnnn nnnnnnnnnn nnnnnnnnnn | 6480 |
| nnnnnnnnnn nnnnnnnnnn nnnnnnnnnn nnnnnnnnnn nnnnnnnnnn nnnnnnnnnn | 6540 |
| nnnnnnnnnn nnnnnnnnnn nnnnnnnnnn nnnnnnnnnn nnnnnnnnnn nnnnnnnnnn | 6600 |
| nnnnnnnnnn nnnnnnnnnn nnnnnnnnnn nnnnnnnnnn nnnnnnnnnn nnnnnnnnnn | 6660 |
| nnnnnnnnnn nnnnnnnnnn nnnnnnnnnn nnnnnnnnnn nnnnnnnnnn nnnnnnnnnn | 6720 |
| nnnnnnnnnn nnnnnnnnnn nnnnnnnnnn nnnnnnnnnn nnnnnnnnnn nnnnnnnnnn | 6780 |
| nnnnnnnnnn nnnnnnnnnn nnnnnnnnnn nnnnnnnnnn nnnnnnnnnn nnnnnnnnnn | 6840 |
| nnnnnnnnnn nnnnnnnnnn nnnnnnnnnn nnnnnnnnnn nnnnnnnnnn nnnnnnnnnn | 6900 |
| nnnnnnnnnn nnnnnnnnnn nnnnnnnnnn nnnnnnnnnn nnnnnnnnnn nnnnnnnnnn | 6960 |
| nnnnnnnnnn nnnnnnnnnn nnnnnnnnnn nnnnnnnnnn nnnnnnnnnn nnnnnnnnnn | 7020 |
| nnnnnnnnnn nnnnnnnnnn nnnnnnnnnn nnnnnnnnnn nnnnnnnnnn nnnnnnnnnn | 7080 |
| nnnnnnnnnn nnnnnnnnnn nnnnnnnnnn nnnnnnnnnn nnnnnnnnnn nnnnnnnnnn | 7140 |
| nnnnnnnnnn nnnnnnnnnn nnnnnnnnnn nnnnnnnnnn nnnnnnnnnn nnnnnnnnnn | 7200 |
| nnnnnnnnnn nnnnnnnnnn nnnnnnnnnn nnnnnnnnnn nnnnnnnnnn nnnnnnnnnn | 7260 |
| nnnnnnnnnn nnnnnnnnnn nnnnnnnnnn nnnnnnnnnn nnnnnnnnnn nnnnnnnnnn | 7320 |
| nnnnnnnnnn nnnnnnnnnn nnnnnnnnnn nnnnnnnnnn nnnnnnnnnn nnnnnnnnnn | 7380 |
| nnnnnnnnnn nnnnnnnnnn nnnnnnnnnn nnnnnnnnnn nnnnnnnnnn nnnnnnnnnn | 7440 |
| nnnnnnnnnn nnnnnnnnnn nnnnnnnnnn nnnnnnnnnn nnnnnnnnnn nnnnnnnnnn | 7500 |
| nnnnnnnnnn nnnnnnnnnn nnnnnnnnnn nnnnnnnnnn nnnnnnnnnn nnnnnnnnnn | 7560 |
| nnnnnnnnnn nnnnnnnnnn nnnnnnnnnn nnnnnnnnnn nnnnnnnnnn nnnnnnnnnn | 7620 |
| nnnnnnnnnn nnnnnnnnnn nnnnnnnnnn nnnnnnnnnn nnnnnnnnnn nnnnnnnnnn | 7680 |
| nnnnnnnnnn nnnnnnnnnn nnnnnnnnnn nnnnnnnnnn nnnnnnnnnn nnnnnnnnnn | 7740 |
| nnnnnnnnnn nnnnnnnnnn nnnnnnnnnn nnnnnnnnnn nnnnnnnnnn nnnnnnnnnn | 7800 |
| nnnnnnnnnn nnnnnnnnnn nnnnnnnnnn nnnnnnnnnn nnnnnnnnnn nnnnnnnnnn | 7860 |
| nnnnnnnnnn nnnnnnnnnn nnnnnnnnnn nnnnnnnnnn nnnnnnnnnn nnnnnnnnnn | 7920 |
| nnnnnnnnnn nnnnnnnnnn nnnnnnnnnn nnnnnnnnnn nnnnnnnnnn nnnnnnnnnn | 7980 |
| nnnnnnnnnn nnnnnnnnnn nnnnnnnnnn nnnnnnnnnn nnnnnnnnnn nnnnnnnnnn | 8040 |

-continued

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 8100 |
| nnnnnnnnnn | nnnnnnnnnn | nnnnnnnnnn | nnnnnnnnnn | nnnnnnnnnn | nnnnnnnnnn | 8160 |
| nnnnnnnnnn | nnnnnnnnnn | nnnnnnnnnn | nnnnnnnnnn | nnnnnnnnnn | nnnnnnnnnn | 8220 |
| nnnnnnnnnn | nnnnnnnnnn | nnnnnnnnnn | nnnnnnnnnn | nnnnnnnnnn | nnnnnnnnnn | 8280 |
| nnnnnnnnnn | nnnnnnnnnn | nnnnnnnnnn | nnnnnnnnnn | nnnnnnnnnn | nnnnnnnnnn | 8340 |
| nnnnnnnnnn | nnnnnnnnnn | nnnnnnnnnn | nnnnnnnnnn | nnnnnnnnnn | nnnnnnnnnn | 8400 |
| nnnnnnnnnn | nnnnnnnnnn | nnnnnnnnnn | nnnnnnnnnn | nnnnnnnnnn | nnnnnnnnnn | 8460 |
| nnnnnnnnnn | nnnnnnnnnn | nnnnnnnnnn | nnnnnnnnnn | nnnnnnnnnn | nnnnnnnnnn | 8520 |
| nnnnnnnnnn | nnnnnnnnnn | nnnnnnnnnn | nnnnnnnnnn | nnnnnnnnnn | nnnnnnnnnn | 8580 |
| nnnnnnnnnn | nnnnnnnnnn | nnnnnnnnnn | nnnnnnnnnn | nnnnnnnnnn | nnnnnnnnnn | 8640 |
| nnnnnnnnnn | nnnnnnnnnn | nnnnnnnnnn | nnnnnnnnnn | nnnnnnnnnn | nnnnnnnnnn | 8700 |
| nnnnnnnnnn | nnnnnnnnnn | nnnnnnnnnn | nnnnnnnnnn | nnnnnnnnnn | nnnnnnnnnn | 8760 |
| nnnnnnnnnn | nnnnnnnnnn | nnnnnnnnnn | nnnnnnnnnn | nnnnnnnnnn | nnnnnnnnnn | 8820 |
| nnnnnnnnnn | nnnnnnnnnn | nnnnnnnnnn | nnnnnnnnnn | nnnnnnnnnn | nnnnnnnnnn | 8880 |
| nnnnnnnnnn | nnnnnnnnnn | nnnnnnnnnn | nnnnnnnnnn | nnnnnnnnnn | nnnnnnnnnn | 8940 |
| nnnnnnnnnn | nnnnnnnnnn | nnnnnnnnnn | nnnnnnnnnn | nnnnnnnnnn | nnnnnnnnnn | 9000 |
| nnnnnnnnnn | nnnnnnnnnn | nnnnnnnnnn | nnnnnnnnnn | nnnnnnnnnn | nnnnnnnnnn | 9060 |
| nnnnnnnnnn | nnnnnnnnnn | nnnnnnnnnn | nnnnnnnnnn | nnnnnnnnnn | nnnnnnnnnn | 9120 |
| nnnnnnnnnn | nnnnnnnnnn | nnnnnnnnnn | nnnnnnnnnn | nnnnnnnnnn | nnnnnnnnnn | 9180 |
| nnnnnnnnnn | nnnnnnnnnn | nnnnnnnnnn | nnnnnnnnnn | nnnnnnnnnn | nnnnnnnnnn | 9240 |
| nnnnnnnnnn | nnnnnnnnnn | nnnnnnnnnn | nnnnnnnnnn | nnnnnnnnnn | nnnnnnnnnn | 9300 |
| nnnnnnnnnn | nnnnnnnnnn | nnnnnnnnnn | nnnnnnnnnn | nnnnnnnnnn | nnnnnnnnnn | 9360 |
| nnnnnnnnnn | nnnnnnnnnn | nnnnnnnnnn | nnnnnnnnnn | nnnnnnnnnn | nnnnnnnnnn | 9420 |
| nnnnnnnnnn | nnnnnnnnnn | nnnnnnnnnn | nnnnnnnnnn | nnnnnnnnnn | nnnnnnnnnn | 9480 |
| nnnnnnnnnn | nnnnnnnnnn | nnnnnnnnnn | nnnnnnnnnn | nnnnnnnnnn | nnnnnnnnnn | 9540 |
| nnnnnnnnnn | nnnnnnnnnn | nnnnnnnnnn | nnnnnnnnnn | nnnnnnnnnn | nnnnnnnnnn | 9600 |
| nnnnnnnnnn | nnnnnnnnnn | nnnnnnnnnn | nnnnnnnnnn | nnnnnnnnnn | nnnnnnnnnn | 9660 |
| nnnnnnnnnn | nnnnnnnnnn | nnnnnnnnnn | nnnnnnnnnn | nnnnnnnnnn | nnnnnnnnnn | 9720 |
| nnnnnnnnnn | nnnnnnnnnn | nnnnnnnnnn | nnnnnnnnnn | nnnnnnnnnn | nnnnnnnnnn | 9780 |
| nnnnnnnnnn | nnnnnnnnnn | nnnnnnnnnn | nnnnnnnnnn | nnnnnnnnnn | nnnnnnnnnn | 9840 |
| nnnnnnnnnn | nnnnnnnnnn | nnnnnnnnnn | nnnnnnnnnn | nnnnnnnnnn | nnnnnnnnnn | 9900 |
| nnnnnnnnnn | nnnnnnnnnn | nnnnnnnnnn | nnnnnnnnnn | nnnnnnnnnn | nnnnnnnnnn | 9960 |
| nnnnnnnnnn | nnnnnnnnnn | nnnnnnnnnn | nnnnnnnnnn | nnnnnnnnnn | nnnnnnnnnn | 10020 |
| nnnnnnnnnn | nnnnnnnnnn | nnnnnnnnnn | nnnnnnnnnn | nnnnnnnnnn | nnnnnnnnnn | 10080 |
| nnnnnnnnnn | nnnnnnnnnn | nnnnnnnnnn | nnnnnnnnnn | nnnnnnnnnn | nnnnnnnnnn | 10140 |
| nnnnnnnnnn | nnnnnnnnnn | nnnnnnnnnn | nnnnnnnnnn | nnnnnnnnnn | nnnnnnnnnn | 10200 |
| nnnnnnnnnn | nnnnnnnnnn | nnnnnnnnnn | nnnnnnnnnn | nnnnnnnnnn | nnnnnnnnnn | 10260 |
| nnnnnnnnnn | nnnnnnnnnn | nnnnnnnnnn | nnnnnnnnnn | nnnnnnnnnn | nnnnnnnnnn | 10320 |
| nnnnnnnnnn | nnnnnnnnnn | nnnnnnnnnn | nnnnnnnnnn | nnnnnnnnnn | nnnnnnnnnn | 10380 |
| nnnnnnnnnn | nnnnnnnnnn | nnnnnnnnnn | nnnnnnnnnn | nnnnnnnnnn | nnnnnnnnnn | 10440 |

-continued

```
nnnnnnnnnn nnnnnnnnnn nnnnnnnnnn nnnnnnnnnn nnnnnnnnnn nnnnnnnnnn    10500
nnnnnnnnnn nnnnnnnnnn nnnnnnnnnn nnnnnnnnnn nnnnnnnnnn nnnnnnnnnn    10560
nnnnnnnnnn nnnnnnnnnn nnnnnnnnnn nnnnnnnnnn nnnnnnnnnn nnnnnnnnnn    10620
nnnnnnnnnn nnnnnnnnnn nnnnnnnnnn nnnnnnnnnn nnnnnnnnnn nnnnnnnnnn    10680
nnnnnnnnnn nnnnnnnnnn nnnnnnnnnn nnnnnnnnnn nnnnnnnnnn nnnnnnnnnn    10740
nnnnnnnnnn nnnnnnnnnn nnnnnnnnnn nnnnnnnnnn nnnnnnnnnn nnnnnnnnnn    10800
nnnnnnnnnn nnnnnnnnnn nnnnnnnnnn nnnnnnnnnn nnnnnnnnnn nnnnnnnnnn    10860
nnnnnnnnnn nnnnnnnnnn nnnnnnnnnn nnnnnnnnnn nnnnnnnnnn nnnnnnnnnn    10920
nnnnnnnnnn nnnnnnnnnn nnnnnnnnnn nnnnnnnnnn nnnnnnnnnn nnnnnnnnnn    10980
nnnnnnnnnn nnnnnnnnnn nnnnnnnnnn nnnnnnnnnn nnnnnnnnnn nnnnnnnnnn    11040
nnnnnnnnnn nnnnnnnnnn nnnnnnnnnn nnnnnnnnnn nnnnnnnnnn nnnnnnnnnn    11100
nnnnnnnnnn nnnnnnnnnn nnnnnnnnnn nnnnnnnnnn nnnnnnnnnn nnnnnnnnnn    11160
nnnnnnnnnn nnnnnnnnnn nnnnnnnnnn nnnnnnnnnn nnnnnnnnnn nnnnnnnnnn    11220
nnnnnnnnnn nnnnnnnnnn nnnnnnnnnn nnnnnnnnnn nnnnnnnnnn nnnnnnnnnn    11280
nnnnnnnnnn nnnnnnnnnn nnnnnnnnnn nnnnnnnnnn nnnnnnnnnn nnnnnnnnnn    11340
nnnnnnnnnn nnnnnnnnnn nnnnnnnnnn nnnnnnnnnn nnnnnnnnnn nnnnnnnnnn    11400
nnnnnnnnnn nnnnnnnnnn nnnnnnnnnn nnnnnnnnnn nnnnnnnnnn nnnnnnnnnn    11460
nnnnnnnnnn nnnnnnnnnn nnnnnnnnnn nnnnnnnnnn nnnnnnnnnn nnnnnnnnnn    11520
nnnnnnnnnn nnnnnnnnnn nnnnnnnnnn nnnnnnnnnn nnnnnnnnnn nnnnnnnnnn    11580
nnnnnnnnnn nnnnnnnnnn nnnnnnnnnn nnnnnnnnnn nnnnnnnnnn nnnnnnnnnn    11640
nnnnnnnnnn nnnnnnnnnn nnnnnnnnnn nnnnnnnnnn nnnnnnnnnn nnnnnnnnnn    11700
nnnnnnnnnn nnnnnnnnnn nnnnnnnnnn nnnnnnnnnn nnnnnnnnnn nnnnnnnnnn    11760
nnnnnnnnnn nnnnnnnnnn nnnnnnnnnn nnnnnnnnnn nnnnnnnnnn nnnnnnnnnn    11820
nnnnnnnnnn nnnnnnnnnn nnnnnnnnnn nnnnnnnnnn nnnnnnnnnn nnnnnnnnnn    11880
nnnnnnnnnn nnnnnnnnnn nnnnnnnnnn nnnnnnnnnn nnnnnnnnnn nnnnnnnnnn    11940
nnnnnnnnnn nnnnnnnnnn nnnnnnnnnn nnnnnnnnnn nnnnnnnnnn nnnnnnnnnn    12000
nnnnnnnnnn nnnnnnnnnn nnnnnnnnnn nnnnnnnnnn nnnnnnnnnn nnnnnnnnnn    12060
nnnnnnnnnn nnnnnnnnnn nnnnnnnnnn nnnnnnnnnn nnnnnnnnnn nnnnnnnnnn    12120
nnnnnnnnnn nnnnnnnnnn nnnnnnnnnn nnnnnnnnnn nnnnnnnnnn nnnnnnnnnn    12180
nnnnnnnnnn nnnnnnnnnn nnnnnnnnnn nnnnnnnnnn nnnnnnnnnn nnnnnnnnnn    12240
nnnnnnnnnn nnnnnnnnnn nnnnnnnnnn nnnnnnnnnn nnnnnnnnnn nnnnnnnnnn    12300
nnnnnnnnnn nnnnnnnnnn nnnnnnnnnn nnnnnnnnnn nnnnnnnnnn nnnnnnnnnn    12360
nnnnnnnnnn nnnnnnnnnn nnnnnnnnnn nnnnnnnnnn nnnnnnnnnn nnnnnnnnnn    12420
nnnnnnnnnn nnnnnnnnnn nnnnnnnnnn nnnnnnnnnn nnnnnnnnnn nnnnnnnnnn    12480
nnnnnnnnnn nnnnnnnnnn nnnnnnnnnn nnnnnnnnnn nnnnnnnnnn nnnnnnnnnn    12540
nnnnnnnnnn nnnnnnnnnn nnnnnnnnnn nnnnnnnnnn nnnnnnnnnn nnnnnnnnnn    12600
nnnnnnnnnn nnnnnnnnnn nnnnnnnnnn nnnnnnnnnn nnnnnnnnnn nnnnnnnnnn    12660
nnnnnnnnnn nnnnnnnnnn nnnnnnnnnn nnnnnnnnnn nnnnnnnnnn nnnnnnnnnn    12720
nnnnnnnnnn nnnnnnnnnn nnnnnnnnnn nnnnnnnnnn nnnnnnnnnn nnnnnnnnnn    12780
nnnnnnnnnn nnnnnnnnnn nnnnnnnnnn nnnnnnnnnn nnnnnnnnnn nnnnnnnnnn    12840
```

```
nnnnnnnnnn nnnnnnnnnn nnnnnnnnnn nnnnnnnnnn nnnnnnnnnn nnnnnnnnnn    12900
nnnnnnnnnn nnnnnnnnnn nnnnnnnnnn nnnnnnnnnn nnnnnnnnnn nnnnnnnnnn    12960
nnnnnnnnnn nnnnnnnnnn nnnnnnnnnn nnnnnnnnnn nnnnnnnnnn nnnnnnnnnn    13020
nnnnnnnnnn nnnnnnnnnn nnnnnnnnnn nnnnnnnnnn nnnnnnnnnn nnnnnnnnnn    13080
nnnnnnnnnn nnnnnnnnnn nnnnnnnnnn nnnnnnnnnn nnnnnnnnnn nnnnnnnnnn    13140
nnnnnnnnnn nnnnnnnnnn nnnnnnnnnn nnnnnnnnnn nnnnnnnnnn nnnnnnnnnn    13200
nnnnnnnnnn nnnnnnnnnn nnnnnnnnnn nnnnnnnnnn nnnnnnnnnn nnnnnnnnnn    13260
nnnnnnnnnn nnnnnnnnnn nnnnnnnnnn nnnnnnnnnn nnnnnnnnnn nnnnnnnnnn    13320
nnnnnnnnnn nnnnnnnnnn nnnnnnnnnn nnnnnnnnnn nnnnnnnnnn nnnnnnnnnn    13380
nnnnnnnnnn nnnnnnnnnn nnnnnnnnnn nnnnnnnnnn nnnnnnnnnn nnnnnnnnnn    13440
nnnnnnnnnn nnnnnnnnnn nnnnnnnnnn nnnnnnnnnn nnnnnnnnnn nnnnnnnnnn    13500
nnnnnnnnnn nnnnnnnnnn nnnnnnnnnn nnnnnnnnnn nnnnnnnnnn nnnnnnnnnn    13560
nnnnnnnnnn nnnnnnnnnn nnnnnnnnnn nnnnnnnnnn nnnnnnnnnn nnnnnnnnnn    13620
nnnnnnnnnn nnnnnnnnnn nnnnnnnnnn nnnnnnnnnn nnnnnnnnnn nnnnnnnnnn    13680
nnnnnnnnnn nnnnnnnnnn nnnnnnnnnn nnnnnnnnnn nnnnnnnnnn nnnnnnnnnn    13740
nnnnnnnnnn nnnnnnnnnn nnnnnnnnnn nnnnnnnnnn nnnnnnnnnn nnnnnnnnnn    13800
nnnnnnnnnn nnnnnnnnnn nnnnnnnnnn nnnnnnnnnn nnnnnnnnnn nnnnnnnnnn    13860
nnnnnnnnnn nnnnnnnnnn nnnnnnnnnn nnnnnnnnnn nnnnnnnnnn nnnnnnnnnn    13920
nnnnnnnnnn nnnnnnnnnn nnnnnnnnnn nnnnnnnnnn nnnnnnnnnn nnnnnnnnnn    13980
nnnnnnnnnn nnnnnnnnnn nnnnnnnnnn nnnnnnnnnn nnnnnnnnnn nnnnnnnnnn    14040
nnnnnnnnnn nnnnnnnnnn nnnnnnnnnn nnnnnnnnnn nnnnnnnnnn nnnnnnnnnn    14100
nnnnnnnnnn nnnnnnnnnn nnnnnnnnnn nnnnnnnnnn nnnnnnnnnn nnnnnnnnnn    14160
nnnnnnnnnn nnnnnnnnnn nnnnnnnnnn nnnnnnnnnn nnnnnnnnnn nnnnnnnnnn    14220
nnnnnnnnnn nnnnnnnnnn nnnnnnnnnn nnnnnnnnnn nnnnnnnnnn nnnnnnnnnn    14280
nnnnnnnnnn nnnnnnnnnn nnnnnnnnnn nnnnnnnnnn nnnnnnnnnn nnnnnnnnnn    14340
nnnnnnnnnn nnnnnnnnnn nnnnnnnnnn nnnnnnnnnn nnnnnnnnnn nnnnnnnnnn    14400
nnnnnnnnnn nnnnnnnnnn nnnnnnnnnn nnnnnnnnnn nnnnnnnnnn nnnnnnnnnn    14460
nnnnnnnnnn nnnnnnnnnn nnnnnnnnnn nnnnnnnnnn nnnnnnnnnn nnnnnnnnnn    14520
nnnnnnnnnn nnnnnnnnnn nnnnnnnnnn nnnnnnnnnn nnnnnnnnnn nnnnnnnnnn    14580
nnnnnnnnnn nnnnnnnnnn nnnnnnnnnn nnnnnnnnnn nnnnnnnnnn nnnnnnnnnn    14640
nnnnnnnnnn nnnnnnnnnn nnnnnnnnnn nnnnnnnnnn nnnnnnnnnn nnnnnnnnnn    14700
nnnnnnnnnn nnnnnnnnnn nnnnnnnnnn nnnnnnnnnn nnnnnnnnnn nnnnnnnnnn    14760
nnnnnnnnnn nnnnnnnnnn nnnnnnnnnn nnnnnnnnnn nnnnnnnnnn nnnnnnnnnn    14820
nnnnnnnnnn nnnnnnnnnn nnnnnnnnnn nnnnnnnnnn nnnnnnnnnn nnnnnnnnnn    14880
nnnnnnnnnn nnnnnnnnnn nnnnnnnnnn nnnnnnnnnn nnnnnnnnnn nnnnnnnnnn    14940
nnnnnnnnnn nnnnnnnnnn nnnnnnnnnn nnnnnnnnnn nnnnnnnnnn nnnnnnnnnn    15000
nnnnnnnnnn nnnnnnnnnn nnnnnnnnnn nnnnnnnnnn nnnnnnnnnn nnnnnnnnnn    15060
nnnnnnnnnn nnnnnnnnnn nnnnnnnnnn nnnnnnnnnn nnnnnnnnnn nnnnnnnnnn    15120
nnnnnnnnnn nnnnnnnnnn nnnnnnnnnn nnnnnnnnnn nnnnnnnnnn nnnnnnnnnn    15180
nnnnnnnnnn nnnnnnnnnn nnnnnnnnnn nnnnnnnnnn nnnnnnnnnn nnnnnnnnnn    15240
```

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 15300 |
| nnnnnnnnnn | nnnnnnnnnn | nnnnnnnnnn | nnnnnnnnnn | nnnnnnnnnn | nnnnnnnnnn | 15360 |
| nnnnnnnnnn | nnnnnnnnnn | nnnnnnnnnn | nnnnnnnnnn | nnnnnnnnnn | nnnnnnnnnn | 15420 |
| nnnnnnnnnn | nnnnnnnnnn | nnnnnnnnnn | nnnnnnnnnn | nnnnnnnnnn | nnnnnnnnnn | 15480 |
| nnnnnnnnnn | nnnnnnnnnn | nnnnnnnnnn | nnnnnnnnnn | nnnnnnnnnn | nnnnnnnnnn | 15540 |
| nnnnnnnnnn | nnnnnnnnnn | nnnnnnnnnn | nnnnnnnnnn | nnnnnnnnnn | nnnnnnnnnn | 15600 |
| nnnnnnnnnn | nnnnnnnnnn | nnnnnnnnnn | nnnnnnnnnn | nnnnnnnnnn | nnnnnnnnnn | 15660 |
| nnnnnnnnnn | nnnnnnnnnn | nnnnnnnnnn | nnnnnnnnnn | nnnnnnnnnn | nnnnnnnnnn | 15720 |
| nnnnnnnnnn | nnnnnnnnnn | nnnnnnnnnn | nnnnnnnnnn | nnnnnnnnnn | nnnnnnnnnn | 15780 |
| nnnnnnnnnn | nnnnnnnnnn | nnnnnnnnnn | nnnnnnnnnn | nnnnnnnnnn | nnnnnnnnnn | 15840 |
| nnnnnnnnnn | nnnnnnnnnn | nnnnnnnnnn | nnnnnnnnnn | nnnnnnnnnn | nnnnnnnnnn | 15900 |
| nnnnnnnnnn | nnnnnnnnnn | nnnnnnnnnn | nnnnnnnnnn | nnnnnnnnnn | nnnnnnnnnn | 15960 |
| nnnnnnnnnn | nnnnnnnnnn | nnnnnnnnnn | nnnnnnnnnn | nnnnnnnnnn | nnnnnnnnnn | 16020 |
| nnnnnnnnnn | nnnnnnnnnn | nnnnnnnnnn | nnnnnnnnnn | nnnnnnnnnn | nnnnnnnnnn | 16080 |
| nnnnnnnnnn | nnnnnnnnnn | nnnnnnnnnn | nnnnnnnnnn | nnnnnnnnnn | nnnnnnnnnn | 16140 |
| nnnnnnnnnn | nnnnnnnnnn | nnnnnnnnnn | nnnnnnnnnn | nnnnnnnnnn | nnnnnnnnnn | 16200 |
| nnnnnnnnnn | nnnnnnnnnn | nnnnnnnnnn | nnnnnnnnnn | nnnnnnnnnn | nnnnnnnnnn | 16260 |
| nnnnnnnnnn | nnnnnnnnnn | nnnnnnnnnn | nnnnnnnnnn | nnnnnnnnnn | nnnnnnnnnn | 16320 |
| nnnnnnnnnn | nnnnnnnnnn | nnnnnnnnnn | nnnnnnnnnn | nnnnnnnnnn | nnnnnnnnnn | 16380 |
| nnnnnnnnnn | nnnnnnnnnn | nnnnnnnnnn | nnnnnnnnnn | nnnnnnnnnn | nnnnnnnnnn | 16440 |
| nnnnnnnnnn | nnnnnnnnnn | nnnnnnnnnn | nnnnnnnnnn | nnnnnnnnnn | nnnnnnnnnn | 16500 |
| nnnnnnnnnn | nnnnnnnnnn | nnnnnnnnnn | nnnnnnnnnn | nnnnnnnnnn | nnnnnnnnnn | 16560 |
| nnnnnnnnnn | nnnnnnnnnn | nnnnnnnnnn | nnnnnnnnnn | nnnnnnnnnn | nnnnnnnnnn | 16620 |
| nnnnnnnnnn | nnnnnnnnnn | nnnnnnnnnn | nnnnnnnnnn | nnnnnnnnnn | nnnnnnnnnn | 16680 |
| nnnnnnnnnn | nnnnnnnnnn | nnnnnnnnnn | nnnnnnnnnn | nnnnnnnnnn | nnnnnnnnnn | 16740 |
| nnnnnnnnnn | nnnnnnnnnn | nnnnnnnnnn | nnnnnnnnnn | nnnnnnnnnn | nnnnnnnnnn | 16800 |
| nnnnnnnnnn | nnnnnnnnnn | nnnnnnnnnn | nnnnnnnnnn | nnnnnnnnnn | nnnnnnnnnn | 16860 |
| nnnnnnnnnn | nnnnnnnnnn | nnnnnnnnnn | nnnnnnnnnn | nnnnnnnnnn | nnnnnnnnnn | 16920 |
| nnnnnnnnnn | nnnnnnnnnn | nnnnnnnnnn | nnnnnnnnnn | nnnnnnnnnn | nnnnnnnnnn | 16980 |
| nnnnnnnnnn | nnnnnnnnnn | nnnnnnnnnn | nnnnnnnnnn | nnnnnnnnnn | nnnnnnnnnn | 17040 |
| nnnnnnnnnn | nnnnnnnnnn | nnnnnnnnnn | nnnnnnnnnn | nnnnnnnnnn | nnnnnnnnnn | 17100 |
| nnnnnnnnnn | nnnnnnnnnn | nnnnnnnnnn | nnnnnnnnnn | nnnnnnnnnn | nnnnnnnnnn | 17160 |
| nnnnnnnnnn | nnnnnnnnnn | nnnnnnnnnn | nnnnnnnnnn | nnnnnnnnnn | nnnnnnnnnn | 17220 |
| nnnnnnnnnn | nnnnnnnnnn | nnnnnnnnnn | nnnnnnnnnn | nnnnnnnnnn | nnnnnnnnnn | 17280 |
| nnnnnnnnnn | nnnnnnnnnn | nnnnnnnnnn | nnnnnnnnnn | nnnnnnnnnn | nnnnnnnnnn | 17340 |
| nnnnnnnnnn | nnnnnnnnnn | nnnnnnnnnn | nnnnnnnnnn | nnnnnnnnnn | nnnnnnnnnn | 17400 |
| nnnnnnnnnn | nnnnnnnnnn | nnnnnnnnnn | nnnnnnnnnn | nnnnnnnnnn | nnnnnnnnnn | 17460 |
| nnnnnnnnnn | nnnnnnnnnn | nnnnnnnnnn | nnnnnnnnnn | nnnnnnnnnn | nnnnnnnnnn | 17520 |
| nnnnnnnnnn | nnnnnnnnnn | nnnnnnnnnn | nnnnnnnnnn | nnnnnnnnnn | nnnnnnnnnn | 17580 |
| nnnnnnnnnn | nnnnnnnnnn | nnnnnnnnnn | nnnnnnnnnn | nnnnnnnnnn | nnnnnnnnnn | 17640 |

| | |
|---|---|
| nnnnnnnnnn nnnnnnnnnn nnnnnnnnnn nnnnnnnnnn nnnnnnnnnn nnnnnnnnnn | 17700 |
| nnnnnnnnnn nnnnnnnnnn nnnnnnnnnn nnnnnnnnnn nnnnnnnnnn nnnnnnnnnn | 17760 |
| nnnnnnnnnn nnnnnnnnnn nnnnnnnnnn nnnnnnnnnn nnnnnnnnnn nnnnnnnnnn | 17820 |
| nnnnnnnnnn nnnnnnnnnn nnnnnnnnnn nnnnnnnnnn nnnnnnnnnn nnnnnnnnnn | 17880 |
| nnnnnnnnnn nnnnnnnnnn nnnnnnnnnn nnnnnnnnnn nnnnnnnnnn nnnnnnnnnn | 17940 |
| nnnnnnnnnn nnnnnnnnnn nnnnnnnnnn nnnnnnnnnn nnnnnnnnnn nnnnnnnnnn | 18000 |
| nnnnnnnnnn nnnnnnnnnn nnnnnnnnnn nnnnnnnnnn nnnnnnnnnn nnnnnnnnnn | 18060 |
| nnnnnnnnnn nnnnnnnnnn nnnnnnnnnn nnnnnnnnnn nnnnnnnnnn nnnnnnnnnn | 18120 |
| nnnnnnnnnn nnnnnnnnnn nnnnnnnnnn nnnnnnnnnn nnnnnnnnnn nnnnnnnnnn | 18180 |
| nnnnnnnnnn nnnnnnnnnn nnnnnnnnnn nnnnnnnnnn nnnnnnnnnn nnnnnnnnnn | 18240 |
| nnnnnnnnnn nnnnnnnnnn nnnnnnnnnn nnnnnnnnnn nnnnnnnnnn nnnnnnnnnn | 18300 |
| nnnnnnnnnn nnnnnnnnnn nnnnnnnnnn nnnnnnnnnn nnnnnnnnnn nnnnnnnnnn | 18360 |
| nnnnnnnnnn nnnnnnnnnn nnnnnnnnnn nnnnnnnnnn nnnnnnnnnn nnnnnnnnnn | 18420 |
| nnnnnnnnnn nnnnnnnnnn nnnnnnnnnn nnnnnnnnnn nnnnnnnnnn nnnnnnnnnn | 18480 |
| nnnnnnnnnn nnnnnnnnnn nnnnnnnnnn nnnnnnnnnn nnnnnnnnnn nnnnnnnnnn | 18540 |
| nnnnnnnnnn nnnnnnnnnn nnnnnnnnnn nnnnnnnnnn nnnnnnnnnn nnnnnnnnnn | 18600 |
| nnnnnnnnnn nnnnnnnnnn nnnnnnnnnn nnnnnnnnnn nnnnnnnnnn nnnnnnnnnn | 18660 |
| nnnnnnnnnn nnnnnnnnnn nnnnnnnnnn nnnnnnnnnn nnnnnnnnnn nnnnnnnnnn | 18720 |
| nnnnnnnnnn nnnnnnnnnn nnnnnnnnnn nnnnnnnnnn nnnnnnnnnn nnnnnnnnnn | 18780 |
| nnnnnnnnnn nnnnnnnnnn nnnnnnnnnn nnnnnnnnnn nnnnnnnnnn nnnnnnnnnn | 18840 |
| nnnnnnnnnn nnnnnnnnnn nnnnnnnnnn nnnnnnnnnn nnnnnnnnnn nnnnnnnnnn | 18900 |
| nnnnnnnnnn nnnnnnnnnn nnnnnnnnnn nnnnnnnnnn nnnnnnnnnn nnnnnnnnnn | 18960 |
| nnnnnnnnnn nnnnnnnnnn nnnnnnnnnn nnnnnnnnnn nnnnnnnnnn nnnnnnnnnn | 19020 |
| nnnnnnnnnn nnnnnnnnnn nnnnnnnnnn nnnnnnnnnn nnnnnnnnnn nnnnnnnnnn | 19080 |
| nnnnnnnnnn nnnnnnnnnn nnnnnnnnnn nnnnnnnnnn nnnnnnnnnn nnnnnnnnnn | 19140 |
| nnnnnnnnnn nnnnnnnnnn nnnnnnnnnn nnnnnnnnnn nnnnnnnnnn nnnnnnnnnn | 19200 |
| nnnnnnnnnn nnnnnnnnnn nnnnnnnnnn nnnnnnnnnn nnnnnnnnnn nnnnnnnnnn | 19260 |
| nnnnnnnnnn nnnnnnnnnn nnnnnnnnnn nnnnnnnnnn nnnnnnnnnn nnnnnnnnnn | 19320 |
| nnnnnnnnnn nnnnnnnnnn nnnnnnnnnn nnnnnnnnnn nnnnnnnnnn nnnnnnnnnn | 19380 |
| nnnnnnnnnn nnnnnnnnnn nnnnnnnnnn nnnnnnnnnn nnnnnnnnnn nnnnnnnnnn | 19440 |
| nnnnnnnnnn nnnnnnnnnn nnnnnnnnnn nnnnnnnnnn nnnnnnnnnn nnnnnnnnnn | 19500 |
| nnnnnnnnnn nnnnnnnnnn nnnnnnnnnn nnnnnnnnnn nnnnnnnnnn nnnnnnnnnn | 19560 |
| nnnnnnnnnn nnnnnnnnnn nnnnnnnnnn nnnnnnnnnn nnnnnnnnnn nnnnnnnnnn | 19620 |
| nnnnnnnnnn nnnnnnnnnn nnnnnnnnnn nnnnnnnnnn nnnnnnnnnn nnnnnnnnnn | 19680 |
| nnnnnnnnnn nnnnnnnnnn nnnnnnnnnn nnnnnnnnnn nnnnnnnnnn nnnnnnnnnn | 19740 |
| nnnnnnnnnn nnnnnnnnnn nnnnnnnnnn nnnnnnnnnn nnnnnnnnnn nnnnnnnnnn | 19800 |
| nnnnnnnnnn nnnnnnnnnn nnnnnnnnnn nnnnnnnnnn nnnnnnnnnn nnnnnnnnnn | 19860 |
| nnnnnnnnnn nnnnnnnnnn nnnnnnnnnn nnnnnnnnnn nnnnnnnnnn nnnnnnnnnn | 19920 |
| nnnnnnnnnn nnnnnnnnnn nnnnnnnnnn nnnnnnnnnn nnnnnnnnnn nnnnnnnnnn | 19980 |
| nnnnnnnnnn nnnnnnnnnn nnnnnnnnnn nnnnnnnnnn nnnnnnnnnn nnnnnnnnnn | 20040 |

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 20100 |
| nnnnnnnnnn | nnnnnnnnnn | nnnnnnnnnn | nnnnnnnnnn | nnnnnnnnnn | nnnnnnnnnn | 20160 |
| nnnnnnnnnn | nnnnnnnnnn | nnnnnnnnnn | nnnnnnnnnn | nnnnnnnnnn | nnnnnnnnnn | 20220 |
| nnnnnnnnnn | nnnnnnnnnn | nnnnnnnnnn | nnnnnnnnnn | nnnnnnnnnn | nnnnnnnnnn | 20280 |
| nnnnnnnnnn | nnnnnnnnnn | nnnnnnnnnn | nnnnnnnnnn | nnnnnnnnnn | nnnnnnnnnn | 20340 |
| nnnnnnnnnn | nnnnnnnnnn | nnnnnnnnnn | nnnnnnnnnn | nnnnnnnnnn | nnnnnnnnnn | 20400 |
| nnnnnnnnnn | nnnnnnnnnn | nnnnnnnnnn | nnnnnnnnnn | nnnnnnnnnn | nnnnnnnnnn | 20460 |
| nnnnnnnnnn | nnnnnnnnnn | nnnnnnnnnn | nnnnnnnnnn | nnnnnnnnnn | nnnnnnnnnn | 20520 |
| nnnnnnnnnn | nnnnnnnnnn | nnnnnnnnnn | nnnnnnnnnn | nnnnnnnnnn | nnnnnnnnnn | 20580 |
| nnnnnnnnnn | nnnnnnnnnn | nnnnnnnnnn | nnnnnnnnnn | nnnnnnnnnn | nnnnnnnnnn | 20640 |
| nnnnnnnnnn | nnnnnnnnnn | nnnnnnnnnn | nnnnnnnnnn | nnnnnnnnnn | nnnnnnnnnn | 20700 |
| nnnnnnnnnn | nnnnnnnnnn | nnnnnnnnnn | nnnnnnnnnn | nnnnnnnnnn | nnnnnnnnnn | 20760 |
| nnnnnnnnnn | nnnnnnnnnn | nnnnnnnnnn | nnnnnnnnnn | nnnnnnnnnn | nnnnnnnnnn | 20820 |
| nnnnnnnnnn | nnnnnnnnnn | nnnnnnnnnn | nnnnnnnnnn | nnnnnnnnnn | nnnnnnnnnn | 20880 |
| nnnnnnnnnn | nnnnnnnnnn | nnnnnnnnnn | nnnnnnnnnn | nnnnnnnnnn | nnnnnnnnnn | 20940 |
| nnnnnnnnnn | nnnnnnnnnn | nnnnnnnnnn | nnnnnnnnnn | nnnnnnnnnn | nnnnnnnnnn | 21000 |
| nnnnnnnnnn | nnnnnnnnnn | nnnnnnnnnn | nnnnnnnnnn | nnnnnnnnnn | nnnnnnnnnn | 21060 |
| nnnnnnnnnn | nnnnnnnnnn | nnnnnnnnnn | nnnnnnnnnn | nnnnnnnnnn | nnnnnnnnnn | 21120 |
| nnnnnnnnnn | nnnnnnnnnn | nnnnnnnnnn | nnnnnnnnnn | nnnnnnnnnn | nnnnnnnnnn | 21180 |
| nnnnnnnnnn | nnnnnnnnnn | nnnnnnnnnn | nnnnnnnnnn | nnnnnnnnnn | nnnnnnnnnn | 21240 |
| nnnnnnnnnn | nnnnnnnnnn | nnnnnnnnnn | nnnnnnnnnn | nnnnnnnnnn | nnnnnnnnnn | 21300 |
| nnnnnnnnnn | naaaa | | | | | 21315 |

```
<210> SEQ ID NO 13
<211> LENGTH: 1158
<212> TYPE: RNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (1)..(30)
<223> OTHER INFORMATION: n is a, c, g, or u
<220> FEATURE:
<221> NAME/KEY: misc_feature
<222> LOCATION: (47)..(78)
<223> OTHER INFORMATION: n is a, c, g, or u
<220> FEATURE:
<221> NAME/KEY: misc_feature
<222> LOCATION: (79)..(97)
<223> OTHER INFORMATION: 3' splice site (very strong)
<220> FEATURE:
<221> NAME/KEY: misc_feature
<222> LOCATION: (98)..(129)
<223> OTHER INFORMATION: n is a, c, g, or u
<220> FEATURE:
<221> NAME/KEY: misc_feature
<222> LOCATION: (136)..(1116)
<223> OTHER INFORMATION: n is a, c, g, or u
<220> FEATURE:
<221> NAME/KEY: misc_feature
<222> LOCATION: (1123)..(1154)
<223> OTHER INFORMATION: n is a, c, g, or u
<220> FEATURE:
<221> NAME/KEY: misc_feature
<222> LOCATION: (1155)..(1158)
<223> OTHER INFORMATION: poly A sequence
```

<400> SEQUENCE: 13

```
nnnnnnnnnn nnnnnnnnnn nnnnnnnnnn uauggaagcu ggaaggnnnn nnnnnnnnnn      60
nnnnnnnnnn nnnnnnnnuu cuuucucucu uucagcunnn nnnnnnnnnn nnnnnnnnnn     120
nnnnnnnnng cuucunnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnnnnnnnnn nnnnnnnnnn nnnnnnnnnn    1020
nnnnnnnnnn nnnnnnnnnn nnnnnnnnnn nnnnnnnnnn nnnnnnnnnn nnnnnnnnnn    1080
nnnnnnnnnn nnnnnnnnnn nnnnnnnnnn nnnnnnguuu agnnnnnnnn nnnnnnnnnn    1140
nnnnnnnnnn nnnnaaaa                                                  1158
```

<210> SEQ ID NO 14
<211> LENGTH: 1126
<212> TYPE: RNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (1)..(4)
<223> OTHER INFORMATION: n is a, c, g, or u
<220> FEATURE:
<221> NAME/KEY: misc_feature
<222> LOCATION: (14)..(75)
<223> OTHER INFORMATION: n is a, c, g, or u
<220> FEATURE:
<221> NAME/KEY: misc_feature
<222> LOCATION: (82)..(113)
<223> OTHER INFORMATION: n is a, c, g, or u
<220> FEATURE:
<221> NAME/KEY: misc_feature
<222> LOCATION: (120)..(1116)
<223> OTHER INFORMATION: n is a, c, g, or u
<220> FEATURE:
<221> NAME/KEY: misc_feature
<222> LOCATION: (1123)..(1126)
<223> OTHER INFORMATION: poly A sequence

<400> SEQUENCE: 14

```
nnnnaacaug aagnnnnnnn nnnnnnnnnn nnnnnnnnnn nnnnnnnnnn nnnnnnnnnn      60
nnnnnnnnnn nnnnnauagc unnnnnnnnn nnnnnnnnnn nnnnnnnnnn nnngcuucun     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
```

```
nnnnnnnnnn nnnnnnnnnn nnnnnnnnnn nnnnnnnnnn nnnnnnnnnn nnnnnnnnnn      300
nnnnnnnnnn nnnnnnnnnn nnnnnnnnnn nnnnnnnnnn nnnnnnnnnn nnnnnnnnnn      360
nnnnnnnnnn nnnnnnnnnn nnnnnnnnnn nnnnnnnnnn nnnnnnnnnn nnnnnnnnnn      420
nnnnnnnnnn nnnnnnnnnn nnnnnnnnnn nnnnnnnnnn nnnnnnnnnn nnnnnnnnnn      480
nnnnnnnnnn nnnnnnnnnn nnnnnnnnnn nnnnnnnnnn nnnnnnnnnn nnnnnnnnnn      540
nnnnnnnnnn nnnnnnnnnn nnnnnnnnnn nnnnnnnnnn nnnnnnnnnn nnnnnnnnnn      600
nnnnnnnnnn nnnnnnnnnn nnnnnnnnnn nnnnnnnnnn nnnnnnnnnn nnnnnnnnnn      660
nnnnnnnnnn nnnnnnnnnn nnnnnnnnnn nnnnnnnnnn nnnnnnnnnn nnnnnnnnnn      720
nnnnnnnnnn nnnnnnnnnn nnnnnnnnnn nnnnnnnnnn nnnnnnnnnn nnnnnnnnnn      780
nnnnnnnnnn nnnnnnnnnn nnnnnnnnnn nnnnnnnnnn nnnnnnnnnn nnnnnnnnnn      840
nnnnnnnnnn nnnnnnnnnn nnnnnnnnnn nnnnnnnnnn nnnnnnnnnn nnnnnnnnnn      900
nnnnnnnnnn nnnnnnnnnn nnnnnnnnnn nnnnnnnnnn nnnnnnnnnn nnnnnnnnnn      960
nnnnnnnnnn nnnnnnnnnn nnnnnnnnnn nnnnnnnnnn nnnnnnnnnn nnnnnnnnnn     1020
nnnnnnnnnn nnnnnnnnnn nnnnnnnnnn nnnnnnnnnn nnnnnnnnnn nnnnnnnnnn     1080
nnnnnnnnnn nnnnnnnnnn nnnnnnnnnn nnnnnnguuu agaaaa                    1126
```

<210> SEQ ID NO 15
<211> LENGTH: 28
<212> TYPE: RNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (1)..(28)
<223> OTHER INFORMATION: poly A sequence

<400> SEQUENCE: 15

```
aaaaaaaaaa aaaaaaaaaa aaaaaaaa                                          28
```

<210> SEQ ID NO 16
<211> LENGTH: 52
<212> TYPE: RNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (2)..(20)
<223> OTHER INFORMATION: poly U sequence
<220> FEATURE:
<221> NAME/KEY: misc_feature
<222> LOCATION: (40)..(40)
<223> OTHER INFORMATION: n is a, c, g, or u
<220> FEATURE:
<221> NAME/KEY: misc_feature
<222> LOCATION: (44)..(52)
<223> OTHER INFORMATION: poly A sequence

<400> SEQUENCE: 16

```
nuuuuuuuuu uuuuuuuuuu uuuuuuuccc uuuuuuuccn cagaaaaaaa aa              52
```

<210> SEQ ID NO 17
<211> LENGTH: 18
<212> TYPE: RNA

```
<213> ORGANISM: Artificial Sequence
<220> FEATURE:
<223> OTHER INFORMATION: artificially synthesized
<220> FEATURE:
<221> NAME/KEY: misc_feature
<222> LOCATION: (10)..(18)
<223> OTHER INFORMATION: poly A sequence

<400> SEQUENCE: 17
aagguaagua aaaaaaaa                                                   18

<210> SEQ ID NO 18
<211> LENGTH: 24
<212> TYPE: RNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (2)..(24)
<223> OTHER INFORMATION: poly U/C sequence
<220> FEATURE:
<221> NAME/KEY: misc_feature
<222> LOCATION: (21)..(21)
<223> OTHER INFORMATION: n is a, c, g, or u

<400> SEQUENCE: 18
nuuuuuuucc cuuuuuuucc ncag                                            24

<210> SEQ ID NO 19
<211> LENGTH: 124
<212> TYPE: RNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (2)..(16)
<223> OTHER INFORMATION: poly U sequence
<220> FEATURE:
<221> NAME/KEY: misc_feature
<222> LOCATION: (17)..(47)
<223> OTHER INFORMATION: n is a, c, g, or u
<220> FEATURE:
<221> NAME/KEY: misc_feature
<222> LOCATION: (66)..(87)
<223> OTHER INFORMATION: n is a, c, g, or u
<220> FEATURE:
<221> NAME/KEY: misc_feature
<222> LOCATION: (97)..(118)
<223> OTHER INFORMATION: n is a, c, g, or u
<220> FEATURE:
<221> NAME/KEY: misc_feature
<222> LOCATION: (119)..(124)
<223> OTHER INFORMATION: poly A sequence

<400> SEQUENCE: 19
nuuuuuuuuu uuuuuunnnn nnnnnnnnnn nnnnnnnaga agaacggaag               60
aacaannnnn nnnnnnnnnn nnnnnnnaag guuagunnnn nnnnnnnnnn nnnnnnnnaa    120
aaaa                                                                  124

<210> SEQ ID NO 20
<211> LENGTH: 2517
```

<212> TYPE: RNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (1)..(1000)
<223> OTHER INFORMATION: n is a, c, g, or u
<220> FEATURE:
<221> NAME/KEY: misc_feature
<222> LOCATION: (1002)..(1008)
<223> OTHER INFORMATION: n is a, c, g, or u
<220> FEATURE:
<221> NAME/KEY: misc_feature
<222> LOCATION: (1011)..(1503)
<223> OTHER INFORMATION: n is a, c, g, or u
<220> FEATURE:
<221> NAME/KEY: misc_feature
<222> LOCATION: (1508)..(2500)
<223> OTHER INFORMATION: n is a, c, g, or u
<220> FEATURE:
<221> NAME/KEY: misc_feature
<222> LOCATION: (2501)..(2517)
<223> OTHER INFORMATION: poly A sequence

<400> SEQUENCE: 20

```
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnnnnnnnnn annnnnnnag nnnnnnnnnn    1020
nnnnnnnnnn nnnnnnnnnn nnnnnnnnnn nnnnnnnnnn nnnnnnnnnn nnnnnnnnnn    1080
nnnnnnnnnn nnnnnnnnnn nnnnnnnnnn nnnnnnnnnn nnnnnnnnnn nnnnnnnnnn    1140
nnnnnnnnnn nnnnnnnnnn nnnnnnnnnn nnnnnnnnnn nnnnnnnnnn nnnnnnnnnn    1200
nnnnnnnnnn nnnnnnnnnn nnnnnnnnnn nnnnnnnnnn nnnnnnnnnn nnnnnnnnnn    1260
nnnnnnnnnn nnnnnnnnnn nnnnnnnnnn nnnnnnnnnn nnnnnnnnnn nnnnnnnnnn    1320
nnnnnnnnnn nnnnnnnnnn nnnnnnnnnn nnnnnnnnnn nnnnnnnnnn nnnnnnnnnn    1380
nnnnnnnnnn nnnnnnnnnn nnnnnnnnnn nnnnnnnnnn nnnnnnnnnn nnnnnnnnnn    1440
nnnnnnnnnn nnnnnnnnnn nnnnnnnnnn nnnnnnnnnn nnnnnnnnnn nnnnnnnnnn    1500
nnncaugnnn nnnnnnnnnn nnnnnnnnnn nnnnnnnnnn nnnnnnnnnn nnnnnnnnnn    1560
```

```
nnnnnnnnnn nnnnnnnnnn nnnnnnnnnn nnnnnnnnnn nnnnnnnnnn nnnnnnnnnn    1620
nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnnn nnnnnnnnnn nnnnnnnnnn nnnnnnnnnn    1740
nnnnnnnnnn nnnnnnnnnn nnnnnnnnnn nnnnnnnnnn nnnnnnnnnn nnnnnnnnnn    1800
nnnnnnnnnn nnnnnnnnnn nnnnnnnnnn nnnnnnnnnn nnnnnnnnnn nnnnnnnnnn    1860
nnnnnnnnnn nnnnnnnnnn nnnnnnnnnn nnnnnnnnnn nnnnnnnnnn nnnnnnnnnn    1920
nnnnnnnnnn nnnnnnnnnn nnnnnnnnnn nnnnnnnnnn nnnnnnnnnn nnnnnnnnnn    1980
nnnnnnnnnn nnnnnnnnnn nnnnnnnnnn nnnnnnnnnn nnnnnnnnnn nnnnnnnnnn    2040
nnnnnnnnnn nnnnnnnnnn nnnnnnnnnn nnnnnnnnnn nnnnnnnnnn nnnnnnnnnn    2100
nnnnnnnnnn nnnnnnnnnn nnnnnnnnnn nnnnnnnnnn nnnnnnnnnn nnnnnnnnnn    2160
nnnnnnnnnn nnnnnnnnnn nnnnnnnnnn nnnnnnnnnn nnnnnnnnnn nnnnnnnnnn    2220
nnnnnnnnnn nnnnnnnnnn nnnnnnnnnn nnnnnnnnnn nnnnnnnnnn nnnnnnnnnn    2280
nnnnnnnnnn nnnnnnnnnn nnnnnnnnnn nnnnnnnnnn nnnnnnnnnn nnnnnnnnnn    2340
nnnnnnnnnn nnnnnnnnnn nnnnnnnnnn nnnnnnnnnn nnnnnnnnnn nnnnnnnnnn    2400
nnnnnnnnnn nnnnnnnnnn nnnnnnnnnn nnnnnnnnnn nnnnnnnnnn nnnnnnnnnn    2460
nnnnnnnnnn nnnnnnnnnn nnnnnnnnnn nnnnnnnnnn aaaaaaaaaa aaaaaaa       2517

<210> SEQ ID NO 21
<211> LENGTH: 1113
<212> TYPE: RNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (2)..(19)
<223> OTHER INFORMATION: poly U sequence
<220> FEATURE:
<221> NAME/KEY: misc_feature
<222> LOCATION: (20)..(51)
<223> OTHER INFORMATION: n is a, c, g, or u
<220> FEATURE:
<221> NAME/KEY: misc_feature
<222> LOCATION: (70)..(101)
<223> OTHER INFORMATION: n is a, c, g, or u
<220> FEATURE:
<221> NAME/KEY: misc_feature
<222> LOCATION: (104)..(105)
<223> OTHER INFORMATION: splice junction
<220> FEATURE:
<221> NAME/KEY: misc_feature
<222> LOCATION: (105)..(1096)
<223> OTHER INFORMATION: n is a, c, g, or u
<220> FEATURE:
<221> NAME/KEY: misc_feature
<222> LOCATION: (1097)..(1113)
<223> OTHER INFORMATION: poly A sequence

<400> SEQUENCE: 21
nuuuuuuuuu uuuuuuuuun nnnnnnnnnn nnnnnnnnnn nnnnnnnnnn nagaagaacg      60
gaagaacaan nnnnnnnnnn nnnnnnnnnn nnnnnnnnnn naagnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
```

```
nnnnnnnnnn nnnnnnnnnn nnnnnnnnnn nnnnnnnnnn nnnnnnnnnn nnnnnnnnnn      360
nnnnnnnnnn nnnnnnnnnn nnnnnnnnnn nnnnnnnnnn nnnnnnnnnn nnnnnnnnnn      420
nnnnnnnnnn nnnnnnnnnn nnnnnnnnnn nnnnnnnnnn nnnnnnnnnn nnnnnnnnnn      480
nnnnnnnnnn nnnnnnnnnn nnnnnnnnnn nnnnnnnnnn nnnnnnnnnn nnnnnnnnnn      540
nnnnnnnnnn nnnnnnnnnn nnnnnnnnnn nnnnnnnnnn nnnnnnnnnn nnnnnnnnnn      600
nnnnnnnnnn nnnnnnnnnn nnnnnnnnnn nnnnnnnnnn nnnnnnnnnn nnnnnnnnnn      660
nnnnnnnnnn nnnnnnnnnn nnnnnnnnnn nnnnnnnnnn nnnnnnnnnn nnnnnnnnnn      720
nnnnnnnnnn nnnnnnnnnn nnnnnnnnnn nnnnnnnnnn nnnnnnnnnn nnnnnnnnnn      780
nnnnnnnnnn nnnnnnnnnn nnnnnnnnnn nnnnnnnnnn nnnnnnnnnn nnnnnnnnnn      840
nnnnnnnnnn nnnnnnnnnn nnnnnnnnnn nnnnnnnnnn nnnnnnnnnn nnnnnnnnnn      900
nnnnnnnnnn nnnnnnnnnn nnnnnnnnnn nnnnnnnnnn nnnnnnnnnn nnnnnnnnnn      960
nnnnnnnnnn nnnnnnnnnn nnnnnnnnnn nnnnnnnnnn nnnnnnnnnn nnnnnnnnnn     1020
nnnnnnnnnn nnnnnnnnnn nnnnnnnnnn nnnnnnnnnn nnnnnnnnnn nnnnnnnnnn     1080
nnnnnnnnnn nnnnnnaaaa aaaaaaaaaa aaa                                   1113

<210> SEQ ID NO 22
<211> LENGTH: 1078
<212> TYPE: DNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (19)..(33)
<223> OTHER INFORMATION: poly T sequence
<220> FEATURE:
<221> NAME/KEY: misc_feature
<222> LOCATION: (34)..(1025)
<223> OTHER INFORMATION: n is a, c, g, or t
<220> FEATURE:
<221> NAME/KEY: misc_feature
<222> LOCATION: (1029)..(1060)
<223> OTHER INFORMATION: n is a, c, g, or t

<400> SEQUENCE: 22
aaccttccaa ccggccaatt ttttttttttt tttnnnnnnn nnnnnnnnnn nnnnnnnnnn       60
nnnnnnnnnn nnnnnnnnnn nnnnnnnnnn nnnnnnnnnn nnnnnnnnnn nnnnnnnnnn      120
nnnnnnnnnn nnnnnnnnnn nnnnnnnnnn nnnnnnnnnn nnnnnnnnnn nnnnnnnnnn      180
nnnnnnnnnn nnnnnnnnnn nnnnnnnnnn nnnnnnnnnn nnnnnnnnnn nnnnnnnnnn      240
nnnnnnnnnn nnnnnnnnnn nnnnnnnnnn nnnnnnnnnn nnnnnnnnnn nnnnnnnnnn      300
nnnnnnnnnn nnnnnnnnnn nnnnnnnnnn nnnnnnnnnn nnnnnnnnnn nnnnnnnnnn      360
nnnnnnnnnn nnnnnnnnnn nnnnnnnnnn nnnnnnnnnn nnnnnnnnnn nnnnnnnnnn      420
nnnnnnnnnn nnnnnnnnnn nnnnnnnnnn nnnnnnnnnn nnnnnnnnnn nnnnnnnnnn      480
nnnnnnnnnn nnnnnnnnnn nnnnnnnnnn nnnnnnnnnn nnnnnnnnnn nnnnnnnnnn      540
nnnnnnnnnn nnnnnnnnnn nnnnnnnnnn nnnnnnnnnn nnnnnnnnnn nnnnnnnnnn      600
nnnnnnnnnn nnnnnnnnnn nnnnnnnnnn nnnnnnnnnn nnnnnnnnnn nnnnnnnnnn      660
nnnnnnnnnn nnnnnnnnnn nnnnnnnnnn nnnnnnnnnn nnnnnnnnnn nnnnnnnnnn      720
nnnnnnnnnn nnnnnnnnnn nnnnnnnnnn nnnnnnnnnn nnnnnnnnnn nnnnnnnnnn      780
nnnnnnnnnn nnnnnnnnnn nnnnnnnnnn nnnnnnnnnn nnnnnnnnnn nnnnnnnnnn      840
```

```
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn nnnnnnnnnn nnnnnnnnnn   1020
nnnnncttnn nnnnnnnnnn nnnnnnnnnn nnnnnnnnnn ttgttcttcc gttcttct     1078
```

<210> SEQ ID NO 23
<211> LENGTH: 33
<212> TYPE: DNA
<213> ORGANISM: Artificial Sequence
<220> FEATURE:
<223> OTHER INFORMATION: artificially synthesized primer

<400> SEQUENCE: 23

```
aaccggccaa ccggccaatt tttttttttt ttt                                  33
```

<210> SEQ ID NO 24
<211> LENGTH: 1078
<212> TYPE: DNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (19)..(33)
<223> OTHER INFORMATION: poly T sequence
<220> FEATURE:
<221> NAME/KEY: misc_feature
<222> LOCATION: (34)..(1025)
<223> OTHER INFORMATION: n is a, c, g, or t
<220> FEATURE:
<221> NAME/KEY: misc_feature
<222> LOCATION: (1029)..(1060)
<223> OTHER INFORMATION: n is a, c, g, or t

<400> SEQUENCE: 24

```
aaccttccaa ccggccaatt tttttttttt tttnnnnnnn nnnnnnnnnn nnnnnnnnnn     60
nnnnnnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn nnnnnnnnnn nnnnnnnnnn nnnnnnnnnn nnnnnnnnnn    240
nnnnnnnnnn nnnnnnnnnn nnnnnnnnnn nnnnnnnnnn nnnnnnnnnn nnnnnnnnnn    300
nnnnnnnnnn nnnnnnnnnn nnnnnnnnnn nnnnnnnnnn nnnnnnnnnn nnnnnnnnnn    360
nnnnnnnnnn nnnnnnnnnn nnnnnnnnnn nnnnnnnnnn nnnnnnnnnn nnnnnnnnnn    420
nnnnnnnnnn nnnnnnnnnn nnnnnnnnnn nnnnnnnnnn nnnnnnnnnn nnnnnnnnnn    480
nnnnnnnnnn nnnnnnnnnn nnnnnnnnnn nnnnnnnnnn nnnnnnnnnn nnnnnnnnnn    540
nnnnnnnnnn nnnnnnnnnn nnnnnnnnnn nnnnnnnnnn nnnnnnnnnn nnnnnnnnnn    600
nnnnnnnnnn nnnnnnnnnn nnnnnnnnnn nnnnnnnnnn nnnnnnnnnn nnnnnnnnnn    660
nnnnnnnnnn nnnnnnnnnn nnnnnnnnnn nnnnnnnnnn nnnnnnnnnn nnnnnnnnnn    720
nnnnnnnnnn nnnnnnnnnn nnnnnnnnnn nnnnnnnnnn nnnnnnnnnn nnnnnnnnnn    780
nnnnnnnnnn nnnnnnnnnn nnnnnnnnnn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn nnnnnnnnnn nnnnnnnnnn   1020
nnnnncttnn nnnnnnnnnn nnnnnnnnnn nnnnnnnnnn ttgttcttcc gttcttct     1078
```

```
<210> SEQ ID NO 25
<211> LENGTH: 18
<212> TYPE: DNA
<213> ORGANISM: Artificial Sequence
<220> FEATURE:
<223> OTHER INFORMATION: artificially synthesized primer

<400> SEQUENCE: 25
agaagaacgg aagaacaa                                                   18

<210> SEQ ID NO 26
<211> LENGTH: 1078
<212> TYPE: DNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (19)..(50)
<223> OTHER INFORMATION: n is a, c, g, or t
<220> FEATURE:
<221> NAME/KEY: misc_feature
<222> LOCATION: (54)..(1045)
<223> OTHER INFORMATION: n is a, c, g, or t
<220> FEATURE:
<221> NAME/KEY: misc_feature
<222> LOCATION: (1046)..(1060)
<223> OTHER INFORMATION: poly A sequence

<400> SEQUENCE: 26
agaagaacgg aagaacaann nnnnnnnnnn nnnnnnnnnn nnnnnnnnnn aagnnnnnnn      60
nnnnnnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn nnnnnnnnnn nnnnnnnnnn nnnnnnnnnn nnnnnnnnnn    240
nnnnnnnnnn nnnnnnnnnn nnnnnnnnnn nnnnnnnnnn nnnnnnnnnn nnnnnnnnnn    300
nnnnnnnnnn nnnnnnnnnn nnnnnnnnnn nnnnnnnnnn nnnnnnnnnn nnnnnnnnnn    360
nnnnnnnnnn nnnnnnnnnn nnnnnnnnnn nnnnnnnnnn nnnnnnnnnn nnnnnnnnnn    420
nnnnnnnnnn nnnnnnnnnn nnnnnnnnnn nnnnnnnnnn nnnnnnnnnn nnnnnnnnnn    480
nnnnnnnnnn nnnnnnnnnn nnnnnnnnnn nnnnnnnnnn nnnnnnnnnn nnnnnnnnnn    540
nnnnnnnnnn nnnnnnnnnn nnnnnnnnnn nnnnnnnnnn nnnnnnnnnn nnnnnnnnnn    600
nnnnnnnnnn nnnnnnnnnn nnnnnnnnnn nnnnnnnnnn nnnnnnnnnn nnnnnnnnnn    660
nnnnnnnnnn nnnnnnnnnn nnnnnnnnnn nnnnnnnnnn nnnnnnnnnn nnnnnnnnnn    720
nnnnnnnnnn nnnnnnnnnn nnnnnnnnnn nnnnnnnnnn nnnnnnnnnn nnnnnnnnnn    780
nnnnnnnnnn nnnnnnnnnn nnnnnnnnnn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn nnnnnnnnnn nnnnnnnnnn   1020
nnnnnnnnnn nnnnnnnnnn nnnnnaaaaa aaaaaaaaaa ttggccggtt ggaaggtt      1078

<210> SEQ ID NO 27
<211> LENGTH: 18
<212> TYPE: DNA
<213> ORGANISM: Artificial Sequence
<220> FEATURE:
<223> OTHER INFORMATION: artificially synthesized primer

<400> SEQUENCE: 27
```
aaccttccaa ccggccaa                                                       18

<210> SEQ ID NO 28
<211> LENGTH: 164
<212> TYPE: DNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (19)..(50)
<223> OTHER INFORMATION: n is a, c, g, or t
<220> FEATURE:
<221> NAME/KEY: misc_feature
<222> LOCATION: (60)..(91)
<223> OTHER INFORMATION: n is a, c, g, or t
<220> FEATURE:
<221> NAME/KEY: misc_feature
<222> LOCATION: (95)..(96)
<223> OTHER INFORMATION: splice site
<220> FEATURE:
<221> NAME/KEY: misc_feature
<222> LOCATION: (95)..(96)
<223> OTHER INFORMATION: cleavage site
<220> FEATURE:
<221> NAME/KEY: misc_feature
<222> LOCATION: (100)..(131)
<223> OTHER INFORMATION: n is a, c, g, or t
<220> FEATURE:
<221> NAME/KEY: misc_feature
<222> LOCATION: (132)..(146)
<223> OTHER INFORMATION: poly T sequence

<400> SEQUENCE: 28
tcttcttgcc ttcttgttnn nnnnnnnnnn nnnnnnnnnn nnnnnnnnnn ttccaatcan     60
nnnnnnnnnn nnnnnnnnnn nnnnnnnnnn ntaaatttan nnnnnnnnnn nnnnnnnnnn    120
nnnnnnnnnn nttttttttt tttttttaacc ggccaacctt ccaa                    164

<210> SEQ ID NO 29
<211> LENGTH: 164
<212> TYPE: DNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (19)..(50)
<223> OTHER INFORMATION: n is a, c, g, or t
<220> FEATURE:
<221> NAME/KEY: misc_feature
<222> LOCATION: (60)..(91)
<223> OTHER INFORMATION: n is a, c, g, or t
<220> FEATURE:
<221> NAME/KEY: misc_feature
<222> LOCATION: (95)..(96)
<223> OTHER INFORMATION: splice site
<220> FEATURE:
<221> NAME/KEY: misc_feature
<222> LOCATION: (95)..(96)
<223> OTHER INFORMATION: cleavage site
<220> FEATURE:
<221> NAME/KEY: misc_feature
<222> LOCATION: (100)..(131)
<223> OTHER INFORMATION: n is a, c, g, or t
<220> FEATURE:
<221> NAME/KEY: misc_feature
<222> LOCATION: (132)..(146)
<223> OTHER INFORMATION: poly A sequence

<400> SEQUENCE: 29
agaagaacgg aagaacaann nnnnnnnnnn nnnnnnnnnn nnnnnnnnnn aaggttagtn     60
nnnnnnnnnn nnnnnnnnnn nnnnnnnnnn natttaaatn nnnnnnnnnn nnnnnnnnnn    120
nnnnnnnnnn naaaaaaaaa aaaaaattgg ccggttggaa ggtt        164

<210> SEQ ID NO 30
<211> LENGTH: 95
<212> TYPE: DNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (19)..(50)
<223> OTHER INFORMATION: n is a, c, g, or t
<220> FEATURE:
<221> NAME/KEY: misc_feature
<222> LOCATION: (60)..(91)
<223> OTHER INFORMATION: n is a, c, g, or t

<400> SEQUENCE: 30
tcttcttgcc ttcttgttnn nnnnnnnnnn nnnnnnnnnn nnnnnnnnnn ttccaatcan        60
nnnnnnnnnn nnnnnnnnnn nnnnnnnnnn ntaaa        95

<210> SEQ ID NO 31
<211> LENGTH: 69
<212> TYPE: DNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (5)..(36)
<223> OTHER INFORMATION: n is a, c, g, or t
<220> FEATURE:
<221> NAME/KEY: misc_feature
<222> LOCATION: (37)..(51)
<223> OTHER INFORMATION: poly T sequence

<400> SEQUENCE: 31
tttannnnnn nnnnnnnnnn nnnnnnnnnn nnnnntttt tttttttttt taaccggcca        60
accttccaa        69

<210> SEQ ID NO 32
<211> LENGTH: 95
<212> TYPE: DNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (19)..(50)
<223> OTHER INFORMATION: n is a, c, g, or t
<220> FEATURE:
<221> NAME/KEY: misc_feature
<222> LOCATION: (60)..(91)
<223> OTHER INFORMATION: n is a, c, g, or t

<400> SEQUENCE: 32
agaagaacgg aagaacaann nnnnnnnnnn nnnnnnnnnn nnnnnnnnnn aaggttagtn        60
nnnnnnnnnn nnnnnnnnnn nnnnnnnnnn nattt        95

<210> SEQ ID NO 33
<211> LENGTH: 69
<212> TYPE: DNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (5)..(36)

```
<223> OTHER INFORMATION: n is a, c, g, or t
<220> FEATURE:
<221> NAME/KEY: misc_feature
<222> LOCATION: (37)..(51)
<223> OTHER INFORMATION: poly A sequence

<400> SEQUENCE: 33
aaatnnnnnn nnnnnnnnnn nnnnnnnnnn nnnnnnaaaa aaaaaaaaaa attggccggt    60
tggaaggtt                                                            69

<210> SEQ ID NO 34
<211> LENGTH: 205
<212> TYPE: RNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (2)..(18)
<223> OTHER INFORMATION: poly U sequence
<220> FEATURE:
<221> NAME/KEY: misc_feature
<222> LOCATION: (19)..(50)
<223> OTHER INFORMATION: n is a, c, g, or u
<220> FEATURE:
<221> NAME/KEY: misc_feature
<222> LOCATION: (64)..(64)
<223> OTHER INFORMATION: branch A site
<220> FEATURE:
<221> NAME/KEY: misc_feature
<222> LOCATION: (67)..(88)
<223> OTHER INFORMATION: n is a, c, g, or u
<220> FEATURE:
<221> NAME/KEY: misc_feature
<222> LOCATION: (106)..(106)
<223> OTHER INFORMATION: n is a, c, g, or u
<220> FEATURE:
<221> NAME/KEY: misc_feature
<222> LOCATION: (109)..(110)
<223> OTHER INFORMATION: splice site
<220> FEATURE:
<221> NAME/KEY: misc_feature
<222> LOCATION: (129)..(190)
<223> OTHER INFORMATION: n is a, c, g, or u
<220> FEATURE:
<221> NAME/KEY: misc_feature
<222> LOCATION: (191)..(205)
<223> OTHER INFORMATION: poly A sequence

<400> SEQUENCE: 34
nuuuuuuuuu uuuuuuuunn nnnnnnnnnn nnnnnnnnnn nnnnnnnnnn auuuaaauua    60
cuaacannnn nnnnnnnnnn nnnnnnnnuu uuucccuuuu uuuccncaga gaagaacgga   120
agaacaagnn nnnnnnnnnn nnnnnnnnnn nnnnnnnnnn nnnnnnnnnn nnnnnnnnnn   180
nnnnnnnnnn aaaaaaaaaa aaaaa                                         205

<210> SEQ ID NO 35
<211> LENGTH: 2011
<212> TYPE: RNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (1)..(993)
<223> OTHER INFORMATION: n is a, c, g, or u
<220> FEATURE:
<221> NAME/KEY: misc_feature
```

<222> LOCATION: (996)..(997)
<223> OTHER INFORMATION: splice site
<220> FEATURE:
<221> NAME/KEY: misc_feature
<222> LOCATION: (1003)..(1994)
<223> OTHER INFORMATION: n is a, c, g, or u
<220> FEATURE:
<221> NAME/KEY: misc_feature
<222> LOCATION: (1995)..(2011)
<223> OTHER INFORMATION: poly A sequence

<400> SEQUENCE: 35

```
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnngagguga gunnnnnnnn nnnnnnnnnn    1020
nnnnnnnnnn nnnnnnnnnn nnnnnnnnnn nnnnnnnnnn nnnnnnnnnn nnnnnnnnnn    1080
nnnnnnnnnn nnnnnnnnnn nnnnnnnnnn nnnnnnnnnn nnnnnnnnnn nnnnnnnnnn    1140
nnnnnnnnnn nnnnnnnnnn nnnnnnnnnn nnnnnnnnnn nnnnnnnnnn nnnnnnnnnn    1200
nnnnnnnnnn nnnnnnnnnn nnnnnnnnnn nnnnnnnnnn nnnnnnnnnn nnnnnnnnnn    1260
nnnnnnnnnn nnnnnnnnnn nnnnnnnnnn nnnnnnnnnn nnnnnnnnnn nnnnnnnnnn    1320
nnnnnnnnnn nnnnnnnnnn nnnnnnnnnn nnnnnnnnnn nnnnnnnnnn nnnnnnnnnn    1380
nnnnnnnnnn nnnnnnnnnn nnnnnnnnnn nnnnnnnnnn nnnnnnnnnn nnnnnnnnnn    1440
nnnnnnnnnn nnnnnnnnnn nnnnnnnnnn nnnnnnnnnn nnnnnnnnnn nnnnnnnnnn    1500
nnnnnnnnnn nnnnnnnnnn nnnnnnnnnn nnnnnnnnnn nnnnnnnnnn nnnnnnnnnn    1560
nnnnnnnnnn nnnnnnnnnn nnnnnnnnnn nnnnnnnnnn nnnnnnnnnn nnnnnnnnnn    1620
nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnnn nnnnnnnnnn nnnnnnnnnn nnnnnnnnnn    1740
nnnnnnnnnn nnnnnnnnnn nnnnnnnnnn nnnnnnnnnn nnnnnnnnnn nnnnnnnnnn    1800
nnnnnnnnnn nnnnnnnnnn nnnnnnnnnn nnnnnnnnnn nnnnnnnnnn nnnnnnnnnn    1860
nnnnnnnnnn nnnnnnnnnn nnnnnnnnnn nnnnnnnnnn nnnnnnnnnn nnnnnnnnnn    1920
nnnnnnnnnn nnnnnnnnnn nnnnnnnnnn nnnnnnnnnn nnnnnnnnnn nnnnnnnnnn    1980
``` nnnnnnnnn nnnnaaaaaa aaaaaaaaaa a                                   2011

<210> SEQ ID NO 36
<211> LENGTH: 1052
<212> TYPE: RNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (1)..(993)
<223> OTHER INFORMATION: n is a, c, g, or u
<220> FEATURE:
<221> NAME/KEY: misc_feature
<222> LOCATION: (996)..(997)
<223> OTHER INFORMATION: splice site
<220> FEATURE:
<221> NAME/KEY: misc_feature
<222> LOCATION: (1016)..(1037)
<223> OTHER INFORMATION: n is a, c, g, or u
<220> FEATURE:
<221> NAME/KEY: misc_feature
<222> LOCATION: (1038)..(1052)
<223> OTHER INFORMATION: poly A sequence

<400> SEQUENCE: 36 nnnnnnnnn nnnnnnnnnn nnnnnnnnnn nnnnnnnnnn nnnnnnnnnn nnnnnnnnnn      60 nnnnnnnnn nnnnnnnnnn nnnnnnnnnn nnnnnnnnnn nnnnnnnnnn nnnnnnnnnn     120 nnnnnnnnn nnnnnnnnnn nnnnnnnnnn nnnnnnnnnn nnnnnnnnnn nnnnnnnnnn     180 nnnnnnnnn nnnnnnnnnn nnnnnnnnnn nnnnnnnnnn nnnnnnnnnn nnnnnnnnnn     240 nnnnnnnnn nnnnnnnnnn nnnnnnnnnn nnnnnnnnnn nnnnnnnnnn nnnnnnnnnn     300 nnnnnnnnn nnnnnnnnnn nnnnnnnnnn nnnnnnnnnn nnnnnnnnnn nnnnnnnnnn     360 nnnnnnnnn nnnnnnnnnn nnnnnnnnnn nnnnnnnnnn nnnnnnnnnn nnnnnnnnnn     420 nnnnnnnnn nnnnnnnnnn nnnnnnnnnn nnnnnnnnnn nnnnnnnnnn nnnnnnnnnn     480 nnnnnnnnn nnnnnnnnnn nnnnnnnnnn nnnnnnnnnn nnnnnnnnnn nnnnnnnnnn     540 nnnnnnnnn nnnnnnnnnn nnnnnnnnnn nnnnnnnnnn nnnnnnnnnn nnnnnnnnnn     600 nnnnnnnnn nnnnnnnnnn nnnnnnnnnn nnnnnnnnnn nnnnnnnnnn nnnnnnnnnn     660 nnnnnnnnn nnnnnnnnnn nnnnnnnnnn nnnnnnnnnn nnnnnnnnnn nnnnnnnnnn     720 nnnnnnnnn nnnnnnnnnn nnnnnnnnnn nnnnnnnnnn nnnnnnnnnn nnnnnnnnnn     780 nnnnnnnnn nnnnnnnnnn nnnnnnnnnn nnnnnnnnnn nnnnnnnnnn nnnnnnnnnn     840 nnnnnnnnn nnnnnnnnnn nnnnnnnnnn nnnnnnnnnn nnnnnnnnnn nnnnnnnnnn     900 nnnnnnnnn nnnnnnnnnn nnnnnnnnnn nnnnnnnnnn nnnnnnnnnn nnnnnnnnnn     960 nnnnnnnnn nnnnnnnnnn nnnnnnnnnn nnngagagaa gaacggaaga acaagnnnnn    1020 nnnnnnnnn nnnnnnnaaa aaaaaaaaaa aa                                  1052

<210> SEQ ID NO 37
<211> LENGTH: 63
<212> TYPE: DNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (27)..(48)
<223> OTHER INFORMATION: n is a, c, g, or t
<220> FEATURE:
<221> NAME/KEY: misc_feature
<222> LOCATION: (49)..(63)
<223> OTHER INFORMATION: poly T sequence -continued

<400> SEQUENCE: 37
ccccctctct tcttgccttc ttgttcnnnn nnnnnnnnnn nnnnnnnntt tttttttttt    60
ttt    63

<210> SEQ ID NO 38
<211> LENGTH: 15
<212> TYPE: DNA
<213> ORGANISM: Artificial Sequence
<220> FEATURE:
<223> OTHER INFORMATION: artificially synthesized primer

<400> SEQUENCE: 38
tttttttttt ttttt    15

<210> SEQ ID NO 39
<211> LENGTH: 22
<212> TYPE: DNA
<213> ORGANISM: Artificial Sequence
<220> FEATURE:
<223> OTHER INFORMATION: artificially synthesized primer

<400> SEQUENCE: 39
ggttggaagg ttggaagggg gg    22

<210> SEQ ID NO 40
<211> LENGTH: 1042
<212> TYPE: DNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (7)..(998)
<223> OTHER INFORMATION: n is a, c, g, or t
<220> FEATURE:
<221> NAME/KEY: misc_feature
<222> LOCATION: (1021)..(1042)
<223> OTHER INFORMATION: n is a, c, g, or t

<400> SEQUENCE: 40
ccccccnnnn nnnnnnnnnn nnnnnnnnnn nnnnnnnnnn nnnnnnnnnn nnnnnnnnnn    60
nnnnnnnnnn nnnnnnnnnn nnnnnnnnnn nnnnnnnnnn nnnnnnnnnn nnnnnnnnnn   120
nnnnnnnnnn nnnnnnnnnn nnnnnnnnnn nnnnnnnnnn nnnnnnnnnn nnnnnnnnnn   180
nnnnnnnnnn nnnnnnnnnn nnnnnnnnnn nnnnnnnnnn nnnnnnnnnn nnnnnnnnnn   240
nnnnnnnnnn nnnnnnnnnn nnnnnnnnnn nnnnnnnnnn nnnnnnnnnn nnnnnnnnnn   300
nnnnnnnnnn nnnnnnnnnn nnnnnnnnnn nnnnnnnnnn nnnnnnnnnn nnnnnnnnnn   360
nnnnnnnnnn nnnnnnnnnn nnnnnnnnnn nnnnnnnnnn nnnnnnnnnn nnnnnnnnnn   420
nnnnnnnnnn nnnnnnnnnn nnnnnnnnnn nnnnnnnnnn nnnnnnnnnn nnnnnnnnnn   480
nnnnnnnnnn nnnnnnnnnn nnnnnnnnnn nnnnnnnnnn nnnnnnnnnn nnnnnnnnnn   540
nnnnnnnnnn nnnnnnnnnn nnnnnnnnnn nnnnnnnnnn nnnnnnnnnn nnnnnnnnnn   600
nnnnnnnnnn nnnnnnnnnn nnnnnnnnnn nnnnnnnnnn nnnnnnnnnn nnnnnnnnnn   660
nnnnnnnnnn nnnnnnnnnn nnnnnnnnnn nnnnnnnnnn nnnnnnnnnn nnnnnnnnnn   720
nnnnnnnnnn nnnnnnnnnn nnnnnnnnnn nnnnnnnnnn nnnnnnnnnn nnnnnnnnnn   780
nnnnnnnnnn nnnnnnnnnn nnnnnnnnnn nnnnnnnnnn nnnnnnnnnn nnnnnnnnnn   840
nnnnnnnnnn nnnnnnnnnn nnnnnnnnnn nnnnnnnnnn nnnnnnnnnn nnnnnnnnnn   900

```
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnncc aaccttccaa ccttcccccc   1020
nnnnnnnnnn nnnnnnnnnn nn                                            1042

<210> SEQ ID NO 41
<211> LENGTH: 17
<212> TYPE: DNA
<213> ORGANISM: Artificial Sequence
<220> FEATURE:
<223> OTHER INFORMATION: artificially synthesized primer

<400> SEQUENCE: 41
ggttggaagg ttggaag                                                    17

<210> SEQ ID NO 42
<211> LENGTH: 1077
<212> TYPE: DNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (23)..(1014)
<223> OTHER INFORMATION: n is a, c, g, or t
<220> FEATURE:
<221> NAME/KEY: misc_feature
<222> LOCATION: (1037)..(1058)
<223> OTHER INFORMATION: n is a, c, g, or t
<220> FEATURE:
<221> NAME/KEY: misc_feature
<222> LOCATION: (1059)..(1077)
<223> OTHER INFORMATION: poly T sequence

<400> SEQUENCE: 42
ccaaccttcc aaccttcccc ccnnnnnnnn nnnnnnnnnn nnnnnnnnnn nnnnnnnnnn     60
nnnnnnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn nnnnnnnnnn nnnnnnnnnn nnnnnnnnnn nnnnnnnnnn    240
nnnnnnnnnn nnnnnnnnnn nnnnnnnnnn nnnnnnnnnn nnnnnnnnnn nnnnnnnnnn    300
nnnnnnnnnn nnnnnnnnnn nnnnnnnnnn nnnnnnnnnn nnnnnnnnnn nnnnnnnnnn    360
nnnnnnnnnn nnnnnnnnnn nnnnnnnnnn nnnnnnnnnn nnnnnnnnnn nnnnnnnnnn    420
nnnnnnnnnn nnnnnnnnnn nnnnnnnnnn nnnnnnnnnn nnnnnnnnnn nnnnnnnnnn    480
nnnnnnnnnn nnnnnnnnnn nnnnnnnnnn nnnnnnnnnn nnnnnnnnnn nnnnnnnnnn    540
nnnnnnnnnn nnnnnnnnnn nnnnnnnnnn nnnnnnnnnn nnnnnnnnnn nnnnnnnnnn    600
nnnnnnnnnn nnnnnnnnnn nnnnnnnnnn nnnnnnnnnn nnnnnnnnnn nnnnnnnnnn    660
nnnnnnnnnn nnnnnnnnnn nnnnnnnnnn nnnnnnnnnn nnnnnnnnnn nnnnnnnnnn    720
nnnnnnnnnn nnnnnnnnnn nnnnnnnnnn nnnnnnnnnn nnnnnnnnnn nnnnnnnnnn    780
nnnnnnnnnn nnnnnnnnnn nnnnnnnnnn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn nnnnnnnnnn nnnnctctct   1020
tcttgccttc ttgttcnnnn nnnnnnnnnn nnnnnnnntt tttttttttt tttttt       1077

<210> SEQ ID NO 43
<211> LENGTH: 1077
```

```
<212> TYPE: DNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (23)..(1014)
<223> OTHER INFORMATION: n is a, c, g, or t
<220> FEATURE:
<221> NAME/KEY: misc_feature
<222> LOCATION: (1037)..(1058)
<223> OTHER INFORMATION: n is a, c, g, or t
<220> FEATURE:
<221> NAME/KEY: misc_feature
<222> LOCATION: (1059)..(1077)
<223> OTHER INFORMATION: poly T sequence

<400> SEQUENCE: 43
ggttggaagg ttggaagggg ggnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnnnnnnnnn nnnnnnnnnn nnnngagaga    1020
agaacggaag aacaagnnnn nnnnnnnnnn nnnnnnnntt tttttttttt tttttttt      1077

<210> SEQ ID NO 44
<211> LENGTH: 1036
<212> TYPE: DNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (23)..(1014)
<223> OTHER INFORMATION: n is a, c, g, or t

<400> SEQUENCE: 44
ggttggaagg ttggaagggg ggnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
```

```
nnnnnnnnnn nnnnnnnnnn nnnnnnnnnn nnnnnnnnnn nnnnnnnnnn nnnnnnnnnn    360
nnnnnnnnnn nnnnnnnnnn nnnnnnnnnn nnnnnnnnnn nnnnnnnnnn nnnnnnnnnn    420
nnnnnnnnnn nnnnnnnnnn nnnnnnnnnn nnnnnnnnnn nnnnnnnnnn nnnnnnnnnn    480
nnnnnnnnnn nnnnnnnnnn nnnnnnnnnn nnnnnnnnnn nnnnnnnnnn nnnnnnnnnn    540
nnnnnnnnnn nnnnnnnnnn nnnnnnnnnn nnnnnnnnnn nnnnnnnnnn nnnnnnnnnn    600
nnnnnnnnnn nnnnnnnnnn nnnnnnnnnn nnnnnnnnnn nnnnnnnnnn nnnnnnnnnn    660
nnnnnnnnnn nnnnnnnnnn nnnnnnnnnn nnnnnnnnnn nnnnnnnnnn nnnnnnnnnn    720
nnnnnnnnnn nnnnnnnnnn nnnnnnnnnn nnnnnnnnnn nnnnnnnnnn nnnnnnnnnn    780
nnnnnnnnnn nnnnnnnnnn nnnnnnnnnn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn nnnnnnnnnn nnnngagaga   1020
agaacggaag aacaag                                                   1036

<210> SEQ ID NO 45
<211> LENGTH: 1036
<212> TYPE: DNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (23)..(1014)
<223> OTHER INFORMATION: n is a, c, g, or t

<400> SEQUENCE: 45
ccaaccttcc aaccttcccc ccnnnnnnnn nnnnnnnnnn nnnnnnnnnn nnnnnnnnnn     60
nnnnnnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn nnnnnnnnnn nnnnnnnnnn nnnnnnnnnn nnnnnnnnnn    240
nnnnnnnnnn nnnnnnnnnn nnnnnnnnnn nnnnnnnnnn nnnnnnnnnn nnnnnnnnnn    300
nnnnnnnnnn nnnnnnnnnn nnnnnnnnnn nnnnnnnnnn nnnnnnnnnn nnnnnnnnnn    360
nnnnnnnnnn nnnnnnnnnn nnnnnnnnnn nnnnnnnnnn nnnnnnnnnn nnnnnnnnnn    420
nnnnnnnnnn nnnnnnnnnn nnnnnnnnnn nnnnnnnnnn nnnnnnnnnn nnnnnnnnnn    480
nnnnnnnnnn nnnnnnnnnn nnnnnnnnnn nnnnnnnnnn nnnnnnnnnn nnnnnnnnnn    540
nnnnnnnnnn nnnnnnnnnn nnnnnnnnnn nnnnnnnnnn nnnnnnnnnn nnnnnnnnnn    600
nnnnnnnnnn nnnnnnnnnn nnnnnnnnnn nnnnnnnnnn nnnnnnnnnn nnnnnnnnnn    660
nnnnnnnnnn nnnnnnnnnn nnnnnnnnnn nnnnnnnnnn nnnnnnnnnn nnnnnnnnnn    720
nnnnnnnnnn nnnnnnnnnn nnnnnnnnnn nnnnnnnnnn nnnnnnnnnn nnnnnnnnnn    780
nnnnnnnnnn nnnnnnnnnn nnnnnnnnnn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn nnnnnnnnnn nnnnctctct   1020
tcttgccttc ttgttc                                                   1036

<210> SEQ ID NO 46
<211> LENGTH: 19
```

<212> TYPE: DNA
<213> ORGANISM: Artificial Sequence
<220> FEATURE:
<223> OTHER INFORMATION: artificially synthesized primer

<400> SEQUENCE: 46
cttgttcttc cgttcttct                                                  19

<210> SEQ ID NO 47
<211> LENGTH: 150
<212> TYPE: DNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (23)..(41)
<223> OTHER INFORMATION: poly A sequence
<220> FEATURE:
<221> NAME/KEY: misc_feature
<222> LOCATION: (42)..(73)
<223> OTHER INFORMATION: n is a, c, g, or t
<220> FEATURE:
<221> NAME/KEY: misc_feature
<222> LOCATION: (77)..(78)
<223> OTHER INFORMATION: cleavage site
<220> FEATURE:
<221> NAME/KEY: misc_feature
<222> LOCATION: (90)..(111)
<223> OTHER INFORMATION: n is a, c, g, or t
<220> FEATURE:
<221> NAME/KEY: misc_feature
<222> LOCATION: (128)..(128)
<223> OTHER INFORMATION: n is a, c, g, or t

<400> SEQUENCE: 47
ggttggaagg ttggaagggg ggaaaaaaaa aaaaaaaaa annnnnnnnn nnnnnnnnnn       60
nnnnnnnnnn nnnatttaaa ttactaacan nnnnnnnnnn nnnnnnnnnn nttttccct     120 tttttccnca gagaagaacg gaagaacaag                                     150

<210> SEQ ID NO 48
<211> LENGTH: 150
<212> TYPE: DNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (23)..(41)
<223> OTHER INFORMATION: poly T sequence
<220> FEATURE:
<221> NAME/KEY: misc_feature
<222> LOCATION: (42)..(73)
<223> OTHER INFORMATION: n is a, c, g, or t
<220> FEATURE:
<221> NAME/KEY: misc_feature
<222> LOCATION: (77)..(78)
<223> OTHER INFORMATION: cleavage site
<220> FEATURE:
<221> NAME/KEY: misc_feature
<222> LOCATION: (90)..(111)
<223> OTHER INFORMATION: n is a, c, g, or t
<220> FEATURE:
<221> NAME/KEY: misc_feature
<222> LOCATION: (128)..(128)
<223> OTHER INFORMATION: n is a, c, g, or t

<400> SEQUENCE: 48
ccaaccttcc aaccttcccc cctttttttt tttttttttt tnnnnnnnnn nnnnnnnnnn     60
nnnnnnnnnn nnntaaattt aatgattgtn nnnnnnnnnn nnnnnnnnnn naaaaaggga    120

```
aaaaaggngt ctcttcttgc cttcttgttc                                      150
```

<210> SEQ ID NO 49
<211> LENGTH: 1039
<212> TYPE: RNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (1)..(2)
<223> OTHER INFORMATION: n is a, c, g, or u
<220> FEATURE:
<221> NAME/KEY: misc_feature
<222> LOCATION: (21)..(21)
<223> OTHER INFORMATION: n is a, c, g, or u
<220> FEATURE:
<221> NAME/KEY: misc_feature
<222> LOCATION: (24)..(25)
<223> OTHER INFORMATION: splice site
<220> FEATURE:
<221> NAME/KEY: misc_feature
<222> LOCATION: (31)..(1022)
<223> OTHER INFORMATION: n is a, c, g, or u
<220> FEATURE:
<221> NAME/KEY: misc_feature
<222> LOCATION: (1023)..(1039)
<223> OTHER INFORMATION: poly A sequence

<400> SEQUENCE: 49

```
nnccagguua acguaacaau ngaggugagu nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnnnnnnnnn nnnnnnnnnn nnnnnnnnnn    1020
nnaaaaaaaa aaaaaaaaa                                                 1039
```

<210> SEQ ID NO 50
<211> LENGTH: 1040
<212> TYPE: RNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (1)..(993)
<223> OTHER INFORMATION: n is a, c, g, or u

```
<220> FEATURE:
<221> NAME/KEY: misc_feature
<222> LOCATION: (995)..(1001)
<223> OTHER INFORMATION: n is a, c, g, or u
<220> FEATURE:
<221> NAME/KEY: misc_feature
<222> LOCATION: (1003)..(1004)
<223> OTHER INFORMATION: splice site
<220> FEATURE:
<221> NAME/KEY: misc_feature
<222> LOCATION: (1023)..(1023)
<223> OTHER INFORMATION: n is a, c, g, or u
<220> FEATURE:
<221> NAME/KEY: misc_feature
<222> LOCATION: (1024)..(1040)
<223> OTHER INFORMATION: poly A sequence

<400> SEQUENCE: 50
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnnannnnnn nagnuucaag uccaugcacc    1020
uanaaaaaaa aaaaaaaaaa                                                1040

<210> SEQ ID NO 51
<211> LENGTH: 62
<212> TYPE: RNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (1)..(2)
<223> OTHER INFORMATION: n is a, c, g, or u
<220> FEATURE:
<221> NAME/KEY: misc_feature
<222> LOCATION: (21)..(21)
<223> OTHER INFORMATION: n is a, c, g, or u
<220> FEATURE:
<221> NAME/KEY: misc_feature
<222> LOCATION: (25)..(25)
<223> OTHER INFORMATION: n is a, c, g, or u
<220> FEATURE:
<221> NAME/KEY: misc_feature
<222> LOCATION: (44)..(44)
<223> OTHER INFORMATION: n is a, c, g, or u
```

```
<220> FEATURE:
<221> NAME/KEY: misc_feature
<222> LOCATION: (45)..(62)
<223> OTHER INFORMATION: poly A sequence

<400> SEQUENCE: 51
nnccagguua acguaacaau ngagnuucaa guccaugcac cuanaaaaaa aaaaaaaaaa    60
aa                                                                  62

<210> SEQ ID NO 52
<211> LENGTH: 47
<212> TYPE: DNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (33)..(47)
<223> OTHER INFORMATION: poly T sequence

<400> SEQUENCE: 52
cattgttanc tcnaagttca ggtacgtgga tnttttttt ttttttt                  47

<210> SEQ ID NO 53
<211> LENGTH: 41
<212> TYPE: DNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 53
ccaggttaac gtaacaatng agnttcaagt ccatgcacct a                       41

<210> SEQ ID NO 54
<211> LENGTH: 41
<212> TYPE: DNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 54
ggtccaattg cattgttanc tcnaagttca ggtacgtgga t                       41
```

```
<210> SEQ ID NO 55
<211> LENGTH: 18
<212> TYPE: DNA
<213> ORGANISM: Artificial Sequence
<220> FEATURE:
<223> OTHER INFORMATION: artificially synthesized primer

<400> SEQUENCE: 55
ccaggttaac gtaacaat                                                 18

<210> SEQ ID NO 56
<211> LENGTH: 18
<212> TYPE: DNA
<213> ORGANISM: Artificial Sequence
<220> FEATURE:
<223> OTHER INFORMATION: artificially synthesized primer

<400> SEQUENCE: 56
taggtgcatg gacttgaa                                                 18

<210> SEQ ID NO 57
<211> LENGTH: 19
<212> TYPE: RNA
<213> ORGANISM: Artificial Sequence
<220> FEATURE:
<223> OTHER INFORMATION: artificially synthesized
<220> FEATURE:
<221> NAME/KEY: misc_feature
<222> LOCATION: (1)..(19)
<223> OTHER INFORMATION: poly U/C sequence
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (10)..(10)
<223> OTHER INFORMATION: n is a, c, g, or u

<400> SEQUENCE: 57
uuuuuunccn uuuuuucc                                                 19

<210> SEQ ID NO 58
<211> LENGTH: 5
<212> TYPE: PRT
<213> ORGANISM: Artificial Sequence
<220> FEATURE:
<223> OTHER INFORMATION: artificially synthesized

<400> SEQUENCE: 58

Ile Lys Gly Arg Arg
1               5

<210> SEQ ID NO 59
<211> LENGTH: 6
<212> TYPE: PRT
<213> ORGANISM: Artificial Sequence
<220> FEATURE:
<223> OTHER INFORMATION: artificially synthesized

<400> SEQUENCE: 59

Met Lys Ile Ala Ser Ile
1               5

<210> SEQ ID NO 60
<211> LENGTH: 4
<212> TYPE: PRT
<213> ORGANISM: Artificial Sequence
```

```
<220> FEATURE:
<223> OTHER INFORMATION: artificially synthesized

<400> SEQUENCE: 60

Ala Ser Val Thr
1

<210> SEQ ID NO 61
<211> LENGTH: 8
<212> TYPE: PRT
<213> ORGANISM: Artificial Sequence
<220> FEATURE:
<223> OTHER INFORMATION: artificially synthesized

<400> SEQUENCE: 61

Met Lys Ile Ala Ala Ser Val Thr
1               5

<210> SEQ ID NO 62
<211> LENGTH: 7
<212> TYPE: PRT
<213> ORGANISM: Artificial Sequence
<220> FEATURE:
<223> OTHER INFORMATION: artificially synthesized

<400> SEQUENCE: 62

Met Lys Ile Ala Ala Ser Val
1               5
```

CELL DEATH PRE-MRNA-ENCODING DNA

RELATED APPLICATION

This application is a continuation of International Application No. PCT/EP02/09082, filed Aug. 13, 2002, the contents of which are here incorporated by reference in their entirety. The benefits of 35 USC 120 are claimed.

BACKGROUND OF THE INVENTION

1. Field of the Invention

The invention relates to a method for the microsurgical, cellular repair of mutated sections of an RNA and for the specific destruction of tumor cells with the aid of an incorporated RNA capable of trans-splicing, using naturally occurring splicing components in the cell, and to a screening method for the detection of naturally trans-spliced cellular RNA.

2. Prior Art

In mammal cells, splicing processes can take place within a single RNA sequence, i.e. cis-splicing, and between separate RNA sequences, i.e. trans-splicing. Trans-splicing means that bonds within an RNA molecule are cleaved and new bonds with other RNA molecules are formed, thus producing a new RNA molecule. Such RNA trans-splicing processes therefore modify the genetic information and may give rise to modified RNA molecules or pathogenic mutations inducing tumors, for example. Providing a method of identifying trans-spliced RNA would therefore be of great importance. However, trans-splicing processes can also be used in a well-aimed fashion to repair a mutated gene or e.g. specifically destroy tumor cells. For this reason, the present inventors seek protection by patents for a basic process and for a product by means of which, depending on the case of application, trans-spliced RNA for therapeutic purposes is produced, or possibly pathogenic, cellularly trans-spliced RNA can be diagnosed.

These uses are based on the procedural basic principle of producing an artificial pre-mRNA by means of a DNA that is introduced into living cells, which pre-mRNA differs substantially in its structure from all natural cellular pre-mRNA molecules: namely, said artificial pre-mRNA comprises only 1 or 2 splice sites at maximum, corresponding to an exon flanked at both of its ends by one or two "intron moieties", herein defined as outrons. Depending on the case of application, this exon then is used to replace/repair a genetically defective exon of a natural cellular RNA by means of a replacement procedure (application principle 1), or in tumor cells, for example, after coupling to an exon from a tumor-specific RNA, causing formation of an mRNA encoding a protein which directly or indirectly induces cell breakdown of the tumor cell (application principle 2), or the exon is part of an RNA probe by means of which cellular pre-mRNAs capable of trans-splicing are identified at first, which optionally interact to form diagnosable new hybrid mRNA molecules in the cell (case of application 3), which in turn trigger possibly pathogenic processes.

In addition, the RNA which is used in each of the three cases and correspondingly includes one or two splice sites must meet specific requirements in each case to ensure sufficient functional efficiency: in order to exhibit high potency in intermolecular trans-splicing, the splice sites are required to include sequences allowing optimum binding of splicing (helper) proteins to these RNA sequences. When using this RNA for therapeutic purposes (case of application 1 or 2), specific binding between the incorporated RNA capable of trans-splicing and the cellular target RNA is required in addition, which is achieved by means of an artificially generated antisense structure on the incorporated RNA, which undergoes specific pairing with the cellular target RNA in this region. The ionic-chemical bond (via hydrogen ion bridges) thus formed between the incorporated RNA and the cellular target RNA substantially increases the trans-splicing efficiency.

Referring to the application principle 1, namely, using the incorporated RNA as repair RNA, it should be noted that a large number of diseases, such as Alzheimer, Parkinson, diabetes, hemophilia B, hereditary hypertension etc., are triggered by congenital or later-acquired singular gene defects or mutations. At present, the above diseases of monogenetic cause are generally treated using medicaments in such a way that these medicaments have a purely symptom-related physiological effect, without concerning the actual causes of the clinical picture.

If the genetic defect becomes manifest only in particular cell types or in organs of specific function, substitution and replacement of such cells or organs via trans-plantation is possible as an alternative. However, due to the unresolved problems of immune rejection of heterotransplants and the risk of virus transfer, the use of these techniques is limited.

Up to now, there are only a few cases of an at least causal treatment by external supply of a protein that is missing or non-functional as a result of a genetic defect. Examples are the daily injection of insulin in diabetics or of specific blood coagulation factors in hemophilia.

In contrast to symptomatic or causal treatment, a proper cure of genetic diseases is, in principle, only possible by restoring the function of the defective or mutated gene in the cells. On a molecular level, microsurgical gene repair by specific replacement of the defective gene components in the cell is not possible according to the present state of the art, and for this reason, the defective gene is replaced in its function by introducing a homologous, intact gene according to established methods of gene therapy.

Due to various technical problems, such as limited load capacity of viral gene shuttles, it is not the actual gene consisting of many exon and intron regions, some of them being 100 kb or more in size, that is used in gene replacement. Rather, the transgene introduced into the cells is a cDNA of the gene, which is by up to 95% shorter and merely consists of the protein-encoding exon portions, and is obtained upon reverse transcription of the mRNA. At its N terminus this cDNA has a suitable promoter and at the C terminus a recognition site for RNA polyadenylation, e.g. from SV40, coupled thereto by genetic engineering. Above all, polyadenylation is responsible for the protection of the mRNA against cytoplasmatic RNases and thus for the stability thereof. Such gene-therapeutic cDNA constructs allow constant and high RNA expression. However, replacement of a defective gene, with its complex structure, especially its intron portions and regulatory sequences, with a compressed cDNA homologue involves serious disadvantages:

a) A very large number (or percentage) of cellular primary gene transcripts—the pre-mRNAs—not only encode a single mRNA or a single protein, but are composed into most various mRNAs and proteins via alternative splicing processes. In cellular replacement of a gene on a cDNA rather than a DNA level, the mechanism of RNA maturing via splicing does no longer apply. For each required version of these mRNAs, another cDNA therefore must be introduced into the cell by gene therapy.

b) Furthermore, the selection of exons and thus the type of proteins formed in alternative RNA splicing in the cell is controlled by highly complex mechanisms which in turn are controlled by various external factors. Helper proteins, in particular, bind to regulatory RNA sequences, thereby influencing the selection of exons in alternative splicing processes and thus the mutual molar ratio of all sorts of possible, alternative splicing products. Moreover, the ratio of alternative splicing products with respect to each other can be subject to a complex process control in time, such as the various splicing forms in immunoglobulins (IgM, IgG etc.). Frequently, however, it is precisely the introns which include the regulatory sequences for alternative splicing processes. Thus, even in those cases where all sorts of possible alternative mRNA forms were available as a result of various cDNA constructs introduced (see a), physiological—and frequently also time-controlled—quantitative regulation of these mRNAs with respect to each other is absent, because the regulatory intron sequences are not included in such cDNAs. Replacement of alternatively spliceable defective genes by means of conventional methods using a cDNA lacking these intron structures is therefore disadvantageous.

c) Another essential aspect is that regulatory sequences for transcription control, such as enhancers etc., sometimes are situated at a great N-terminal distance from the promoter, or even in intron regions. However, artificial cDNA gene constructs no longer have this natural background, i.e., the intron regions are absent (see above) as are the regulatory sequences which are often far away from the promoter on the non-transcribed DNA. Thus, even when using the authentic promoter, cDNA constructs no longer exhibit the cellular fine regulation of transcription and therefore, non-physiological over- or underexpression of proteins may occur, which in turn can do damage to cells.

Therefore, due to major DNA portions that are missing (introns and other regions are absent), an artificially introduced, compressed replacement cDNA provided with a promoter and a new polyadenylation site can never have the complexity of the homologous natural, genetically defective gene and consequently cannot be a physiologically adequate substitute.

Where large genetically defective mRNAs or proteins (molecular weight: 150-200 kDa) are to be replaced, a transgene size of 5 kb and longer is required even when using a compressed cDNA. Such a size may result in substantial restrictions when using particular gene shuttles (e.g. adeno-associated virus (AAV)), and especially in nonvirus-mediated, direct gene transfer.

SUMMARY OF THE INVENTION

The object of the invention is therefore to provide a method which avoids the above-mentioned drawbacks and still allows the use of a defective or mutated gene, including its natural environment, as a cellular starting basis, in which method the defective gene is not completely replaced by an artificial replacement product (such as cDNA), but instead, the mutated gene is repaired specifically on the defective site using microsurgery.

However, microsurgical repair of the gene defect is not effected on the immediate DNA level, which is not possible (as yet) according to the present state of the art and in the (near) future. Rather, the gene defect is repaired on the level of a DNA transcript, i.e., an RNA which ultimately is responsible for protein synthesis. Unlike DNA, the RNA is subdivided into smaller subunits (so-called exons) which, in principle, can be combined freely and are therefore mutually exchangeable. On the primary gene transcript, i.e., the pre-mRNA, the exons are still separated by intervening non-coding RNA sequences (intron regions). A highly complex mechanism in the cell nucleus, referred to as (cis) splicing, causes excision of all intron regions, thereby directly linking the exons like beads on a string. Thereafter, the RNA (mRNA) thus formed exits the cell nucleus to be available for protein synthesis in the cytoplasm. The primary transcript (pre-mRNA) can be some kb and up to 100 kb in length (6 kb in length on average) and, in particular, intron lengths of up to 50 kb have been described. In contrast, the exons are relatively short; the exons on the N or C terminus, i.e., the exons in the middle, have a size of 100 to 150 b on average. Depending on the gene, the number of exons varies from 2 to more than 50 (about 6 to 10 on average), and the average size of the total sum of all exons in a mammalian cell mRNA is about 1.5 kb.

Genetic defects resulting in non-functional proteins frequently involve only one or just a few sites on the gene, i.e., in principle, they reside in only one of the numerous, from 2 to 50 gene exons. Instead of the complete gene, it is therefore sufficient to replace only the mutated exon portion of the gene, which is the basis of this invention. Such replacement is effected on the RNA level.

In addition to the cis-splicing process, which has been discovered about 25 years ago, and which causes linkage of the various exons on one and the same pre-mRNA molecule, there are also so-called trans-splicing processes in a mammalian cell, which have been detected as actually existing in vivo for the first time and published in the mid-nineties by the developer of the invention described hereinafter, who also is the applicant of the present patent. In such trans-splicing processes, different pre-mRNAs or exons from two or more pre-mRNA molecules are combined with each other. That is, repair replacement of a defective exon with an intact exon is possible by utilizing the natural RNA trans-splicing capacity of mammalian cells.

BRIEF DESCRIPTION OF THE DRAWINGS

FIGS. 1A and 1B show the association between the 5' splice site and the 3' splice site. FIG. 1A shows the association between the 5' splice site and the 3' splice site in the E-complex (SEQ ID NO:1). FIG. 1B shows the association between the 5' splice site and the 3' splice site in the B/C-complex (SEQ ID NO:2).

FIGS. 2A and 2B show in which way a mutated, genetically defective cellular mRNA is formed from a defective pre-Mrna.

FIGS. 3A and 3B in which way, in principle, a non-N-terminal or non-C-terminal genetically defective exon on a pre-mRNA (stage 1) can be replaced in a homologous fashion with the intact exon by trans-splicing using a repair RNA. FIGS. 3A and 3B show the repair RNA includes two splice sites in addition to the repair exon, i.e., a proximate (5') and a distal (3') outron.

FIG. 4 shows that in contrast, to replace a terminal, mutated and partially protein-encoding exon, single trans-splicing merely is required; to repair an encoding gene defect in an N-terminal exon, the repair RNA consequently consists of a repair exon and a distal (3') outron.

FIG. 5 shows that in the event of an encoding gene defect in a C-terminal exon, the repair RNA correspondingly consists of a proximate (5') outron, followed by the repair exon.

FIGS. 6A-6K show identification of repaired (intact) and not repaired (mutated) mRNA.

FIGS. 7A-7K show that only one outron in the repair RNA, is required if the repair exon includes the genetic information of several terminal exons in the form of a cDNA.

FIGS. 8A-8K show that only one outron in the repair RNA, is required if the repair exon includes the genetic information of several terminal exons in the form of a cDNA.

FIG. 9A shows peptide sequence SEQ ID NO:3 and cellular target RNA SEQ ID NO:4. FIG. 9B shows peptide sequence SEQ ID NO:3 and trans-splice RNA SEQ ID NO:5. FIG. 9C shows peptide sequence SEQ ID NO:3; cellular target RNA SEQ ID NO:6; and trans-splice RNA SEQ ID NO:7.

FIG. 10A shows the peptide sequence SEQ ID NO:58 and cellular target RNA SEQ ID NO:8. FIG. 10B shows the peptide sequence SEQ ID NO:58 and trans-splice RNA SEQ ID NO:9. FIG. 10C shows cellular target RNA SEQ ID NO:10; peptide sequence SEQ ID NO:58; and trans-splice RNA SEQ ID NO:11.

FIGS. 11A-11H show generation of deadly proteins in tumour cells after trans splicing.

FIGS. 12A and 12B shows safe generation of a nonsense protein.

FIGS. 13A-13D show generation of active HSV/Tk protein after RNA trans-splicing. FIG. 13A shows peptide sequence SEQ ID NO:59; RNA sequence SEQ ID NO:12; peptide sequence SEQ ID NO:60; and RNA sequence SEQ ID NO:13. FIG. 13B shows peptide SEQ ID NO:61 and RNA sequence SEQ ID NO:14. FIG. 13C shows peptide sequence SEQ ID NO:62.

FIGS. 16A and 16B show probe/exploration RNA with a 3' ss (transferred into cell) and also with bound U2AF complex. FIG. 16A shows poly-(A)-sequence SEQ ID NO:15 and poly-(U)-sequence SEQ ID NO:16. FIG. 16 B shows pre-mRNA SEQ ID NO:17 and poly-(U/C)-sequence SEQ ID NO:18.

FIGS. 17A-17K show a case of unspliced probe/exploration RNA. FIG. 17A shows RNA sequences SEQ ID NO:19 and SEQ ID NO:20. FIG. 17 B shows RNA sequence SEQ ID NO:21 and DNA sequence SEQ ID NO:22. FIG. 17C shows DNA sequence SEQ ID NO:24 and primer sequence SEQ ID NO:25. FIG. 17D shows DNA sequences SEQ ID NO:24 and SEQ ID NO:26. FIGS. 17E and 17F also show DNA sequences SEQ ID NO:24 and SEQ ID NO:26. FIG. 17G shows primer sequences SEQ ID NO:25 and SEQ ID NO:27 and DNA sequence SEQ ID NO:24. FIG. 17H shows DNA sequences SEQ ID NO: 28 and SEQ ID NO:29. FIG. 17I shows DNA sequences SEQ ID NO:30 and SEQ ID NO:32. FIG. 17J shows DNA sequences SEQ ID NO: 31 and SEQ ID NO:33. FIG. 17K shows primer sequences SEQ ID NO:25 and SEQ ID NO:27.

FIGS. 18A-18M show a case of unspliced probe/exploration RNA. FIG. 18A shows RNA sequences SEQ ID NO:34; SEQ ID NO:35; and SEQ ID NO:36. FIG. 18B shows DNA sequence SEQ ID NO:37 and RNA sequence SEQ ID NO:36. FIG. 18C shows primer sequences SEQ ID NO:38 and SEQ ID NO:39 and DNA sequence SEQ ID NO:40. FIGS. 18D and 18E show primer sequences SEQ ID NO:39 and SEQ ID NO:41 and DNA sequence SEQ ID NO:42. FIGS. 18F and 18G show primer sequence SEQ ID NO:41 and DNA sequences SEQ ID NO: 42 and SEQ ID NO:43. FIG. 18H shows DNA sequences SEQ ID NO:44 and SEQ ID NO:45. FIG. 18I shows primer sequences SEQ ID NO:41 and SEQ ID NO:46 and DNA sequence SEQ ID NO:45. FIGS. 18J-18M show primer sequences SEQ ID NO:41 and SEQ ID NO:46 and DNA sequences SEQ ID NO:47 and SEQ ID NO:48.

FIGS. 19A-19E show further details of the trans-splicing. FIG. 19A shows RNA sequences SEQ ID NO:49; SEQ ID NO:50; and SEQ ID NO:51. FIG. 19B shows DNA sequence SEQ ID NO:52 and RNA sequence SEQ ID NO:51. FIG. 19C shows primer sequence SEQ ID NO:38 and DNA sequences SEQ ID NO: 53 and SEQ ID NO:54. FIG. 19D shows primer sequences SEQ ID NO:55 and SEQ ID NO:56 and DNA sequence SEQ ID NO:54. FIG. 19E shows primer sequence SEQ ID NO:55.

DETAILED DESCRIPTION OF PREFERRED EMBODIMENTS OF THE INVENTION

Figure 9A:
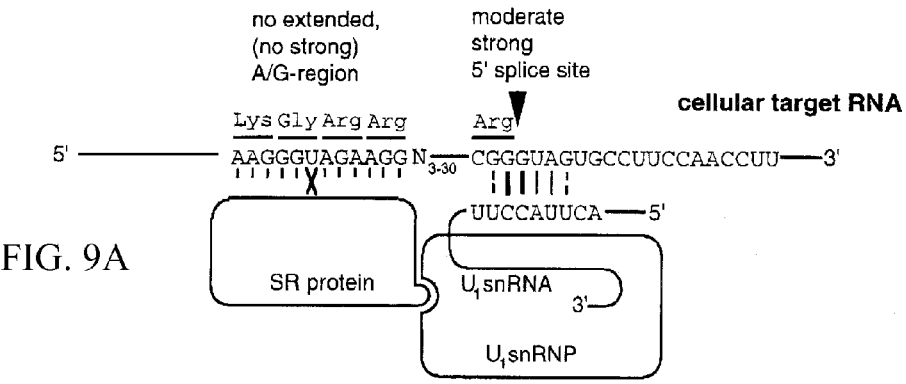
FIGS. 9A-9C show that binding of the $U_1$ snRNP to the 5' splice site is even more stabilized by so-called serine/arginine-rich proteins (S/R proteins), further $U_1$ snRNP stabilization of the pre-mRNA.

The FIGS. 2A, 2B initially show in which way a mutated, genetically defective cellular mRNA is formed from a defective pre-mRNA subsequent to ordinary cis-splicing, which mRNA encodes a non-functional protein if the mutation is not a so-called silent point mutation and if the altered amino acid causes functional impairment of the protein.

The FIGS. 3A, 3B show in which way, in principle, a non-N-terminal or non-C-terminal genetically defective exon on a pre-mRNA (stage 1) can be replaced in a homologous fashion with the intact exon by trans-splicing using a repair RNA, so that an intact mRNA is ultimately formed again (stage 2). The repair RNA is also a pre-mRNA and, in principle, consists of the exon to be replaced, which exon is flanked at each of its ends by one "intron moiety", i.e., an intron with only one splice site, herein defined as "outron". The repair pre-mRNA is produced in the mammalian cell in such a way that a coding DNA is introduced into the cell using a single DNA gene transfer procedure.

Thus, the invention solves the technical problem of microsurgical repair of a defective gene, which is preferred over gene replacement based on cDNA, by providing a method of repairing a mutated exon of a pre-mRNA in a mammalian cell, in which method a DNA encoding a repair RNA comprising a non-mutated homologous exon flanked by outrons is introduced into the mammalian cell. The mutated exon of the genetically defective RNA is then replaced by the non-mutated exon of the repair RNA via RNA trans-splicing by means of splicing components naturally occurring in the cell, thereby repairing the RNA in the defective portion thereof.

To replace an internal (non-terminal) mutated exon, double trans-splicing is therefore required as a rule; that is, the repair RNA includes two splice sites in addition to the repair exon, i.e., a proximate (5') and a distal (3') outron (see FIGS. 3A and 3B). In contrast, to replace a terminal, mutated and partially protein-encoding exon, single trans-splicing merely is required; to repair an encoding gene defect in an N-terminal exon, the repair RNA consequently consists of a repair exon and a distal (3') outron (see FIG. 4); in the event of an encoding gene defect in a C-terminal exon, the repair RNA correspondingly consists of a proximate (5') outron, followed by the repair exon (see FIG. 5). Also, merely single (instead of double) trans-splicing, and consequently only one outron in the repair RNA, is required if the repair exon includes the genetic information of several terminal exons in the form of a cDNA (see FIGS. 7A-7K and 8A-8K); this special case will be treated in more detail in a following section.

Thus, in the basic variant of the invention, a central repair exon is present which is flanked by a proximate 5' outron and a distal 3' outron, and the transfer regions or border regions between exon and outron (or intron), i.e., the splice site, always exhibit a certain structure.

The 5' splice site is situated at the far end of the exon towards the far 3' outron. 5' splice sites are sequences of 9 RNA bases including the mammalian cell consensus sequence A/C-A-G-G-U-A/G-A-G-U. A 5' splice site includes the last three nucleotides of the exon and the first six nucleotides of the outron/intron. The bases G-U are the first two bases of the intron or outron, and they are essential to a normal 5' splice site; other bases may vary. The bases of the 5' splice site undergo pairing during a very early phase (E complex) of the splicing process via H bridges with $U_1$snRNA which pertains to $U_1$ snRNP (a protein complex; see FIG. 1A). Binding between the pre-mRNA and $U_1$ snRNA—or the $U_1$ protein complex—is all the better the more Watson-Crick base pairs are formed (99 at maximum); optimum pairing to the $U_1$snRNA is achieved by the 9-base sequence (A/G)-(A/G)-G-G-U-(A/G)-(A/G)-G-U on a pre-mRNA. Binding of the $U_1$snRNP to the 5' splice site is even more stabilized by so-called serine/arginine-rich proteins (S/R proteins) (see FIGS. 9A, 9B). S/R proteins frequently bind in exon regions to RNA sections rich in purine bases. The SR proteins (e.g. ASF/SF2) bound to the RNA in exon regions (exonic splice enhancer, ESE) then associate with $U_1$ snRNP in another region of these proteins, thereby contributing to further $U_1$snRNP stabilization of the pre-mRNA (see FIGS. 9A to 9C).

The 3' splice site is situated at the anterior end of the exon towards the anterior 5' outron. In contrast to the 5' splice site, only nucleotides of the outron or intron, i.e., no exon nucleotides, are involved in the 3' splice site. The 3' splice site is more complex in structure than the 5' splice site, consisting of 3 different essential nucleotide components which in part are also separated spatially from each other. The following function as said three components of a 3' splice site: a so-called branch A site, a pyrimidine base stretch about 20 to 50 nucleotides downstream thereof, immediately followed by an essential AG dinucleotide. The AG dinucleotide simultaneously represents the far end of the outron/intron at the border to the next exon.

The relative intensity of a 3' splice site of a pre-mRNA of a mammalian cell is strongly influenced by the quality of the polypyrimidine base stretch. More specifically, the relative (U/C) ratio of the base sequence situated 2 to about 15 to 19 nucleotides upstream of the AG dinucleotide is of importance. A continuous U/C sequence is rarely present in vivo, and each $5^{th}$ or $6^{th}$ nucleotide frequently is a G or, more rarely, an A. However, the highest splice signal intensity is present in the case of a continuous U/C stretch of at least 9 to 12 nucleotides. The protein complex U2AF ($U_2$ snRNP auxiliary factor) binds via its protein portion $U2AF^{65}$ (see FIGS. 1A, 10A-10C) to the polypyrimidine stretch during a very early phase of the splicing processes (E complex). Incidentally, the consensus RNA binding site for $U2AF^{65}$ is 19 nucleotides in length, with the base sequence $U_6(U/C)CC(C/U)U_7CC$ (SEQ ID NO: 57). The second portion of U2AF, namely, $U2AF^{35}$, can bind to further SR proteins (FIGS. 10A-10C) which in turn associate to purine-rich regions in the following exon (exonic splice enhancer (ESE) regions) (see FIGS. 10A-10C). That is, these ESE regions likewise assist in binding of U2AF, as is the case in $U_1$ snRNP stabilization at the 5' splice site.

In contrast, however, the third element of the 3' splice site, the so-called branch A site situated about 20 to 50 nucleotides upstream of the poly(U/C) stretch (see also FIGS. 10A-10C), is lacking such an unequivocal definition by a specific base sequence. The mammalian consensus sequence has the 7-nucleotide sequence (C/U)-NC-U-(A/G)-A-(C/U). Essential is in particular the so-called branch A (which is underlined) which enables formation of the lariat via the 2' OH group of its ribose during a very late phase of splicing (C complex). During the splicing phase following the E complex (=A complex) and in the following B complex (see FIG. 1B), the branch sequence of the pre-mRNA undergoes pairing with $U_2$snRNA which pertains to the protein complex $U_2$snRNP (see FIGS. 10A-10C). Again, strongest possible Watson-Crick H binding between pre-mRNA and $U_2$snRNA may be important, but also "protrusion" of the branch A in the RNA stretch bound to the $U_2$snRNA, i.e., this adenosine in particular should not bind to a base (i.e., a U) of the $U_2$snRNA (see FIGS. 10A-10C). Binding of $U_2$snRNP to the pre-mRNA is supported by U2AF already bound in the E complex. Other proteins (SF3a, SF3b) may function as linking member between U2AF and $U_2$snRNP.

Fundamentally, splicing invariably involves association of a 5' splice site with a 3' splice site. In cis-splicing said two splice sites are on the same RNA molecule, and in trans-splicing correspondingly on two different RNA molecules. Indeed, a linking nucleotide sequence between the two splice sites (always present in cis-splicing processes within the same RNA molecule) is highly favorable but not necessarily required for the splicing process. Rather, the actual association between the two splice sites is achieved by the protein complexes previously bound to the 9-mer base sequence of the 5' splice site on the one hand and to the polypyrimidine base stretch and branch A site of the 3' splice site on the other hand. That is, the two splice sites make contact via protein-protein association of these RNA-bound proteins. Such association between two splice sites via bound proteins takes place in several steps: in the early E complex of the splicing process, association between the poly(U/C) stretch of the 3' splice site and the 5' splice site occurs. At the poly(U/C) stretch of the 3' splice site, the protein complex $U2AF^{65}U2AF^{35}$ is bound, which in turn undergoes pairing via a bridge SR protein (SC35) with the $U_1$snRNP previously bound to the 5' splice site (see FIG. 1A). In contrast, association in the later B complex between the branch A site of the 3' splice and the 5' splice site proceeds in such a way that the $U_2$snRNA of the $U_2$snRNP in an snRNA portion pairs with the branch A site and in another snRNA portion with the $U_6$snRNA of the $U_6$snRNP. The $U_6$snRNA in turn pairs with bases of the intron region of the 5' splice site of the pre-mRNA. (The $U_1$snRNP previously bound here (in the E and A complex) has left the splice site in favor of the $U_6$snRNP and also, U2AF is no longer bound on the U/C stretch.) (see FIG. 1B). In an even more advanced phase, the protein complex $U_5$snRNP in one portion initially associates with the exon portion of the 5' splice site and subsequently in another portion with the exon portion of the 3' splice site as well (see FIG. 1B), followed by lariat formation of the RNA (not shown). Owing to these associating structures, very close spatial contact will therefore be present between the exons to be ligated later.

Accurate association of the splice sites is accomplished by the proteins bound to the pre-mRNA, and in cis-splicing therefore, it is not the function of the linking nucleotide chain of an intron of up to 50 kb in size to bring the 5' and 3' splice sites of an intron into the required spatial context for splicing; essentially, this only applies to very short introns about 100 bases in length. Rather, the nucleotide chain of the intron assumes the function of holding the related 5' and 3' splice sites at a maximum distance (about 100 to 500 nm, depending on the intron length) which is not too large compared to the size of the cell nucleus of 10,000 nm, so that the two splice sites loaded with the splicing proteins can contact each other some time with high probability during the continuous thermal vibration and motion of the RNA in the cell nucleus, whereafter the splicing process (via splicing stages E, A, B etc.) is induced.

Trans-splicing processes in mammalian cells proceed according to the same pattern, using the same protein complexes as cis-splicing processes, the only difference being that a linking RNA nucleotide chain between the two splice sites is not present by nature (see FIGS. 1A and 1B: imagine the broken line is not there).

Due to the fact of missing covalent binding between the two splice sites, trans-splicing processes between two particular types of RNA molecules are quite rare processes in statistical terms at first sight, when comparing the large cell nucleus diameter (about 10,000 nm) with the small diameter (about 100 nm) of the protein complexes which are bound to the 5' and 3' splice sites on two different RNA molecules.

However, as a result of random natural circumstances (or intentionally by external intervention), the probability of trans-splicing between two specific types of RNA molecules, which is very low per se, can be increased by several powers of ten when observing the following conditions:

(i) The pre-mRNA molecules to be trans-spliced should be relatively stable to degradation and should be present at high concentration in the cell nucleus. Stability to degradation means that these RNA molecules, among other things, have a polyadenyl chain at the far end thereof; that is, the DNA template of this RNA must have both signal sequences for polyadenylation (AATAAA region upstream and a GT-rich region downstream of the polyadenylation site) (see e.g. FIGS. 6A, 7A, 8A). High RNA concentration is the result of transcribing a large number of pre-mRNA molecules from the corresponding DNA template, which in turn is achieved by a strong promoter on the corresponding DNA. Thus, as a result of different promoters in the mammalian cell, there are approximately 11,000 genes in vivo which include only 15 mRNA copies on average, 500 genes including 300 copies on average, and only 4 genes which include 12,000 mRNA copies in the cell nucleus on average. For example, in the case of in vivo mammalian cell trans-splicing detected by the applicant for the first time, a large number of primary transcripts detected by quantitative PCR were produced as a result of a very strong SV40 promoter.

(ii) In intermolecular trans-splicing processes, it may also be beneficial that both RNA molecules to be trans-spliced are linked by Watson-Crick H bridges over a prolonged range of bases in antisense structures. In the case of in vivo trans-splicing in mammalian cells as detected by the applicant, such RNA pairing presumably proceeds via a naturally occurring antisense region 13 bases in length between the N-terminal portion of one RNA molecule and the C-terminal portion of the second RNA molecule. On the RNA level, the somewhat weaker G-U base pairing must be considered in addition to the strong G-C base pairing and the medium-strength A-U pairing. Depending on the G/C proportion, about 10-16 continuous, i.e. consecutive base pairings are sufficient for stable RNA-RNA association at a temperature of 37° C. That is, linkage of the two RNA molecules via such an antisense base pairing "bridge" is analogous to the function of the nucleotide chain of the intron in ordinary pre-mRNAs to be cis-spliced: the two splice sites are held by a linking nucleotide chain at a specific maximum distance which is not too large, and the onset of a splicing process following association of the protein-loaded splice sites becomes much more likely.

(iii) However, even in those cases where the two potential RNA trans-splicing partner components are in close proximity to each other, e.g. as a result of antisense H bridges, there is still no sufficient guarantee that intermolecular trans-splicing processes will sufficiently or predominantly take place: namely, a particular 5' splice site e.g. on the first RNA molecule not only can interact in a trans-splicing reaction with a 3' splice site on a second, nearby RNA molecule, but also with the opposite intronic 3' cis-splice site of the same first molecule in an ordinary cis-splicing process. This latter event will even be more likely. In particular, relative preference of trans-splicing over cis-splicing may occur in those cases where the corresponding cis-splice site has lower splice site attractiveness (not so close to the consensus sequences etc.) compared to the competing trans-splice site. However, both reactions (trans- and cis-splicing) may proceed simultaneously even in those cases. Only where the competing cis-splice site is made non-functional by other particular natural factors or external (inventive) intervention, exclusive trans-splicing can be expected.

Specifically when regarding a repair RNA required to replace a genetically defective exon via RNA trans-splicing, two fundamental conditions must be satisfied: (1) RNA trans-splicing must proceed effectively, i.e., more specifically, 5 to 50% of the genetically defective RNA molecules will be repaired (depending on the type of the gene defect); (2) RNA trans-splicing should proceed specifically and exclusively with the genetically defective RNA (and specifically with the genetically defective exon) and not with other types of RNA molecules in the cell.

In order to achieve (1) a relatively high trans-splicing rate (5-50%) and (2) high substrate specificity, the following criteria must be satisfied with respect to an artificially created repair RNA (this case of application), or with respect to trans-splicing of an incomplete "cell death RNA" with a tumor cell-specific RNA (see next case of application 2 described in detail), observing the explanations above:

1) In particular, the DNA encoding the RNA to be trans-spliced (repair RNA etc.) should include a strong RNA polymerase-II promoter, e.g. SV40 early T-antigen promoter or others having a strong enhancer (see FIG. 6A), so as to allow production of a large number of RNA transcripts capable of trans-splicing. The efficiency of a trans-splicing reaction crucially depends on the cell nucleus concentration of the RNA molecules to be trans-spliced (=substrate).

2) The DNA encoding the RNA to be trans-spliced (repair RNA etc.) should have the signal sequences for pre-mRNA polyadenylation e.g. at the 3' end thereof, because polyadenylation is responsible for the stability of an RNA, among other things. As a highly potent polyadenylation region, it is also possible to use e.g. the corresponding region of the early SV40 DNA region.

3) In another aspect, the transgenic product encoding the trans-splicing RNA should be integrated in suitable vectors which, inter alia, allow independent replication of the transgene, tend to exclude integration of this DNA in chromosomal DNA, and do not allow a possible immune defense via other coding proteins of the vector.

4) The RNA to be trans-spliced (repair RNA, incomplete "cell death RNA" etc.) should be linked with the trans-splicing partner component (genetically defective RNA, tumor cell-specific RNA etc.) via ionic bonds (H bridges) in order to increase the trans-splicing efficiency. This can be accomplished in that the repair RNA etc. has a prolonged, consecutive sequence of nucleotides in the outron RNA portions, which undergoes pairing via antisense H bridges with a corresponding region on the RNA to be repaired etc. This is achieved by generating a corresponding antisense sequence in the DNA encoding this trans-splicing RNA (repair RNA etc.).

In order to allow stable RNA-RNA hybridization under physiological conditions of the cell (37° C., neutral pH value, 150 mM NaCl concentration etc.), the hybridization zone of the Watson-Crick H bridges should have minimum length. As a quite rough guide value for the annealing temperature, the following applies: the base pairing C-G, the pairing A-U and A-T, and the pairing G-U rise the annealing temperature by about 3° C., about 2° C. and about 1° C. above 0° C., respectively. A continuous RNA-RNA hybridization zone 12 bases (mer) in length, statistically distributed consisting of: 6 binding pairs C-G and 6 binding pairs A-U thus includes a total of 30H bridges with approximately 30° C. melting temperature, which is a minimum value; actually, the value is some degrees Celsius higher, and precise calculation is possible by means of appropriate EDP programs. Regarding the annealing temperature under cell physiological conditions, a hybridization zone at least 12-14 bases in length is therefore sufficient for stable RNA-RNA binding with linear RNA.

However, specific secondary structures of the external RNA to be trans-spliced (repair RNA etc.) and of the cellular RNA trans-splicing partner component (genetically defective RNA etc.) must be considered when selecting the intentional nucleotide sequence on the repair RNA which is to hybridize. As a rule, RNAs are not present in the form of a long, linear nucleotide chain, but instead, intramolecular hybridization zones are also possible, thereby forming a double-stranded RNA across a particular RNA region, with formation of stem loops, hairpins etc. Using suitable computer programs, however, it is possible to find out which RNA regions within an RNA molecule will undergo pairing with each other under physiological conditions. Thus, when ascertaining that an artificially created RNA sequence within a repair RNA etc. of e.g. 12 or more nucleotides predominantly undergoes intramolecular RNA pairing with other regions on this RNA, this sequence is to be ruled out and a modified sequence is to be selected which, of course, should undergo pairing with the genetically defective RNA etc. Correspondingly, the pairing region on the genetically defective RNA etc. should be analyzed as well, because this region should also be available for intermolecular pairing with the repair RNA etc., i.e., blocking by intramolecular pairing with other regions of the genetically defective RNA etc. must likewise be absent. Again, RNA sequences suitable for this purpose can be selected using appropriate EDP programs.

The external RNA to be trans-spliced (repair RNA, incomplete "cell death RNA" etc.) should have highly stringent 5' and 3' splice sites. More specifically, the 5' splice site or the 3' splice site e.g. on the repair RNA should be more attractive to the splicing enzymes (spliceosomes and helper proteins) than the authentic, analogous cis-splice sites on the genetically defective cellular RNA, so that these analogous cis-splice sites—which would result in a genetically defective RNA—will not be used, but instead, the trans-splice sites on the repair RNA are used, thereby producing a repaired mRNA (see FIGS. 2A, 2B, 3A, 3B).

In particular, the 5' splice site (see FIGS. 9A to 9C) of the trans-splicing repair RNA should be more attractive to the proteins of the splicing apparatus—particularly $U_1$snRNP—than the analogous, undesirable 5' cis-splice site on the genetically defective RNA. In general, this condition can be satisfied, because the natural cellular cis-splice sites, i.e., the corresponding 5' cis-splice sites on the genetically defective RNA as well, normally do not undergo optimum pairing with the $U_1$snRNA of the splicing protein complex $U_1$snRNP, that is, they show slight deviations from the optimum 5' splice site sequence (see FIG. 9A-9C). Therefore, it would be desirable to create a splice-optimal sequence 9-mer in length in the 5' splice site of the repair RNA using measures of genetic engineering (on the level of the coding DNA). In the intron portion or outron portion of the 5' splice site of the repair RNA etc., which comprises 6 bases, this means creating a sequence including the succession G-U-(A/G)-(A/G)-G-U, the preferred sequence being: G-U-A-A-G-U; this base sequence undergoes optimum pairing (largest number of H bridges) with $U_1$ snRNA. In contrast, intentional intervention—with the aim of achieving an optimal splice site sequence—in the exonic portion of the 5' splice site of the repair RNA, which comprises 3 bases, is possible only to a limited extent because, due to a base change with respect to the authentic splice site on the genetically defective RNA, coding for any other amino acid is to be prevented. However, there are some options of variation because one particular amino acid is normally coded for by 2, 4 or 6 different base tripletts. The conversion of the base triplett CGG (FIG. 9A) into the base triplett AGG (FIG. 9B) by artificial intervention may be mentioned as an allowable example of such a modification. The new base sequence AGG on the repair RNA shows better pairing to the $U_1$snRNA of the $U_1$snRNP compared to the analogous wt sequence CGG in the genetically defective RNA (FIGS. 9A and 9B), but both of them still code for the same amino acid, namely, arginine (Arg).

The attractivity of the 5' splice site on the repair RNA can be further increased if attachment of the $U_1$snRNP to this RNA is supported by additional splicing helper proteins. Such splicing helper proteins are usually arginine-serine-rich proteins (SR proteins) binding via a specific binding domain to purine-rich sequences or other specific sequences in the RNA. In many instances, these A/G-rich sequences acting as "splice enhancers" are located in the exon pertaining to the splice site ("exonic splice enhancer"=ESE). In the case of repair RNA, it should be attempted to obtain a preferably long or A/G-rich nucleotide stretch by replacing single bases on the DNA encoding the RNA, using genetic engineering (FIGS. 9A, 9B); in this case as well, one precondition is that when modifying the nucleotides in the exon, formation of codons for other amino acids is to be prevented. For example, the base sequence GGU in the exon of the authentic wt-RNA can be replaced with the base sequence GGA in the repair RNA (FIGS. 9A, 9B); in this way, a continuous, prolonged A/G stretch is obtained with no change in the amino acids because both GGU and GGA code for glycine. In the special case of the splicing helper protein ASF/SF2 which supports binding of $U_1$snRNP, the desired RNA sequence for binding this protein is e.g. AGAAGAAC or GGAAGAAC, or other sequences containing A, G and C only, but no U. Instead of in the exon, the ASF/SF2-binding RNA regions can also be situated in the intron/outron portion of the 5' splice site ("intronic splice enhancer"=ISE).

Similarly, the 3' trans-splice site (see FIGS. 10A-10C) on the repair RNA should be made more attractive than the corresponding analogous, competing, undesirable 3' cis-splice site on the genetically defective RNA by genetic engineering on the DNA encoding the repair RNA. One primary target in enhancing the attractivity is the poly (U/C) stretch immediately upstream of the AG sequence at the distal end of the intron or outron. Favorably, continuous pyrimidine stretches including 9 or more consecutive U or C bases in the authentic splice site of natural (wild type) RNAs are exceedingly rare, so that well-aimed, intentional gene-technological conversion of single G or A bases into C or U bases in the pyrimidine base stretch on the corresponding repair RNA (cf.

Figure 10A:
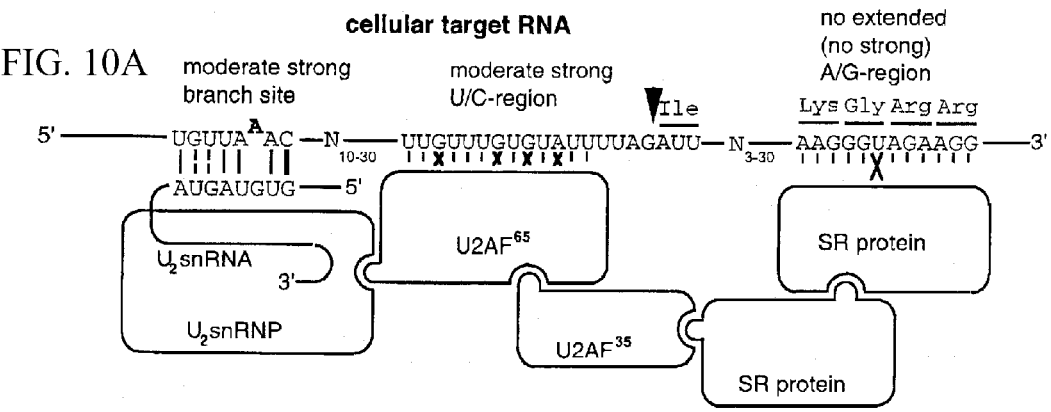
FIGS. 10A-10C show that the second portion of U2AF, namely, $U2AF^{35}$, can bind to further SR proteins.
Figure 10B:
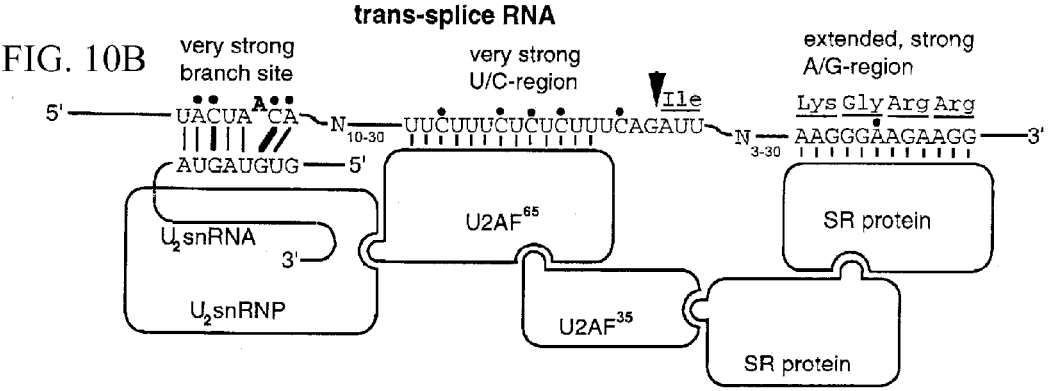

FIGS. 10A and 10B) can produce a continuous, long U/C stretch of 12 to 18 bases. The primary target of the poly (U/C) stretch is the U2AF[65] protein whose RNA binding consensus sequence is $U_6(U/C)CC(C/U)U_7CC$ (SEQ ID NO: 57), and for this reason, this particular sequence should be aimed for by intentional modification in the 3' splice site of the repair RNA. In principle, modification of the nucleotide sequence in the branch A site of the 3' splice site of the RNA to be trans-spliced (repair RNA etc.), with the aim of optimum pairing to the $U_2$snRNA of the splicing protein complex $U_2$snRNP, is also possible. A desirable nucleotide sequence would be: U-(A/G)-C-U-(A/G)-A-(C/U) on the RNA to be trans-spliced, within the branch A site (see FIGS. 10A and 10B). However, the situation with respect to the branch A site is highly complex; moreover, the precise position of the branch A site on a pre-mRNA frequently is not determined by experiment, but instead, such a branch A site is assumed thereon if the branch A consensus sequence is approximately given. In addition, many genes, such as the SV40 T antigen intron, bear even more than one possible branch A sites site upstream of the common polypyrimidine stretch. Intentional modifications of the branch A site on the repair RNA, as compared to the same site on genetically defective RNA, should only be effected conditionally, more advantageous would be modifying the polypyrimidine base stretch (see above).

Similarly, the attractivity of the 3' splice site on the repair RNA can be further increased if attachment of the U2AF protein complex to the polypyrimidine base stretch of the 3' splice site of this RNA is also supported by additional splicing helper proteins. Again, these splicing helper proteins can be S/R proteins binding e.g. to A/G-rich sequences on the RNA. Likewise, said A/G-rich sequences can be generated by changing single bases in the repair exon using genetic engineering (FIGS. 10A, 10B), and in this case as well, coding for other amino acids as a result of such base change is not allowable (see above).

To further exclude undesirable cis-splicing reactions to the genetically defective exon, resulting in genetically defective mRNA (see FIGS. 2A, 2B), these cis-splice sites should be inactivated. Inactivation is best accomplished via an RNA having artificially created antisense regions to these 5' and 3' cis-splice sites, thereby blocking and inactivating the cis-splice sites. In the simplest case, the repair RNA itself includes such antisense regions (see FIGS. 3A, 3B, 4, 5). Blocking of the analogous, competing, undesirable 5' cis-splice site having a 9-mer base sequence on the genetically defective RNA is best accomplished by means of an artificially created antisense sequence in the outron portion of the RNA to be trans-spliced, which sequence undergoes complete or predominant pairing thereto (see FIG. 9C above). Correspondingly, blocking of the analogous, competing, undesirable 3' cis-splice site on the genetically defective RNA is achieved by means of a corresponding antisense structure between the RNA to be trans-spliced and the polypyrimidine base stretch of the 3' cis-splice site (see FIG. 10C above).

Thus, the antisense regions of the repair RNA to the target RNA achieve two functions: a) establishing a stable bond to the repair RNA and b) blocking of undesirable cis-splice sites on the genetically defective RNA.

In addition, the antisense structure between the RNA to be trans-spliced (repair RNA etc.) and the target RNA has a third essential function: it provides for necessary selection of the proper RNA target, since RNA trans-splicing specifically should proceed to the genetically defective RNA (and specifically to the genetically defective exon) only, but not to other types of RNA molecules in the cell.

In statistical terms, the probability (W) of complete pairing of an RNA nucleotide sequence comprising the 4 nucleotides G, C, A, U with a corresponding antisense sequence on another RNA is: $W=1:4^n$ (n=number of nucleotides in the base stretch). In an 18-mer of a DNA, the probability of complete pairing of two DNA moieties accordingly would be $1:4^{18}=1:68,719,476,736$ (68 billions); however, due to the additionally possible RNA base pairing U-G or G-U, the probability of pairing at any site of an 18-mer RNA sequence including 9 A or C and 9 U or G in antisense with another RNA sequence is: $1/4^9 \times 2^9 = 1/262,144 \times 512 = 1:134,217,728$ (134 millions). A rough calculation of the total number of nucleotides of a mammalian cell RNA, with about 25,000 different pre-mRNAs and other RNAs (ribosomal RNA etc.) and an average pre-mRNA length of 6,000 bases, furnishes a total value of about 150 million RNA nucleotides. In statistical terms, therefore, the probability of pairing of a specifically created 18-mer base sequence including 9 A/C and 9 U/G of an RNA to be trans-spliced (repair RNA etc.) not only with the specific target RNA (genetically defective RNA etc.), but also with another RNA having an identical antisense structure, is 150 to 134 millions, i.e., the probability is about 1:1; in a 20-mer the value is therefore 1:8. However, statistical considerations alone are not sufficient: in this case as well, it should be tested by means of suitable, readily available computer programs whether undesirable complete hybridization of a particular 18 to 20-mer sequence to other unintentional RNA molecules can be excluded. In case such hybridization is possible, the base sequence to be paired on the repair RNA should be modified accordingly and the test should be repeated. In this context, however, it should be noted that pairing of the repair RNA with an RNA other than the intended target RNA (genetically defective RNA) does not imply that the repair RNA would undergo undesirable trans-splicing to this RNA, because RNA-RNA pairing alone is not a guarantee for RNA trans-splicing; in particular, conditions promoting trans-splicing via blocking etc. of any cis-splice sites must be present (see above). The question whether such undesirable trans-splicing reactions actually occur can be analyzed e.g. by means of suitable cDNA PCR procedures (see also the last-described case of application 3).

Once a DNA encoding e.g. a repair RNA has been produced and introduced into corresponding genetically defective cells by means of suitable methods, so that these cells permanently produce said repair RNA, the trans-splicing efficiency with respect to the genetically defective RNA must be analyzed in a following step. For therapeutic purposes, production of 5 to 50% of corresponding intact mRNAs or proteins compared to a cell without gene defect is sufficient, depending on the use/medical case.

Initially, such analyses are performed in preclinical studies using cell cultures at first, and then in animal experiments. The cell culture can be derived from a human suffering from a monogenetic inborn error which, in the simplest case, comprises one single base mutation which then encodes a defective protein. In the presented model example (see FIGS. 6A-6K) a gene defect on the RNA level may comprise the base sequence GAGC, whereas the intact wt sequence on the repair RNA comprises the base sequence GAUC (FIG. 6C). Analysis of the trans-splicing efficiency—the ratio of trans-spliced to cis-spliced RNA—then is possible e.g. via specific cDNA PCR from the total RNA of the cells, followed by "sequence analysis" of the cDNA PCR products. Initially, both PCR primers are selected such that essentially the cis-spliced defective mRNA molecules (FIG. 6H) or trans-spliced, repaired/intact mRNAs (FIG. 6D) will be covered, but not the corresponding pre-mRNAs having not yet undergone cis- or trans-splicing. For example, this can be achieved by selecting the primers in such a way that the primers bind precisely in the middle of the splice junction of the exon in question to the upstream and downstream exons of the ds-cDNA in the following PCR (FIGS. 6E and 6I); in an 18-mer PCR primer, for example, this would be 9 nucleotides for each of the two exon ends.

That is, two externally non-distinguishable PCR products equal in size are initially obtained in this cDNA PCR, which either derive from the cis-spliced mRNA (FIG. 6J) or from the trans-spliced mRNA (FIG. 6F).

However, it is possible to separate and distinguish the two PCR products as follows: in contrast to the genetically defective exon, one or more nucleotides have been changed in the repair exon. Considering the large number of known restriction enzymes, a new cDNA restriction site will automatically form or a previous restriction site will disappear when replacing only one nucleotide or several nucleotides. In the exemplary case presented here, the PCR product derived from the trans-spliced, repaired mRNA includes the sequence GATC which represents an MboI restriction enzyme site. If trans-spliced cDNA PCR products are exclusively present, the PCR product subsequent to MboI digestion will therefore undergo complete cleavage into two smaller fragments (FIG. 6G). However, PCR products, e.g. having the sequence GAGC, derived from the cis-spliced, defective mRNA will not be cleaved by MboI (FIG. 6K). The proportion of MboI-cleaved PCR products in relation to non-cleaved PCR products will therefore reflect the efficiency of the trans-splicing reaction in the cell. Consequently, the method describes a simplified sequencing procedure via PCR restriction fragment analysis.

Undesirably, the repair RNA might anneal to other unwanted cellular premRNAs via antisense structures and possibly undergo trans-splicing reactions there as well (see above); however, even after annealing this is rather unlikely because the repair RNA most likely will not perform specific blocking, e.g. on said other RNA, of the 5' and 3' cis-splice sites via antisense structures in this region. The detection of possible undesirable trans-spliced products is also effected via cDNA PCR: after ascertaining possible antisense binding sites of the repair RNA to other RNA molecules of the cell by means of computer analysis (see above), the analysis by means of cDNA PCR is effected, wherein a PCR primer binds to the exon of the repair RNA and the other primer correspondingly to said other cellular RNA or derived cDNA (more precisely, cf. case of application 3 and FIG. 15A). Only after completed trans-splicing with formation of a chimeric mRNA—derived from the repair RNA and a completely different RNA of the cell—the corresponding cDNA-PCR products will be detectable.

Depending on whether an internal or a terminal genetically defective exon is to be repaired, the repair RNA, or the DNA encoding the RNA, has a different basic structure:

The central element of the repair RNA is invariably the repair exon bearing the proper, corrected genetic information. This exon is flanked by one or two intron moieties, referred to as outrons. Essentially, the nucleotide sequence of the outron can be homologous to the nucleotide sequence of the corresponding intron regions situated at the border to the genetically defective exon of the cellular RNA. Essentially, base changes in the outron only relate to changes in the sequences of the splicing site and to artificial creation of an antisense structure in the outron, so that the introduced RNA can undergo pairing to the genetically defective RNA in the outron. The outrons include the major portion of the 5' splice site sequence (in the case of a far (3') outron) and all elements of the 3' splice site (in the case of an anterior (5') outron). Via these splice sites, which should be highly attractive to splicing proteins, exchange of the repair exon with the corresponding mutated exon of the genetically defective cellular RNA proceeds through a single or double trans-splicing reaction. Furthermore, these outrons assume the function of specific binding between the repair RNA and genetically defective RNA via antisense structures in the outron region towards the genetically defective RNA (selection). Moreover, as a result of such antisense RNA-RNA binding, the trans-splicing efficiency is substantially increased and, owing to simultaneous antisense blocking of the analogous cis-splice sites, undesirable cis-splicing resulting in a genetically defective RNA is blocked efficiently (see FIGS. 2A, 2B, 3A, 3B, 4, 5).

Figure 10C:
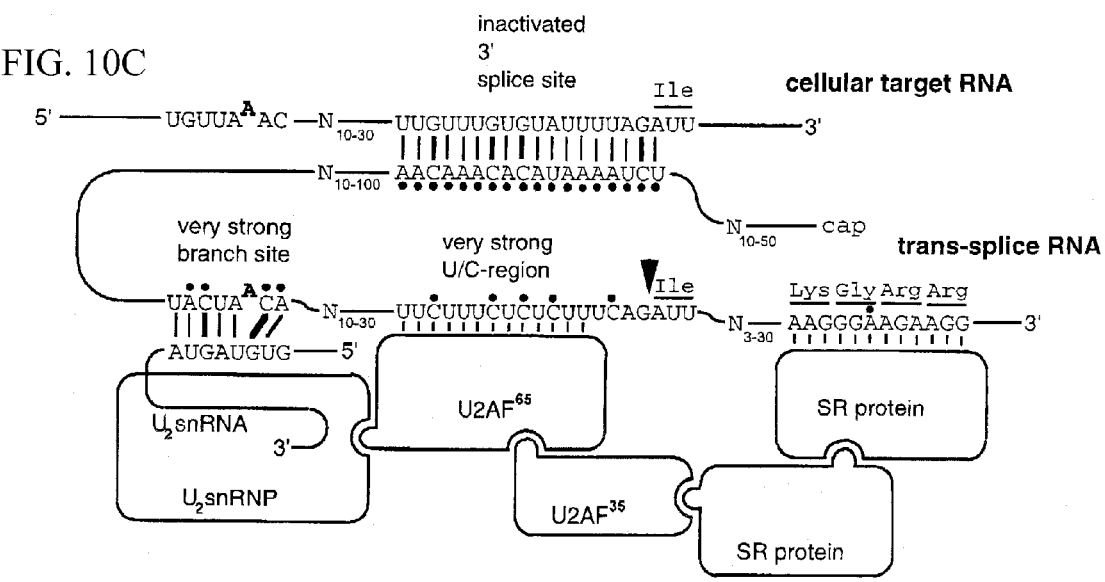

A) Accordingly, the structure of the repair RNA used to repair a non-terminal genetically defective exon (for survey see FIGS. 3A, 3B and 6A-6K) advantageously is composed as follows:

(i) Structure of the anterior (5') outron: at the 5' anterior end—i.e., at the start of the anterior outron—of the repair RNA is a cap sequence which is generated by the cell itself. Following a spacer region of n=about 10 to 50 nucleotides, this is followed by an artificially generated nucleotide region which—for selection purposes—undergoes pairing with the genetically defective RNA over a length of at least 18 consecutive bases, simultaneously inactivating the undesirable 3' cis-splice site of the genetically defective RNA via blocking of the AG nucleotide and of the polypyrimidine base stretch (FIGS. 3A, 3B and 10C). Following another spacer region of n=about 10 of 100 nucleotides (FIG. 10C), this is followed by an artificially generated, very strong 3' splice region which initially comprises an N-terminal strong branch A region including the sequence U-(A/G)-C-U-(A/G)-A (see FIG. 10C). Following another spacer region of n=about 10 of 30 nucleotides, this is followed by an artificially generated, very strong poly(U/C) region with optimally 18 consecutive U or C bases, followed by the RNA nucleotide sequence AG which represents the end of the 3' splice site and of the anterior outron of the RNA to be trans-spliced (repair RNA etc.).

(ii) Structure of the repair exon: as a result of artificial intervention (on the coding DNA), the RNA exon portion no longer bears the corresponding mutation, i.e., the exon in principle has the complete wild type (wt) sequence of the homologous RNA. The repair exon, however, unlike the wt sequence of the homologous RNA, may include other bases by exchange, provided no other amino acids will be encoded thereby. Sequences generated by genetic engineering on the level of the coding DNA would be beneficial and desirable, which sequences act as so-called exonic splice enhancers (ESE), thereby increasing the (trans) splicing efficiency. For example, purine(A/G)-rich base sequences capable of binding to arginine-serine(SR)-rich splicing helper proteins (SR proteins) are used as such ESE sequences. In an exemplary fashion, FIGS. 9A and 9B or 10A and 10B show the way of formation of such a continuous A/G stretch as ESE sequence by base substitution of one single nucleotide (U to A), without encoding other amino acids thereby.

If, as in the present case, the exon is followed by another outron having a 5' splice site, it would also be desirable to achieve the base sequence (A/G)-(A/G)-G in the exonic portion of the 5' splice site (=last 3 bases of the exon) by exchanging 1-2 nucleotides, provided no other amino acid will be encoded thereby. The above base sequence shows optimum pairing to the $U_1$ snRNA of the $U_1$ snRNP, thus promoting a (trans) splicing reaction. In the exemplary case of FIG. 9A, a base C was replaced with a base A by genetic engineering (see FIG. 9B), without encoding another amino acid thereby (invariably Arg).

(iii) Structure of the far, distal (3') outron: the following distal outron initially starts with the 6 intronic nucleotides of the 5' splice site. Here, it would be desirable to achieve the RNA nucleotide sequence G-U-A-A-G-U by genetic engineering on the coding DNA (cf., FIGS. 9A and 9B) which sequence undergoes optimum pairing with the $U_1$ snRNA of the $U_1$snRNP, thereby achieving high (trans) splicing efficiency. The bases of the outron do not code for any amino acid, which is why any intentional change of bases compared to the base sequence of the homologous intron of the genetically defective RNA is possible (cf., FIGS. 9A and 9B). Following a spacer region of n=about 10 to 100 nucleotides, the 5' splice site is followed by an artificially generated antisense region which—for selection purposes—undergoes pairing with the genetically defective RNA over a length of at least 18 consecutive bases, simultaneously inactivating the undesirable 5' splice site of the genetically defective RNA via RNA antisense blocking (FIGS. 3A, 3B and 9C). Following another spacer region of n=about 10 to 50 nucleotides, this antisense region is followed by a polyadenylation site. The coding DNA bears the recognition regions for polyadenylation, e.g. from the SV40 early gene, consisting of a sequence AATAAA upstream of the poly-A cleavage site and a GT-rich sequence downstream of the poly-A cleavage site (see FIG. 6A).

B) The structure of the repair RNA used to repair a non-internal, N-terminal-coding, genetically defective exon (see FIG. 4) consists of a repair exon followed by an outron. The repair exon—in homology to the genetically defective exon—codes for amino acids only in the far region thereof, i.e., it includes the start codon of translation, AUG. As to the fine structure of these two RNA elements, exon and outron, the above explanations apply as described in (ii) and (iii). The repair RNA includes only one splice site, which is why merely a single (instead of double) trans-splicing reaction to the genetically defective homologous cellular RNA takes place.

C) Conversely, the repair RNA used to repair a C-terminal-coding, genetically defective exon (see FIG. 5) consists of an anterior outron, followed by the repair exon. As to the fine structure of these two RNA elements, the above explanations under (i) and (ii) likewise apply, with the exception that the repair exon correspondingly does not include any nucleotides of a 5' splice site at the far end thereof. The repair exon—in homology to the genetically defective exon—codes for amino acids only in the anterior region thereof, i.e., it includes a stop codon of translation such as UAG etc. The repair exon and the encoding DNA also include a recognition region for polyadenylation at the distal end as set forth under (iii) (see also FIGS. 8A and 8B).

D) Apart from the case where the repair exon has to replace only one authentic, genetically defective exon, one might also think of that case where the cellular RNA to be repaired has a gene defect in more than one exon. If each one of two adjacent exons of an RNA has a gene defect, the repair exon correspondingly may consist of a single new exon including the genetic information of both these exons. The DNA encoding the repair exon is therefore derived from the cDNA of the mRNA from these two exons only. Again, the cDNA-derived repair exon includes two trans-splice sites or one proximate and one distal outron, respectively, or only one trans-splice site or only one proximate or distal outron, respectively.

A special case that would justify the use of such a cDNA repair exon is present where a single exon is mutated, which is situated in the anterior or far region of the genetically defective RNA, but is not the first or last coding exon. In the former case, the corresponding mutated exon of the cellular RNA might be e.g. the second coding exon (cf., FIGS. 7A-7K); the corresponding cDNA repair exon then includes the cDNA from the first and second exons. The cDNA exon is followed by an outron having a 5' (trans) splice site. This construction via a cDNA in the repair exon more or less creates an artificial N-terminal exon (see FIG. 4), that is, merely single trans-splicing (instead of double trans-splicing) is necessary for RNA repair. This implies a further increase of the yield of repaired RNA molecules, which obviously is higher when requiring merely a single instead of a double trans-splicing reaction (normal case when repairing an internal exon) to produce an intact RNA. Here, trans-splicing takes place to that exon of the cellular RNA which follows the last exon within the cDNA exon of the repair RNA.

In analogy, the reverse case applies to a gene defect e.g. in the penultimate coding exon (see FIGS. 8A-8K): the cDNA repair exon includes the combined genetic information from the penultimate and the last exon. Upstream of this cDNA exon is an outron including all the elements of a 3' splice site. That is, the singular trans-splice in this case takes place between the antepenultimate exon of the cellular RNA and the cDNA exon starting with the penultimate exon. Owing to merely singular trans-splicing, an increased yield of intact repaired cellular RNAs compared to otherwise double trans-splicing can be expected.

An extension of the examples from FIG. 7A-7K or 8A-8K would be that case where the cDNA repair exon would include (nearly) the entire mRNA information (rather than only a minor portion). In principle, this case is also conceivable for RNA repair: in one embodiment A, the N-terminal repair exon then includes the cDNA sequence from the mRNA of the coding exons 1 to N−1 (penultimate exon), and singular trans-splicing proceeds to the genetically non-defective last exon N of the cellular RNA. In an alternative embodiment B, the C-terminal repair exon then includes the cDNA sequence from the mRNA of the coding exons 2 to N (last exon), and singular trans-splicing proceeds to the genetically non-defective first exon 1 of the cellular RNA. However, the advantage of a merely singular trans-splicing reaction is at least partially counterbalanced by the requirement of a longer DNA (see below) to produce such a long repair RNA.

The advantages of using a trans-splicing repair RNA, utilizing the natural cellular splicing proteins, over conventional replacement of the complete gene by genetic engineering are the following:

In principle, only a defective portion is replaced during repair, while non-defective portions are retained. For this reason, repair is economically more favorable than complete replacement, and this applies not only to high-quality technical equipment etc., but also, in principle, to repair on the organ or cellular level in the medical sector. A pioneering aspect of the technology presented herein is that a defective gene no longer is replaced completely by an artificial gene product (on a cDNA level, inter alia) to be introduced into the cells, as in conventional somatic DNA gene therapy. Rather, the defective gene is retained in its function, being merely repaired at the defective site thereof by means of a more or less microsurgical method. This method involves incorporation of a DNA with specific requirements (as a product), which DNA encodes an RNA repairing via RNA trans-splicing the defective gene in a specific fashion only in its defective exon portion (or exon portions) on the level of the gene transcript, i.e., the RNA.

The defective gene remains in use and therefore, the regulatory sequences thereof are retained as well, which sequences are absent in cDNA gene constructs of conventional gene therapy. Above all, the intron regions should be mentioned here, which allow alternative splicing options in a natural gene, the mutual ratio of mRNA splicing products likewise being controlled by regulatory sequences within these intron regions. In addition, said intron regions of a natural gene, as well as other regions, which are often far away from e.g. the promoter, may have regulatory sequences allowing differentiated RNA expression in a cellular physiological context, which, however, are absent in cDNA gene replacement constructs.

In addition to maintaining the natural gene regulation when retaining the defective gene and merely repairing the defective gene portion, the technology described herein offers another advantage over conventional gene-therapeutic DNA methods: the DNAs encoding the repair RNAs with only one exon and two terminal outrons can be quite small: about 300 to 500 nucleotides in length, including the polyadenylation site, plus the size of the promoter (about 300 to 500 nucleotides). Hence, said DNAs encoding a repair RNA are substantially shorter even when compared to a compressed cDNA of a gene (about 1.5 to 2.5 kb in length), thereby markedly increasing the potential or efficiency of gene transfer into mammalian cells. Examples to be mentioned include the gene transfer via adeno-associated viruses (AAV) which preferentially incorporate rather short transgenes, as well as the possibility of direct gene transfers without using viral vectors (e.g. via electric fields etc.): especially these latter methods are only efficient with smaller particles for introduction into cells, i.e., relatively short DNAs.

However, a fundamentally different field of use of cDNA exons (see above) from an incorporated RNA in trans-splicing reactions is involved when gene repair via a homologous, intact RNA is not intended by means thereof. Accordingly, the exon to be trans-spliced may also exhibit gene sequences derived from completely different genes of the mammalian cell, or from genes of lower forms of life, or even from viral sources. One specific case of application would be that the hybrid mRNA product formed upon trans-splicing, or the protein resulting therefrom, assumes some new function in the cell. The potential of using the trans-splicing technology to create such non-natural hybrid proteins, which possibly may serve to accomplish particular assignments, cannot be assessed as yet. By way of example (case of application 2 of the invention), following such RNA trans-splicing, it is possible to encode functional proteins inducing e.g. specific destruction of tumor cells.

Specific destruction or elimination of tumor cells without doing damage to normal cells still is a problem requiring satisfactory solutions. Surgical tumor removal is regarded as possibly successful only in those cases where metastases have not yet been formed. Otherwise, or in case of inoperable tumors (e.g. brain tumor), only radiotherapy or chemotherapy represent usual current procedures. Both procedures also do damage to normal cells, and chemotherapy particularly destroys all rapidly dividing cells, that is, apart from tumor cells, especially blood stem cells etc., so that a high-dose chemotherapy normally must be followed by donation of marrow including new blood stem cells, and so forth. Again, promising alternatives e.g. to chemotherapy are methods of genetic engineering. Regarding approaches to a solution, there are three principles: A) elimination of the tumor-inducing gene defect; B) inactivation of active oncogenes; C) selective destruction of tumor cells. A): Especially the gene defects in the p53 gene frequently present in tumor diseases are compensated in a curative fashion by introducing an intact p53 gene; again, and as usual, the p53 gene that is introduced is the cDNA of said gene, involving the disadvantages of a compressed cDNA described above. In such tumor incidents as well, specific trans-splice repair of e.g. only the genetically defective exon by means of a specific repair RNA offers corresponding advantages (see above). B): There are various ways of inactivating active oncogenes, such as blocking of the corresponding promoters or inactivation/elimination of the oncogene RNAs having formed. C): The third approach of elimination is directed to well-aimed destruction of tumor cells, leaving normal cells unchanged. Due to this secondary condition, this approach is difficult to resolve by means of genetic engineering. The following case of application 2 of the present invention offers a solution to such problems which is based on utilizing the RNA trans-splicing capacity of all mammalian cells (normal cells and tumor cells), and in which the incorporated RNA to be trans-spliced, as described in case of application 1, is comprised of an outron and an exon, and again, said exon is trans-spliced in a selective fashion.

Tumor cells differ from normal cells in that they form particular proteins resulting in malignant cell growth. Accordingly, these proteins are encoded by particular RNAs in the cell which, accordingly, are present only in tumor cells, but not in normal cells. Examples to be mentioned include the RNAs of the oncogenes Ras, Myc etc., as well as e.g. the RNA of alpha-fetoprotein (AFP) (elevated content in the hepatocellular carcinoma), or the RNA of the carcino-embryonic antigen (CEA) (elevated concentration in liver metastases).

A method will be presented below, showing in which way these RNAs occurring in tumor cells only will ultimately lead to selective cell death of the tumor cells, without doing damage to normal cells not forming such RNAs. In principle, the method is based on incorporating a DNA in all cells (because selection between tumor cells and normal cells is not possible), which DNA encodes an RNA of a protein which directly or indirectly leads to cell death. Importantly, however, these incorporated cell death RNAs have been shortened by artificial means, so that no functional cell death protein can be formed therefrom. That is, death of the cell only occurs when enlarging or extending these incomplete cell death RNAs. Again, a tumor-specific RNA (AFP, CEA etc.) is used as means for enlargement, the actual enlargement proceeding via an RNA trans-splicing mechanism utilizing the normal splicing proteins etc. of the mammalian cell. As described above, selectivity for the tumor cell-specific RNA is achieved via appropriate artificial antisense structures on the incomplete cell death pre-mRNA. The complete cell death mRNA obtained after trans-splicing enlargement then codes for the corresponding cell death protein causing death of the tumor cells on a direct or indirect route.

In principle, the following are possible as direct or indirect "cell death proteins": a) direct toxins resulting in death of the cells (e.g. diphtheria toxin etc.), b) proteins causing cell death via an apoptotic cascade mechanism (e.g. caspase 8), and c) enzymes which intervene in the metabolism of the cell and, in the presence of an appropriate substrate (supplied externally in the form of a "medicament"), use the specific substrate to ultimately induce cell death.

In the latter case above, the cell death protein can be e.g. the virus enzyme HSV thymidine kinase (HSV-TK) which initially phosphorylates non-toxic ganciclovir (diazothymidine) supplied as "medicament". Only HSV-TK, but not the normal thymidine kinase of the mammalian cell, is capable of converting ganciclovir into the active phosphorylated derivative. During replication of the total DNA of the tumor cell, the phosphorylated ganciclovir is then incorporated in the replicated DNA chain, there giving rise to chain termination due to the diazo group, which means termination of DNA replication and thus cell death of the tumor cell (see FIG. 13D).

Incompleteness of the cell death pre-mRNA can be achieved in various ways, e.g. in that this RNA resists polyadenylation because of a missing poly-A recognition region and therefore is immediately degraded, inter alia, before protein biosynthesis (translation) can take place. In the form described in more detail herein, incompleteness of the cell death pre-mRNA is due to the fact that this RNA does have the codons for the amino acids 2 up to the last amino acid of the cell death protein, but lacks the one for the first amino acid (Met) and thus in particular the translation start codon AUG for the synthesis of the functional cell death protein. Said start codon AUG is obtained via specific RNA trans-splicing of a corresponding tumor cell-specific pre-mRNA. RNA trans-splicing proceeds between a 3' splice site upstream of the codon strand on the incomplete cell death pre-mRNA from cell death protein amino acid 2 on and the 5' splice site at the end of the first coding exon on the tumor cell-specific RNA, which bears the start codon AUG (see FIG. 11C).

The required specificity to this splice site on the tumor cell-specific pre-mRNA (e.g. AFP RNA) is achieved in that the cell death pre-mRNA to be trans-spliced bears in its outron portion upstream of its 3' splice site (i.e., upstream of the poly/-U/C region or branch A region) a sequence of 18 or more nucleotides which undergoes specific antisense pairing to the tumor cell pre-mRNA (but not to other cellular pre-mRNAs). Favorably, the corresponding antisense hybridization region is in the region of the 3' splice site of the coding exon 2 of the tumor cell pre-mRNA, thereby blocking this 3' cis-splice site, so that possible cis-splicing reaction between exon 1 and exon 2 of the tumor cell pre-mRNA no longer takes place, but only the desired trans-splicing reaction to the competing 3' splice site on the cell death pre-mRNA (see FIGS. 13A, 11C).

Subsequent to trans-splicing, a hybrid mRNA (derived from 2 gene sequences) is obtained (see FIGS. 11D, 13B), which includes the translatable first exon from the tumor cell-specific pre-mRNA (e.g. AFP RNA)- and thus the start codon AUG for protein synthesis—and the exon from the incomplete cell death pre-mRNA, which, derived from a cDNA, bears the codon sequences for amino acid No. 2 up to the last amino acid of the cell death protein (e.g. the HSV-TK protein).

Accordingly, the trans-spliceable incomplete cell death pre-mRNA in its basic structure—as outlined in the description of case of application 1 relating to the repair RNA—is comprised of a distal exon and an anterior outron and consequently includes only one splice site in the form of a 3' splice site.

In the present case, the essential structural elements of the incomplete cell death pre-mRNA comprise a coding exon which, derived from a cDNA, comprises the amino acid 2 up to the last amino acid of the cell death protein and distally thereof the recognition region for RNA polyadenylation, i.e., the coding DNA includes the sequence AATAAA upstream and a GT-rich sequence downstream of the RNA polyadenylation site (e.g. from SV40). Unless other amino acids are coded for, e.g. A/G-rich or other specific regions in the exon can be created by base exchange of single nucleotides using methods of genetic engineering, which are used as splice enhancer (ESE) via binding of S/R proteins etc. (cf., FIGS. 10A-10C).

More specifically, the proximate outron includes a highly active 3' splice site comprising a sequence of 15-18 U/C bases immediately upstream of the AG dinucleotide, and upstream of the polypyrimidine base stretch a strong branch A region including the nucleotide sequence U-(A/G)-C-U-(A/G)-A. In the outron, upstream of the branch A region, there is also a sequence—for reasons of selection specificity (see above, case of application 1)—of at least 18 nucleotides pairing in antisense to a particular tumor-specific pre-mRNA as trans-splicing partner component. Due to the antisense hybridization, blocking of the 3' splice site (in the polypyrimidine stretch thereof) upstream of the second coding exon of the tumor cell-specific RNA would be desirable, in particular. Moreover, antisense pairing and therefore, stable contact between the two RNA molecules to be trans-spliced, substantially increases the trans-splicing efficiency.

To achieve high cellular concentration of the incomplete cell death pre-mRNA and therefore high trans-splicing efficiency, the DNA encoding the RNA should bear a strong promoter (FIG. 11A), e.g. from SV40. Furthermore, the coding DNA should have a strong replication origin (e.g. from SV40 as well) so as to allow independent replication of the DNA in the cells.

However, in the special case of using an incomplete cell death RNA in the selective destruction of tumor cells, the cell death pre-mRNA, in addition to the structural elements above, should have further structural elements in the exon and outron, which assume specific functions.

i) The coding exon 1 of the tumor cell-specific RNA includes the required start codon AUG and, as a rule, the codons for additional amino acids which follow up to the end of the exon splice site as exemplified in FIGS. 13A-13D; in the AFP RNA, for example, the exon 1 codes for 28 amino acids, the last being isoleucine (see FIG. 13A). This sequence of amino acids from exon 1 of a tumor cell-specific RNA is therefore an element of the trans-spliced hybrid RNA and thus of the hybrid protein and therefore might impair the function of the cell death protein under certain circumstances. If this is detected by corresponding experiments, suitable solutions of eliminating the interfering amino acids must be implemented. One practicable way is removal of the interfering peptide portion from the tumor cell-specific protein in the hybrid protein subsequent to synthesis of the hybrid protein. This is effected by incorporating a sequence of about 15 to 45 nucleotides by genetic engineering in the incomplete cell death pre-mRNA, or in the DNA encoding this RNA, in the exon region directly upstream of the nucleotide sequence encoding the cell death protein from amino acid No. 2 on, which sequence codes for a peptide sequence of from 5 to 15 amino acids which can be cleaved by specific cellular proteases that are always present (protease recognition region, see FIGS. 11A to 11D).

Following completion of the hybrid protein, cleavage thereof in the protease recognition region is effected by a specific cellular protease, thus forming the final cell death protein, starting with amino acid 2 (merely amino acid 1, i.e., methionine, is absent), which protein still bears a few amino acids from the cleaved artificial protease recognition region upstream of said amino acid 2, which, however, should not impair the cell death function of the cell death protein (see FIGS. 11H, 13C).

ii) As described above, the trans-spliced RNA includes the translation start codon AUG from the coding exon 1 of the tumor cell-specific RNA. Following RNA trans-splicing, however, this start codon does not necessarily have to conform with the reading frame of the nucleotides of the cell death protein amino acids. If this is not the case, the reading frame must be shifted by inserting 1 or 2 nucleotides upstream of the codon of the second amino acid of the cell death protein and of the protease recognition region. These 1 or 2 additional nucleotides thus form a frame shift region or reading frame linker and are situated directly upstream of the protease recognition region and directly at the anterior end of the exon (see FIGS. 11A to 11E). In addition, the 1-2 base frame shift sequence must be selected such that no termination of translation (UAG sequence etc.) occurs in combination with the surplus to the codon of 1 or 2 nucleotides of the 5' splice site of the tumor cell RNA; moreover, the new base triplett should code for a simple amino acid (Gly, Ala) (FIG. 13B). In the example given in FIG. 13A, the AUG start codon in the exon 1 of the AFP RNA—as an example of a tumor cell-specific RNA—is situated such that the exonic portion of the 5' splice site is not terminated by a complete codon triplett. A single nucleotide (here: G) remains which, in order to maintain the reading frame, must be completed by 2 further nucleotides (here: CU) in the exon portion of the 3' splice site of the cell death RNA to be trans-spliced (see FIGS. 13A, 13B).

iii) One last essential precondition to be satisfied by the incomplete cell death pre-mRNA is that by itself, i.e., with no trans-splicing reaction to a tumor cell-specific RNA, it does not encode a protein shortened at the N terminus thereof, which still would be capable of inducing cell death. While the incomplete cell death protein RNA no longer has the authentic AUG to start translation and synthesize the first amino acid (methionine) of the cell death protein, it most likely has further AUG codons down-stream of the AUG codon for the first amino acid, i.e., methionine. Theoretically, these succeeding AUG codons on the cell death RNA might also be taken as start of translation. If an AUG codon outside the reading frame of the cell death protein is taken as start of translation, a nonsense protein will be formed, which is inactive. However, if an AUG codon downstream of the original AUG for Met 1 in the reading frame of the cell death protein is used as start of translation, a cell death protein shortened at the N terminus thereof will be formed. This protein might still have full activity as long as the amino acid portion missing at the N terminus is irrelevant to the cell death function. Accordingly, this has to be tested in pre-clinical cell experiments. When confirming this assumption, the incomplete cell death pre-mRNA must then be created in such a way that use of the AUG coding for the second Met (cf., FIG. 12A) is excluded as start of translation. As set forth in one example herein, this is achieved in a simple fashion by inserting another AUG upstream of said AUG (for Met 2), which serves as AUG translation start codon in the non-trans-spliced pre-mRNA, so that use of the AUG for the second methionine as start of translation of the cell death protein is made impossible. As a result of the intervention by genetic engineering, this AUG start codon is situated in the anterior outron upstream of the 3' splice site of the cell death pre-mRNA (FIG. 12A); moreover, this AUG start codon should be outside the reading frame of the AUG for the $2^{nd}$ Met of the cell death protein. In this case, a harmless nonsense protein is formed from the non-trans-spliced cell death pre-mRNA subsequent to start of translation from the anterior AUG start codon (FIG. 12B), thereby excluding the use of the AUG translation start codon for the $2^{nd}$ Met of the cell death protein. The termination signal (UAG) for this nonsense protein is situated in the anterior exon portion, downstream of the AUG codon for the $2^{nd}$ methionine of the cell death protein (see FIG. 12A).

Similarly, as described in case of application 1 relating to the repair RNA, the incorporation of this cell death pre-mRNA must be followed by cell culture tests in order to check the efficiency of the desired RNA trans-splicing between the tumor cell-specific RNA and the incomplete cell death pre-mRNA and to probe whether the hybrid mRNA having formed will ultimately induce death of these tumor cells. The amount of hybrid RNA having formed and thus the efficiency of the trans-splicing reaction can be detected via simple cDNA PCR. By correspondingly selecting 2 primers binding to exon 1 of the tumor cell-specific RNA and to the exon of the incomplete cell death RNA, respectively, the subsequent cDNA PCR will only detect correspondingly trans-spliced mRNAs (see FIGS. 11E and 11F). In further investigations, tests have to be conducted to see that the incomplete cell death pre-mRNA exclusively undergoes trans-splicing to the tumor-specific RNA, but not to other cellular RNAs, which is undesirable (for procedure, see description of case of application 1 relating to the repair RNA). In summary, therefore, the incorporated incomplete cell death pre-mRNA should destroy the tumor cells selectively, without doing damage to normal cells, which can be tested in corresponding cell culture experiments using tumor cells and normal cells.

Considering the preconditions described above, the DNA encoding the incomplete cell death pre-mRNA, which is subsequently completed via specific trans-splicing to a tumor cell RNA, should exhibit the following structure (from 5' to 3'):

a) At the DNA anterior end, there is a strong replication origin (e.g. from SV40).

b) This is followed by a strong promoter with enhancer (e.g. from SV40) (see FIG. 11A).

c) 10-30 nucleotides downstream of the promoter is a sequence of 18 or more nucleotides which—by way of genetic engineering—undergoes antisense pairing to the tumor cell-specific pre-mRNA precisely to the polypyrimidine base stretch and its environment of the 3' splice site of the second exon which follows the first exon having the AUG start codon (see FIGS. 11C, 13C).

d) 40-60 nucleotides downstream of the promoter end (or some nucleotides downstream of the above antisense pairing region) is an ATG codon, out-of-frame to the reading frame of the cell death protein in the following exon, which initiates a harmless, short nonsense protein in case that trans-splicing does not take place (cf., FIG. 12A).

e) 10-30 nucleotides downstream of said antisense region is a strong branch A region of a 3' splice site with the sequence T-A/G-C/T-T-A/G-A-C/T-A/G.

f) 10-30 nucleotides downstream of said branch A region is a continuous polypyrimidine base stretch (poly-T/C) of 15 to 18-mer in length, followed by the A-G dinucleotide of the 3' splice site (=far end of the anterior outron).

g) The following exon begins with a reading frame linker of 0, 1 or 2 nucleotides to compensate a possibly different reading frame between the following cell death protein in this exon and the exon 1 from the trans-spliced, tumor cell-specific RNA.

h) This very short region (0-2 nt) is followed by a region of 15 to 45 nucleotides, which codes for a sequence of 5 to 15 amino acids, which can be cleaved by cellular proteases.

i) This protease recognition region is followed by a cDNA coding for the amino acids from 2 and up to the last amino acid of the cell death protein, followed by a stop codon, e.g. TAG.

j) Within this cDNA region, downstream of the ATG codon for the $2^{nd}$ methionine of the cell death protein and out-of-frame thereto, is a stop codon for the nonsense protein produced, which is formed by the non-trans-spliced incomplete cell death protein pre-mRNA (cf., FIG. 12A).

k) 10-50 nucleotides downstream of the stop codon of translation (TAG etc.) of the cell death protein is—as a result of genetic engineering—the polyadenylation recognition site A-A-T-A-A-A, followed by a downstream G/T-rich region ($2^{nd}$ signal for recognition of polyadenylation) (see FIG. 11A) (e.g. the complete polyadenylation site from SV40).

As set forth in the cases of application 1 and 2, therapy of diseases of monogenetic cause and cancer is possible by means of external intentional RNA trans-splicing processes via an artificially created RNA comprising merely one exon and one outron. On the other hand, however, it is also possible and even very likely that diseases, or specifically cancer, are induced by independently proceeding, yet aberrant splicing processes in the cell; these processes can be both "ordinary" cis-splicing processes and, in principle, trans-splicing processes. In the third case of application presented herein, the externally introduced trans-spliceable RNA, likewise consisting of one exon and one outron, is not used as a therapeutic agent, but instead, as a diagnostic instrument to discover such aberrant cellular splicing processes.

Aberrant cis-splicing processes are known to induce a large number of diseases such as cystic fibrosis, Ehlers-Danlos syndrome, leukodystrophia, hemophilia A and B, sickle cell disease, phenylketonuria, retinoblastoma defects etc. These diseases invariably involve a mutation in an authentic 5' or 3' splice site. As a result, the corresponding authentic splice site no longer can be used as (cis) splicing partner component, and other authentic splice sites or so-called cryptic splice sites on the same pre-mRNA molecule react as splicing partner component, rather than the mutated splice site. As a result of such aberrant splicing processes, other mRNA molecules are formed, which frequently encode defective, no longer functional proteins, thereby inducing the corresponding disease.

There are numerous examples of cases where following mutation of an authentic splice site, a substitute splice site for an ordinary intramolecular cis-splicing process is no longer available on the same RNA molecule, and in this event, a (cryptic) splice site on another RNA molecule may serve as substitute splice site, so that intermolecular trans-splicing will form a completely new hybrid RNA. For example, one specific case would be if the upstream 5' splice site in the first intron of a pre-mRNA is mutated, and there is no cryptic 5' splice site substitute for cis-splicing on the same RNA molecule for the downstream, non-mutated 3' splice site (see FIG. 14A, pre-mRNA A, illustration on top). In this case, in principle, the downstream 3' splice site in the first intron pertaining to the mutated 5' splice site can only perform a splicing process when interacting with the 5' splice site on a different, second pre-mRNA molecule via trans-splicing (see FIGS. 14A, 14C).

Figure 14A:
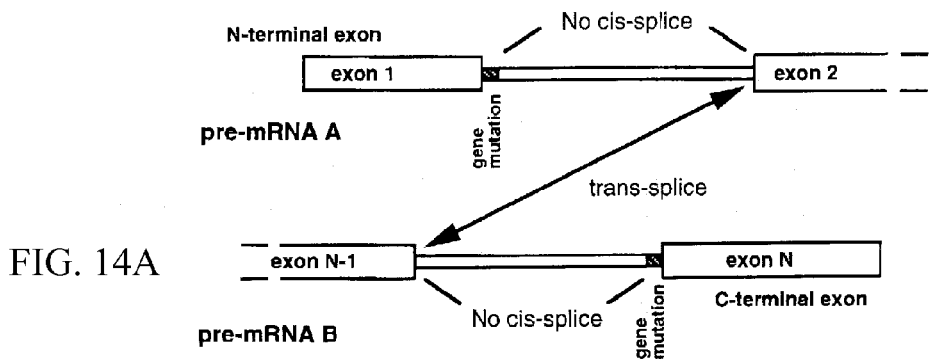
FIGS. 14A-14C show stimulation of trans-splicing by activating a cryptic splice site in N- or C-terminal exon and a mutation in a cis-splice site in a N-terminal intron.

The reverse case would be mutation of the 3' splice site in the last intron: virtually, the upstream 5' splice site of this last intron can only interact with the 3' splice site on a different RNA molecule as partner splice site (FIG. 14A, pre-mRNA B, lower illustration).

Figure 14B:
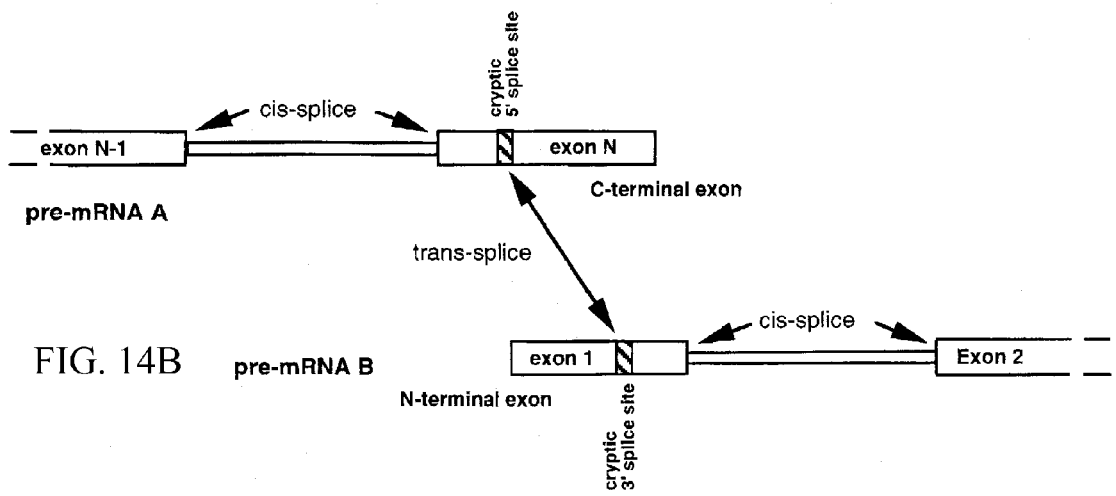

However, trans-splicing processes can also be triggered where no mutation is present in a cis-splice site: in addition to the authentic cis-splice sites, all exons frequently include further splice sites (cryptic splice sites) which, however, are less "attractive" than the authentic cis-splice sites due to their nucleotide sequence or for steric reasons etc. and are therefore not used in a (cis) splicing process. However, one special case would be if e.g. such a cryptic 5' splice site is present in the last exon, or if such a cryptic 3' splice site is present in the first exon. Due to its terminal position, such a splice site is virtually incapable of interacting with another splice site within the same RNA molecule via ordinary cis-splicing. Thus, such cryptic splice sites in terminal exons are per se highly potent splice sites for exclusive trans-splicing. In particular, cryptic 5' splice sites in C-terminal exons and cryptic 3' splice sites in N-terminal exons will interact with relatively high probability via trans-splicing, provided the two corresponding pre-mRNA molecules assume a particular distance to each other (see FIG. 14B).

Figure 14C:
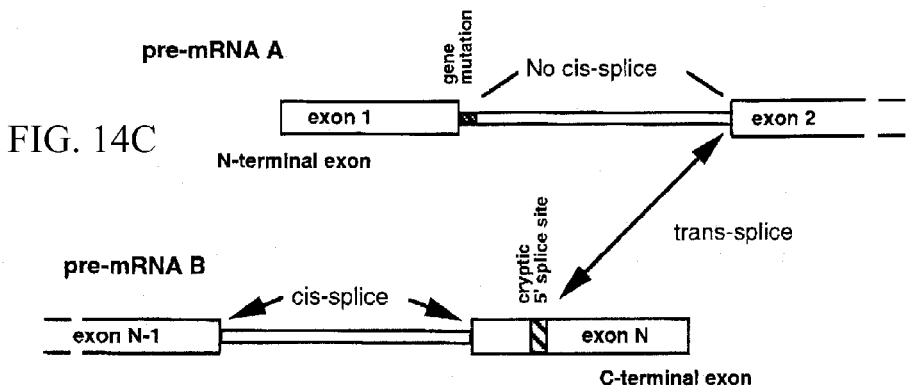

Furthermore, cryptic splice sites in terminal exons can interact by trans-splicing with trans-splice-activated cis-splice sites of terminal introns (FIG. 14C). Activation of a former cis-splice site to become a trans-splice site may also take place in such a way that the natural cis-splice partner site of this splice site is lost by mutation (FIG. 14C) and no other substitute cis-splice site is available as splicing partner component. Obviously, the reverse case is also possible, where e.g. a cryptic 3' splice site in an N-terminal exon interacts with a trans-splice-activated, former 5' cis-splice site on a different RNA molecule by trans-splicing. In total, therefore, there is quite a number of possible splice site combinations resulting in trans-spliced products.

Considering the fact that a very large number of RNA molecules have trans-spliceable splice sites, e.g. due to mutation of authentic splice sites or directly as cryptic splice sites within terminal exons, and that intermolecular RNA-RNA linkage via distinctive antisense structures in the cell nucleus, e.g. to stabilize trans-splicing processes, is not a rare incident, it can be assumed with almost complete certainty that various trans-splicing processes take place in a mammalian cell nucleus. Conceivably, such aberrant trans-splicing processes can be the cause of a disease or specifically of cancer, as has been detected and published by the applicant as early as in 1995. It is well known that aberrant splicing processes per se can cause diseases; as set forth above, more than a hundred of different diseases are induced by aberrant cis-splicing processes.

All of the naturally occurring trans-splicing processes in mammalian cells described so far were not understood until e.g. the mRNA/cDNA structure of a protein in the immunoblot, initially inexplicable with respect to its molecular weight, was elucidated. Another way of identifying trans-spliced products would be direct search on the level of cellular RNA: similarly, sizes of a specific RNA species are found in specific RNA Northern blots, which cannot be explained ad hoc and possibly might also represent products of trans-splicing. In this case as well, however, there are no straightforward methods of recognizing trans-spliced RNAs. A highly sensitive and specific method allowing, in principle, detection of one single trans-spliced RNA molecule of a cell is cDNA PCR. However, one precondition of PCR amplification and subsequent sequence analysis of a cDNA is that at least two regions of the RNA or cDNA about 18-mer in length must be known, which serve as specific PCR primer binding sites. With trans-spliced RNAs, therefore, one primer binding on the first cDNA hybrid portion derived from the first RNA and a second primer binding on the second cDNA hybrid portion derived from the second RNA are required. In principle, any RNA species can form a trans-spliced product with another RNA species. A mere check of all possible trans-splicing partner components for just one single pre-mRNA species of the cell via cDNA PCR reactions, assuming 25,000 different pre-mRNA species, would require at least 25,000 different PCR reactions with 25,000+1 different specific primers. Correspondingly, for systematic detection of all possible RNA species/RNA species splicing combinations, at least 24,999× 24,998× . . . ×3×2×1 PCR combinations would be required, which is impossible to perform in practice.

Therefore, according to the prior art, there is no easy and reliable, routine detection method of identifying trans-spliced RNA at present.

In the following third case of application, said trans-spliceable RNA incorporated in cells and consisting of one exon and one outron is used to identify natural trans-spliced products of the cell which may possibly induce diseases. The detection of such cellular trans-spliced RNAs proceeds via a two-stage mechanism, a specific cDNA PCR being employed in each partial stage.

The route to solution involves the initial necessity of finding splice sites on the approximately 25,000 different pre-mRNA species in the first stage, which would be capable of undergoing intermolecular trans-splicing reactions in principle. As set forth above, very good candidates for trans-splicing reactions are in particular cis-splice sites of N- or C-terminal introns having lost their cis-splicing partner component in this intron by splice site mutation, as well as cryptic splice sites in N- or C-terminal exons (cf., FIGS. 14A-14C).

Figure 15A:
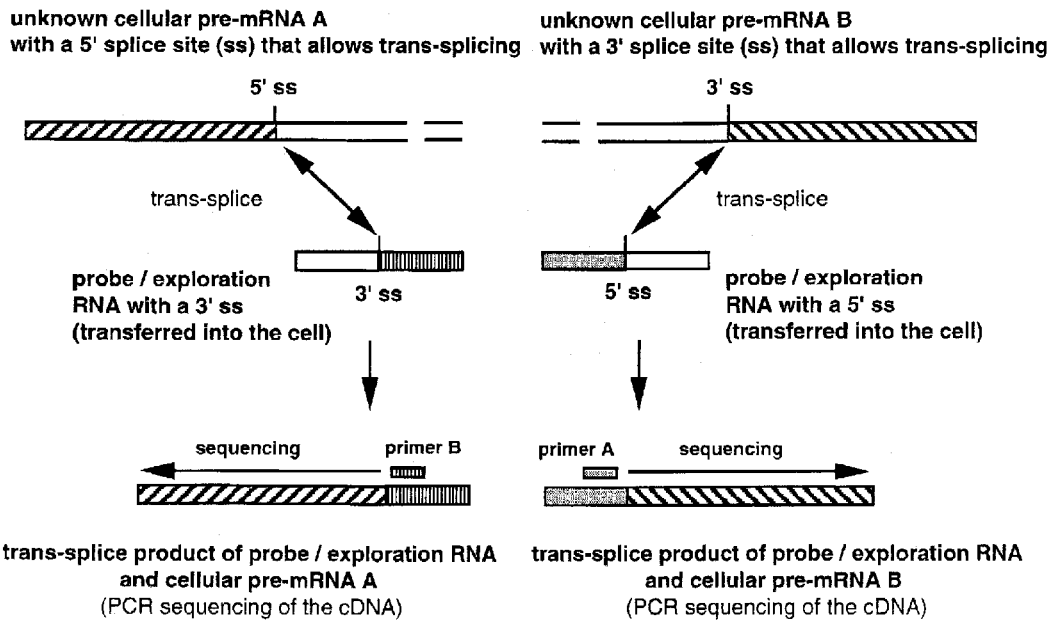
FIGS. 15A and 15B show the principle of identification of yet unknown cellular mRNA trans-splice products.

Such potent trans-splice sites are determined by allowing reaction thereof in a trans-splicing reaction. In this case, however, the trans-splicing partner component is not another unknown cellular RNA, but instead, it is said trans-spliceable RNA artificially incorporated in the cell, which more or less acts as a trans-splicing probe. In general, this RNA trans-splicing probe is a short RNA 150 to 300 nucleotides in length which only has a single 5' or a single 3' splice site, i.e., it consists of one exon and one distal or proximate outron (FIG. 15A). The probe RNA therefore reacts in its one single splice site with potential trans-spliceable splice sites of the cellular pre-mRNA molecules. Probe RNAs with a 5' splice site are used to detect trans-spliceable 3' splice site on cellular pre-mRNAs, and those with a 3' splice site are used to detect trans-spliceable 5' splice sites (see FIG. 15A, left and right). Using specific primers appropriate for the known probe RNA sequence etc., the hybrid mRNA having formed upon trans-splicing and consisting of probe RNA and cellular RNA generally can then be converted into a double-stranded (ds) cDNA, amplified by PCR, and sequenced (see FIG. 15A, bottom).

For example, once a potent 5' trans-splice site on a natural RNA species and a potent 3' trans-splice site on another RNA species have been found by means of the two RNA probes, the only thing required in stage 2 is a final test to see whether the two trans-splice sites would interact in the cell in vivo, i.e., whether the two RNAs together would form a new chimeric hybrid RNA molecule subsequent to trans-splicing. Likewise, detection of this mRNA is effected following cDNA PCR amplification using two primers selectively corresponding to the previously sequenced, trans-spliced exonic portions of the two trans-spliceable pre-mRNA molecules (see FIG. 15B, primers C and D).

Thus, the trans-spliced mRNAs to be analyzed initially in stage 1 (FIG. 15A) consist of the RNA probe exon on the one hand and of exonic portions from an unknown cellular RNA on the other hand. Ultimately, the sequence of the RNA probe is known and correspondingly, one of the two primers for cDNA PCR amplification of the trans-spliced product can be selected in an analogous fashion. However, one problem to the subsequent cDNA PCR is selection of a primer corresponding to the RNA portion derived from the cellular pre-mRNA in the product of trans-splicing: the structure of this RNA in the trans-spliced product obtained is unknown and accordingly, a corresponding specific cDNA PCR primer cannot be determined ad hoc.

Moreover, selection of a particular primer corresponding to a highly specific sequence of a cellular pre-mRNA is not helpful within the scope of the screening procedure described herein because the cDNA PCR procedure is to cover all possible combinations of probe RNA with more than 25,000 different cellular pre-mRNAs. The inventive procedure presented below allows reliable identification of all possible trans-splicing partner components when using a known probe RNA sequence, ultimately permitting amplification and subsequent sequencing of cDNA PCR products from any trans-spliced probe RNA. The corresponding second primers for PCR amplification utilize the uniform ends of all cellular mRNAs (poly-A tail at the 3' end) or a specific oligo-C structure at the anterior 5' end of all ss-cDNAs, which is generated by specific transferase activity of reverse transcriptase. The single steps (also cf. FIGS. 17A-17K and 18A-18M) of cDNA synthesis, PCR amplification and sequence analysis of the trans-spliced products of probe RNA and cellular RNA will be explained in more detail in a following section of the present description.

As in the above-described case of application 1 relating to the repair RNA, the essential structural elements of the probe RNA are an exon and a distal or proximate outron attached thereto. In this case, however, the exon is not necessarily required to encode a peptide sequence because this trans-spliceable RNA is used for diagnostic rather than therapeutic purposes. However, in analogy to case of application 2 relating to the incomplete cell death RNA, encoding of a particular peptide sequence by the exon might involve some diagnostic advantages: regarding the case of a probe RNA with a 3' splice site, for example, the distal exon might include the cDNA sequence of a protein easily detectable via specific methods (immunofluorescence etc.), which sequence is completed by a termination signal (UAG etc.) and likewise lacks the translation start codon AUG coding for methionine 1 as described above. Only when supplying this AUG via trans-splicing from another, namely, cellular RNA, a corresponding, analytically detectable protein can be formed; in in situ detection, for example, these cells then might have an appropriate fluorescence color etc.

Again, the incorporated trans-spliceable probe RNA, or the DNA encoding this RNA, includes in the distal region thereof a recognition region for polyadenylation of the RNA; that is, the coding DNA comprises the sequence AATAAA upstream and a GT-rich sequence (e.g. from SV40) downstream of the RNA polyadenylation site. Again, the exon should be provided with e.g. A/G-rich or other specific regions by means of genetic engineering, which serve as splice enhancer (ESE) by binding of S/R proteins etc. (cf., FIGS. 10A-10C). If the exon is to encode a peptide sequence (see above), care should be taken that the created e.g. A/G-rich sequences do not code for other amino acids; if the exon is not intended to encode a particular peptide, there are no limits to possible variations of the nucleotides in the exon.

In the case of a probe RNA with a 3' splice site, the proximate outron likewise includes a highly active 3' splice site comprising a sequence of 15-18 U/C bases immediately upstream of the AG dinucleotide, and upstream of the polypyrimidine base stretch a strong branch $\underline{A}$ region including the nucleotide sequence U-(A/G)-C-U-(A/G)$\underline{A}$ (see also FIGS. 10A-10C).

Figure 9B:
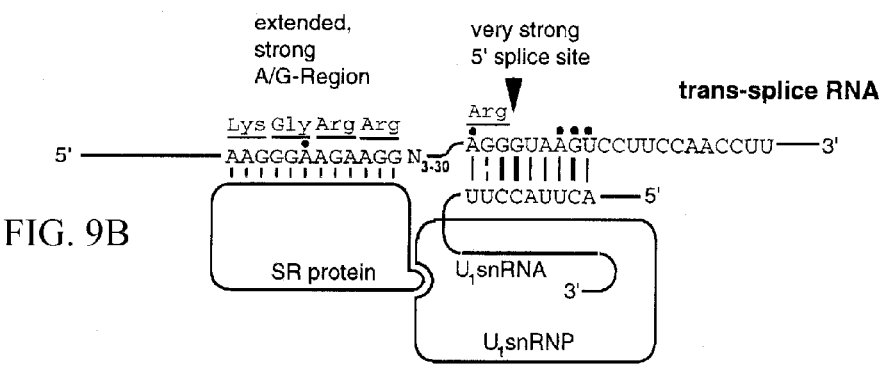
Figure 9C:
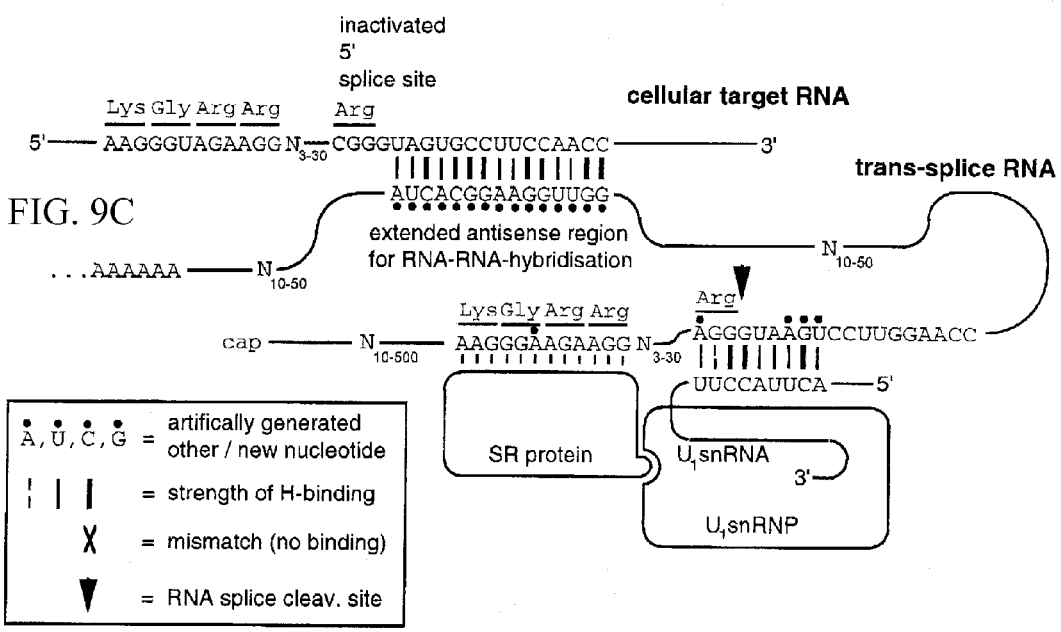

In the case of a probe RNA with a 5' splice site, the distal outron includes the intronic portion of a highly active 5' splice site having the preferred nucleotide sequence G-U-A-G-A-A, and the exonic portion of the 5' splice site includes the base sequence (A/G)-A-G (cf., FIGS. 9A-9C). Considered as an already very good natural 5' splice site made useful in the probe RNA by methods of genetic engineering is the region around a cryptic 5' splice site having the 9-mer base sequence AAG/GUAGAA in the second exon of the SV40 T antigen, which, among other things, includes upstream of the splice site a 15-mer sized A/G region as exonic splice enhancer.

To achieve high cellular concentration of probe pre-mRNA and therefore a large number of trans-splicing reactions with cellular RNAs, the DNA encoding the probe RNA should bear a strong promoter (FIG. 11A), e.g. from SV40. Furthermore, the coding DNA should have a strong replication origin (e.g. from SV40 as well) so as to allow independent replication of the DNA in the cells. Introduction of the DNA encoding the probe RNA into living cells to be analyzed for trans-spliced products is effected following incorporation in normal plasmids—adenoviruses etc. are not required—using one of the common transfection methods. In each transfection batch for the analysis for trans-spliceable cellular RNAs, only one probe RNA with a 5' splice site or one with a 3' splice site is used at a time.

As explicitly set forth in case of application 1 relating to repair RNA, the trans-splicing efficiency between an introduced RNA (here: probe RNA) and a cellular pre-mRNA can be further increased, in principle, if antisense RNA-RNA bridge binding as stable as possible is effected. In contrast to a specific repair RNA, however, an intentional, target-specific antisense region on the probe RNA cannot be generated in this case because the structure of the potential trans-splicing partner component (target RNA=cellular trans-spliceable pre-mRNA) is not known. Moreover, a highly specific structure would not make much sense because any antisense structure on the probe RNA should be selected to fit in antisense to the largest possible number or all of the cellular pre-mRNA molecules representing potential trans-splicing partner components. When selecting said probe RNA nucleotide sequence fitting to as many cellular pre-mRNA molecules as possible, there are several possibilities:

a) Antisense region to cellular RNA via oligo-U region in the probe RNA: one solution is a probe RNA with a sequence of about 12 to 18 uracil nucleotides (U) in the outron region of the probe RNA (see FIG. 16A, or FIG. 17A or 18A). This U base sequence undergoes intermolecular antisense pairing to the poly-A chain of the cellular pre-mRNAs, i.e., to the desired trans-splicing pre-mRNA as well. Furthermore, purine-rich (A/G) regions frequently occurring on cellular pre-mRNA molecules are bound in antisense by a U base sequence (on the RNA level, possible pairing is U-A, as well as U-G). Such antisense regions can achieve stable coupling between probe pre-mRNA and cellular target pre-mRNA, thereby significantly increasing the trans-splicing efficiency. However, one disadvantage of this method is that the 12-18-mer U region on the probe RNA also undergoes intramolecular pairing to the poly-A region of the probe RNA, thereby blocking the U antisense region for this probe RNA for intermolecular pairing with the target RNA. At sufficiently high substrate concentration of probe RNA in the cell, however, sufficient probe RNA molecules will also undergo intermolecular pairing with their poly-U region to the cellular poly-A appendixes of the cellular pre-mRNAs. To solve this problem, the use of an equimolar mix of probe RNAs with and without this corresponding poly-U region is suggested.

b) Antisense region to cellular RNA via oligo-G region in the probe RNA: one way is insertion of a stretch of 12 to 15 guanosine nucleotides (G) in probe RNAs which in particular include a potent 5' splice site (5'ss-probe RNA). They undergo more or less stringent intermolecular pairing to the poly(U/C) regions e.g. in the 3' splice site of cellular target pre-mRNAs (again, G-C and G-U applies to pairing on the RNA level). The disadvantage of this method is that the poly(U/C) region of the potent 3' trans-splice site on the cellular pre-mRNA possibly will also be blocked by antisense binding, so that no trans-splicing to the probe RNA takes place, and any potent trans-splice sites on a cellular pre-mRNA will therefore remain undetected.

c) No specific antisense region on probe RNA for intermolecular pairing to target pre-mRNA: as explained, specific intermolecular antisense structures between two RNA trans-splicing partner components significantly increase the efficiency of the trans-splicing reaction. However, such coupling of the two pre-mRNA molecules via antisense structures is per se not absolutely necessary for association between the two pre-mRNA molecules to be trans-spliced. As set forth above in the presentation of case of application 1 relating to the repair RNA, association of the splice sites in the splicing process also proceeds via protein-protein interaction/association of splicing (helper) proteins previously bound selectively to the 5' splice site and also selectively to the 3' splice site of the pre-mRNA.

Thus, in the early E complex of the splicing reaction, association of a pre-mRNA in its 5' splice site to the 3' splice site of the same RNA (=cis-splicing reaction) or to another RNA (=trans-splicing reaction) proceeds via association between the $U_1$snRNP protein complex (previously bound to the 5' splice site) on the one hand and the U2AF protein complex (previously bound to the poly-U/C stretch of the 3' splice site) on the other hand, optionally mediated by other SR proteins (e.g. SC 35, SF2 etc.) (see FIG. 16B, as well as FIG. 1A). Even at later stages of the splicing process there are numerous associations between different splicing (helper) proteins previously bound to the two splice sites of the pre-mRNA (see FIG. 1B).

A probe RNA including e.g. only one potent 3' splice site (3'ss-probe RNA) is bound in its poly-U/C portion of the 3' splice site to U2AF protein molecules in the cell. The probe RNA provided with the U2AF protein complex then diffuses freely in the cell nucleus until the U2AF protein encounters e.g. a $U_1$ snRNP-SC35 protein complex previously bound to a trans-spliceable 5' splice site of a cellular pre-mRNA (see FIG. 16B). This is followed by protein-protein binding/association so that the probe RNA now exhibits relatively stable binding to the possibly trans-spliceable target pre-mRNA. In analogy, the reverse case involves a probe RNA with a 5' splice site having $U_1$ snRNP formed by the cell bound thereto, and in this case the complex diffuses in the cell nucleus until it encounters an U2AF complex bound to a trans-spliceable 3' splice site of a cellular target pre-mRNA to associate with this RNA via said U2AF complex.

Also, in contrast to gene therapy via e.g. RNA trans-splicing (case of application 1), a high specific rate of trans-splicing reactions as a result of stable antisense RNA-RNA binding is not necessarily required in this detection method: in principle, one single trans-splicing reaction between a probe RNA molecule and a trans-spliceable cellular target pre-mRNA is sufficient, thereby forming one single trans-spliced mRNA molecule. This molecule is then copied selectively a million times by subsequent cDNA PCR, thereby allowing easy detection and sequencing thereof.

Thus, the trans-spliceable probe RNA for the detection of trans-spliceable cellular RNAs is simpler in structure compared to trans-spliceable therapeutic RNAs, such as repair RNA for microsurgical elimination of gene defects or even incomplete cell death RNA for the destruction of tumor cells, because selective binding to the target RNA via corresponding RNA antisense structures is not required. In contrast to such therapeutic uses, the diagnostic probe RNA—because of the subsequent procedure of detecting the trans-spliced RNAs—should have one additional structural element: a restriction enzyme recognition site for a rare cutter in the outron portion of the probe RNA. As described below, the reason for this is that the cDNA PCR for the amplification of the trans-spliced products co-amplifies the non-spliced probe RNA. However, the non-spliced probe RNA is present in the cell at much higher concentration compared to the trans-spliced products of probe RNA and cellular target RNA, which is why the PCR signal from the non-spliced probe RNA would competitively quench the PCR signal from the trans-spliced products, so that these trans-spliced RNAs no longer could be detected in the cDNA PCR. Following formation of a double-stranded (ds) cDNA, the ds-cDNA from the non-spliced probe RNA, prior to starting the PCR reaction, must therefore be degraded selectively e.g. by means of restriction enzyme digestion, without affecting the ds-cDNA of the trans-spliced products by such degradation. This can be done by placing the restriction site for enzymatic degradation of the ds-cDNA in the outron portion of the probe RNA; the ds-cDNA trans-splicing products from the probe RNA no longer have this outron portion of the probe RNA and therefore are not degraded by the restriction enzyme.

Moreover, when selecting the restriction site, a so-called rare cutter site is to be chosen. The reason for this is that the component from the unknown cellular target RNA in the trans-spliced product should not have said restriction recognition site because otherwise, the trans-spliced product would also be subject to enzymatic degradation and would not be detected in the subsequent PCR. Base sequences of 8-mer (or longer) are regarded as so-called rare cutter sites. In an 8-mer the probability (W) of encountering this sequence at a particular position in a DNA is $W=1:4^8=1:65,536$. Assuming a nucleotide sequence of 400 bases derived from the unknown cellular target RNA in the trans-spliced product, the probability of encountering such an 8-mer recognition site within the 400 bases is $W=1:65,536/400=1:164$, which can be neglected; in a 10-mer recognition sequence W is only 1:2624.

Once the incorporated coding DNA—owing to a strong promoter, among other things—has formed hundreds of thousands of probe RNA molecules per cell, some of them, in the case of a 5'ss-RNA probe, then undergo pairing to a potent 3' trans-splice site on the unknown cellular target pre-mRNA (see FIG. 17A). In the case of a 3'ss-probe RNA, corresponding pairing to a potent 5' trans-splice site on the unknown cellular pre-mRNA may form (see FIG. 18A). Linkage of the two RNA molecules can be supported by antisense regions between the poly-U chain in the outron region of the probe RNA and the poly-A tail of the trans-spliceable pre-mRNA (see FIG. 16A or 17A and 18A); however, such an antisense-nucleotide structure is not absolutely necessary for a trans-splicing process (see above).

When using a 5'ss-probe RNA, the trans-spliced product being formed includes in its N-terminal portion the exon of the probe RNA with a cap sequence formed by the cell, and in its larger C-terminal region exonic portions of the unknown trans-splicing RNA. If the trans-splice site of the cellular RNA is e.g. a cryptic 3' splice site in the last exon of this RNA, the trans-spliced product includes the RNA sequence downstream of this cryptic splice site which bears a poly-A tail. If a cryptic or even authentic 3' splice site in an anterior exon of the cellular RNA is used, the trans-spliced product includes the entire mRNA sequence of that RNA downstream of this 3' splice site, likewise including a terminal poly-A tail (see FIG. 17B). When using a 3'ss-probe RNA, the trans-spliced product being formed correspondingly includes in its larger N-terminal region the exonic portions upstream of the 5' trans-splice site from the unknown trans-spliced cellular RNA with a cap sequence, and in its C-terminal portion the exon from the probe RNA with a poly-A tail (see FIG. 18B).

Virtually, as already mentioned above, detection of the trans-spliced RNAs comprising a cellular RNA portion and the exon portion of the probe RNA can only be effected by means of cDNA PCR for reasons of selectivity and sensitivity. The first one of the two PCR primers is easy to determine, it is analogous to a nucleotide sequence in the exon of the probe RNA. To cover all possible cellular RNAs in this cDNA PCR, the second PCR primer to bind here must be created so as to be universal. The corresponding second primer for PCR amplification utilizes the uniform ends of all cellular mRNAs (poly-A tail at the 3' end) or a specific oligo-C structure at the anterior 5' end of all ss-cDNAs, which is generated by specific transferase activity of reverse transcriptase. In the former case, a primer is generally selected which has a sequence of about 15 to 18 thymidine bases (T) which undergo pairing to the poly-A ends of all mRNAs; this oligo-T sequence is followed in 5' direction by an arbitrary sequence of 18 or more nucleotides. In the second case, a primer including some guanosine bases (G) is used, and this oligo-G sequence is followed in 5' direction by an arbitrary sequence of 18 or more nucleotides.

The following sections describe a corresponding, well-tested procedure allowing reliable identification of all possible trans-splicing partner components when using a known probe RNA sequence, ultimately permitting amplification and subsequent sequencing of cDNA PCR products from any trans-spliced probe RNA.

Following incorporation in suitable plasmids or by means of other suitable procedures, the DNA encoding the probe RNAs is introduced into the mammalian cells to be investigated (e.g. tumor cells with unknown cause of tumor development etc.).

In principle, two DNA transfection batches are performed. Batch 1 comprises a DNA encoding probe RNAs with a 5' trans-splice site; therein, an equimolar transfection batch of corresponding DNAs including a nucleotide sequence $T_{15}$ to $T_{18}$ (DNA type A) or lacking same (DNA type B) is employed. Batch 2 comprises a DNA encoding probe RNAs with a 3' trans-splice site; likewise, an equimolar transfection batch of corresponding DNAs including a nucleotide sequence $T_{15}$ to $T_{18}$ (DNA type A) or lacking same (DNA type B) is employed. 24 hours and up to several days after DNA transfection, the total RNA of the cells is isolated, denatured by heat, and then converted into an ss-cDNA.

Synthesis of the first cDNA strand (ss-cDNA) from the (trans-spliced) mRNA is invariably effected by means of reverse transcription using an effective reverse transcriptase free of RNase activity and an oligo-$T_{18}$ start primer binding to the poly-A tail of trans-spliced mRNA and of any other cellular RNA molecule having a poly-A tail (see FIG. 17C, FIG. 18C).

In that case where an RNA probe with a 5' splice site has been used in the analytical batch, the oligo-T start primer $T_{15}$ at its anterior 5' end should have another sequence of 18 or more other, alternating nucleotides subsequently serving as a recognition sequence for the second primer in the PCR (i.e., total primer length is 33 or more nucleotides) (see FIG. 17C, example: 5'-AACCGGCCAACCGGCCAA-$T_{15}$-3', SEQ ID NO:23), Using appropriate bioinformatic programs, the sequence of these 18 or more nucleotides must be selected such that self-annealing etc. is avoided. Conceivably, restriction sites (e.g. EcoRI, BamHI etc.) included in said 18-mer sequences might be useful for further work (e.g. cloning); similarly, a nucleotide sequence longer than an 18-mer may be convenient (e.g. 36 to 40-mer) to enable a so-called nested PCR (i.e., two different 18 to 20-mer primers undergo binding in a 2-phase PCR) for improved selection (see below).

The synthesis of the second strand of the cDNA (ds-cDNA) from the trans-spliced mRNA will depend on the type of RNA probe being used (either having a 5' or a 3' splice site):

a) In the case of an unknown trans-spliced RNA including the exon portion of an RNA probe with a 5' splice site, synthesis of the second cDNA strand starts in the original region of the exon of the probe RNA. That is, synthesis simply begins with a primer that corresponds to an 18-mer base sequence of the exon of the probe RNA (FIG. 17D, example: 5'-AGAAGAACGGAAGAACAA-3', SEQ ID NO:25). Synthesis of this $2^{nd}$ strand from the ss-cDNA is effected e.g. by means of a single-cycle PCR or other procedures (see FIG. 17D).

b) In the case of an unknown trans-spliced RNA including the exon portion of an RNA probe with a 3' splice site, synthesis of the second cDNA strand is significantly more complicated, however, because the primer required in synthesis must bind more or less in the exon portion from the unknown trans-splicing RNA. However, a specific primer sequence cannot be determined to this end; moreover, a procedure using a primer fitting to all possible ss-cDNA trans-spliced products should be selected (see above).

For example, advantage can be taken of the fact that the reverse transcriptase, having reached the cap site on the (trans-spliced) mRNA, appends preferably several cytosines to a C chain on the single-stranded cDNA in a terminal transferase function (see FIG. 18C). Moreover, this reaction can be intensified by an excess of cytosines in the substrate compared to the other three substrate nucleotides. This N-terminal cytosine stretch of the ss-cDNA then is used as a binding site for a specific primer (cap primer) including in the downstream region thereof a sequence of about 6 to 8 guanosines (G) pairing to the cytosines (see FIG. 18D). The cap primer is added about 30 to 45 minutes after beginning the ss-cDNA synthesis at a temperature lowered to about 30° C. Said specific primer (see example: 5'-GGTTGGAAGGTTG-GAAGGGGG-3', SEQ ID NO:39) in its 18-mer (or longer) sequence upstream of the G nucleotides then is used as a template for further completion with corresponding nucleotides pairing to this primer sequence (see FIGS. 18D, 18E). Such completion is effected by the reverse transcriptase or by another suitable DNA polymerase that is added (likewise at about 30 to 32° C.). Following heat denaturation to remove this primer from the ss-cDNA, the actual synthesis of the $2^{nd}$ strand is performed by means of a single-cycle PCR using a primer which has a configuration as the cap primer above but optionally does not include the distal G stretch (see FIG. 18F, example: primer 5'-GGTTGGAAGGTTGGAAG-3', SEQ ID NO:41). In this case as well, it may be convenient to make the region upstream of the oligo-G sequence not only 18 to 20-mer (se FIG. 18C), but rather e.g. 36 to 40-mer in length so as to enable a so-called nested PCR for improved selection (see above, see below). For cloning etc., specific restriction sites (EcoRI, BamHI etc.) can be useful in this primer sequence as well.

Thereafter, the ds-cDNA having formed can be subjected to immediate PCR amplification. As described above, in addition to the ds-cDNA from various RNA trans-splicing products, however, the analytical batch of cell extract also includes much higher concentration of ds-cDNA from the probe RNA remaining unspliced. This latter ds-cDNA fraction would therefore be amplified with preference in a subsequent PCR, so that the ds-cDNAs from the RNA trans-splicing products would not provide PCR products detectable by gel analysis. Consequently, the ds-cDNA from the non-spliced probe RNA must be eliminated (cleaved) specifically, e.g. via restriction digestion, prior to PCR amplification. In a specific example, the analytical batch is added with the rare cutter SwaI under suitable conditions, which specifically cleaves the ds-cDNA from the non-spliced probe RNA in its outron portion in the 8-mer recognition sequence ATTT/AAAT (see FIGS. 17I, 17J), so that subsequent PCR does not furnish amplification anymore (see FIG. 17K). However, the ds-cDNA from the trans-spliced RNA, which very likely does not include said rare cutter site (see structure thereof: "no ATTTAAAT", see e.g. FIG. 17E), very likely will not be cleaved by the enzymatic treatment, remaining intact (see FIG. 17F), and subsequently can be PCR-amplified with two specific primers and detected (see FIG. 17G).

As an alternative to the above method, initial limited amplification of the ds-cDNA according to the protocol below (about 5 to 15 PCR cycles), followed by complete digestion e.g. with SwaI, and performing another complete PCR (30 to 35 PCR cycles) using the same or (better) other suitable primers is also possible.

After completed incubation with the restriction enzyme, a multi-cycle PCR (about 35 times) is performed under suitable conditions.

Regarding the batches including a probe RNA with a 5' trans-splice site, the two primers used are as follows: 1) A first primer which binds in the exon portion of the probe RNA and is identical to the primer for the synthesis of the second strand of the ds-cDNA (see example of arbitrary case: 5'-AGAA-GAACGGAAGAACAA-3', SEQ ID NO:25, see FIGS. 17D, 17K), or a primer which binds downstream of said ds-cDNA primer to the probe RNA exon. If intending to perform a so-called nested PCR (not illustrated in FIGS. 17A-17K), the PCR primer of the second PCR correspondingly must bind down-stream of the primer of the first PCR in the exon of the probe RNA. 2) The second primer is analogous to the terminal (5') sequence of the 18-21 N-nucleotides of that primer which the distal oligo-T portion and is used in the ss-cDNA synthesis (see FIG. 17K, example: 5'-AACCTTCCAACCGGC-CAA-3', SEQ ID NO:27). If an approximately 40-mer sequence instead of an 18 to 21-mer sequence upstream of the distal oligo-T portion has been used in the ss-cDNA synthesis, a nested PCR can be performed, wherein the 18 to 21-mer primer of the first PCR corresponds to the 5'-terminal sequence, and the 18 to 21-mer primer of the second PCR corresponds to the 3'-terminal sequence of the above-mentioned 40-mer sequence.

Regarding the batches including a probe RNA with a 3' trans-splice site, the primers used are as follows: 1) A first primer which is used in the $2^{nd}$ strand synthesis of the ds-cDNA (shortened cap primer) (see FIG. 18I, example: 5'-GGTTGGAAGGTTGGAAG-3', SEQ ID NO:41). When using a cap primer with a corresponding overhang sequence of 36 to 40 nucleotides, a so-called nested PCR can be performed subsequently, wherein the 18 to 21-mer primer of the first nested PCR pairs to the 5'-terminal portion of the 36 to 40-mer sequence, and the 18 to 21-mer primer of the second nested PCR pairs to the 3'-terminal portion of said sequence of 36 to 40 nucleotides. 2) The second PCR primer is analogous to a known sequence of 18 to 24-mer in the exonic portion of the probe RNA or of the DNA encoding said RNA (see FIG. 18I, example: 5'-CTTGTTCTTCCGTTCTTCT-3', SEQ ID NO:46). If a nested PCR is to be performed, the counterprimer of the second nested PCR is a 18 to 21-mer primer likewise analogous to a corresponding exonic sequence of the probe RNA, but pairing downstream of the primer of the first nested PCR to the exon.

The different PCR DNA products formed in the cDNA PCR, which products derive from corresponding, different cellular RNAs trans-spliced to the RNA probe, are subsequently selected (cloned) at first, using suitable procedures. In the simplest case, selection of the different PCR products can be effected by cutting out the separate PCR DNA fragments from the analytical gel; more favorable, however, is cloning of all resulting PCR products into suitable plasmids and subsequent sequencing of the PCR DNA cloned in the PCR from the trans-spliced product. The cloned or selected cDNA PCR products are then sequenced with one of the two primers from the above PCR according to standardized procedures (see FIG. 17H, FIG. 18J).

In addition to a known sequence from the exonic portion of the probe RNA, the sequenced PCR product also includes the trans-spliced exonic portion from the unknown cellular target RNA.

In that case where a 3' splice site on a cellular target RNA interacts with a 5' splice site of the probe RNA, the unknown portion from the target RNA is situated in the far sequenced section of the PCR product, beginning with the exon start of the 3' splice site (unknown sequence) and ending after 10 to 1000 nucleotides (FIG. 17H) with the sequence $A_{15}$ and the reverse sequence of the at least 18-mer long appendix to the $T_{15}$ primer in the first-strand cDNA synthesis (FIGS. 17E, 17F). In that case where a 5' splice site on a cellular target RNA interacts with a 3' splice site of the probe RNA, the unknown portion from the target RNA is situated in the anterior sequenced section of the PCR product, beginning after the sequence of the terminal cap primer. Following 10-1000 nucleotides from the unknown cellular RNA, there is the 3-base sequence from the exon portion of the 5' splice site of this target RNA (e.g. the sequence GAG, see FIGS. 18A-18M), followed by the exonic sequence of the probe RNA up to the binding site of the primer from the previous cDNA PCR.

Once the sequences of the exonic portions of the cellular RNAs trans-spliced to the RNA probe have been determined (cf., FIG. 15A, lower part), the first, more complex part of the detection of cellular natural RNA products of trans-splicing is completed. The second part involves a final test to see whether the corresponding per se trans-spliceable cellular RNAs interact in vivo in the cell, possibly resulting in RNA products of trans-splicing (hybrid RNAs) (see FIG. 15B or 19A).

Figure 15B:
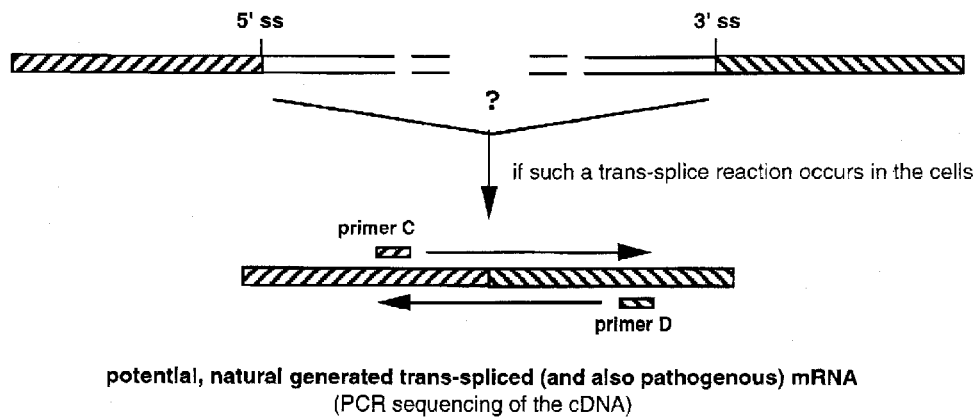

More specifically, the only thing thus remaining is to investigate whether the 5' splice sites and 3' splice sites situated on various cellular pre-mRNA species and capable of transsplicing in principle would also interact in vivo in the living cell so as to allow formation of a trans-spliced hybrid mRNA which therefore is derived from 2 gene loci and possibly encodes pathogenic/malignant proteins (FIGS. 15B, 19A). Indeed, this happens in a cDNA PCR on the total RNA in cells, wherein both PCR primers in their 18 to 24-mer sequence are analogous on the one hand (=primer C in FIG. 15B) to an arbitrary, previously sequenced exonic sequence A (see FIG. 19A) of the potential trans-splicing partner component A having a potent 5' splice site and, on the other hand (=primer D in FIG. 15B), to an arbitrary, previously sequenced (see FIG. 19A) exonic sequence B of the potential trans-splicing partner component B having a potent 3' splice site. If the above two PCR primers lead to formation of a PCR product, it must be assumed that this PCR product derives from a correspondingly trans-spliced cellular hybrid mRNA. Cellular trans-splicing has to be confirmed appropriately by final sequencing of the PCR product (FIG. 19E). If the probe RNA with the 5' splice site identifies a number X of different potent 5' trans-splice sites or pertaining RNAs as corresponding cDNA PCR products, and the probe RNA with the 3' splice site identifies a number Y of different potent 3' trans-splice sites or pertaining RNAs as corresponding cDNA PCR products, all possible combinations of potent trans-splice sites on the different cellular premRNAs must be accounted for in the final test procedure; therefore, X×Y different PCR reactions with corresponding, different primer combinations must be carried out.

In the case of detected natural cellular RNA trans-spliced products, the protein sequence derived therefrom must be determined. Tests using immunoblots then can be performed to see whether the hybrid protein hypothetically produced from the trans-spliced product will actually be expressed in vivo and to what extent. In a last step, tests as to possible pathogenicity of the hybrid protein must be performed. In the simplest case, this is done by incorporating e.g. a ds-cDNA encoding a completely trans-spliced hybrid mRNA in healthy cells. From this ds-cDNA the cell will form the corresponding mRNA with the pertaining hybrid protein which—if malignant—then possibly induces pathological processes or tumor transformation in the cell.

In the third case of application described, the invention therefore relates to an incorporated trans-spliceable RNA likewise consisting of merely one exon and one outron and serving as RNA probe to identify cellular RNAs initially trans-spliceable per se. The invention also relates to the specific detection method for the sequence determination of trans-spliceable cellular RNAs and of cellular trans-spliced hybrid mRNAs formed therefrom, as described in the section above.

In the third case of application, the invention also relates to a kit for the identification of trans-splice sites on cellular RNAs, which can be used to detect possibly trans-spliced, malignant hybrid RNAs, said kit comprising the inventive probe RNAs, as well as additional primers for specific cDNA synthesis and PCR amplification, and a protocol of instructions.

The probe RNA is a pre-mRNA 150 to 300 bases in length (if encoding a protein, some hundred bases), likewise including a very potent 5' or 3' splice site. In a subcase A, the probe RNA also has an oligo-U region in the outron portion thereof, which region is absent in subcase B. In the respective outron region, the probe RNA or the coding DNA additionally has a 8 to 12-mer recognition nucleotide sequence for a rare cutter, e.g. the sequence AUUU/AAAU on the RNA level, which, in the ds-cDNA produced from the RNA, is cleaved by a corresponding restriction enzyme, here: SwaI, in a following step during analysis. The DNA that encodes that RNA and is introduced into the living cells to be analyzed also includes a promoter with enhancer elements, a polyadenylation signal, and a replication origin.

Consequently, the DNA which encodes a probe RNA with a 5' trans-splice site has the following structure (from 5' to 3'):

a) At the beginning, there is a strong replication origin (e.g. from SV40), followed by b) a strong promoter with enhancer (e.g. from SV40) (cf., e.g. FIGS. 7A, 8A).

c) In the following sequence, but at least 10 nucleotides upstream of the 5' splice site, is an A/G-rich region or another specific region serving as splice enhancer region (see FIG. 9B, therein as RNA sequence).

d) 40 to 120 nucleotides downstream of the promoter end (begin of the RNA encoded therefrom), at the exon/outron border, is the 5' splice site with the sequence (A/G)-A-G-G-T-A-(A/G)-G-T (see FIG. 17A, therein as RNA sequence), or with the preferred sequence: A-A-G-G-T-A-A-G-T.

e) 10 to 30 nucleotides downstream of the above sequence, in type A of this DNA, is a sequence of 15 to 18 thymidines (T) (see FIG. 17A); in type B of this DNA, this sequence is absent.

f) 10 to 30 nucleotides downstream of the poly-T sequence (type A DNA) or 20 to 60 nucleotides downstream of the 5' splice site (type B DNA) is an 8 to 12-mer nucleotide sequence for the recognition of a rare cutter (e.g. the sequence ATTT/AAAT for the recognition of SwaI, see FIG. 17A, therein as RNA).

g) 10 to 50 nucleotides downstream of this region is the polyadenylation recognition site A-A-T-A-A-A, followed by a downstream G/T-rich region ($2^{nd}$ polyadenylation site, e.g. from SV40) (FIGS. 7A, 8A).

Consequently, the DNA which encodes a probe RNA with a 3' trans-splice site has the following structure (from 5' to 3'):

a) At the beginning, there is a strong replication origin (e.g. from SV40), followed by b) a strong promoter with enhancer (e.g. from SV40) (cf., e.g. FIGS. 7A, 8A).

c) 20 to 60 nucleotides downstream of the promoter region (begin of RNA, with cap Site) in type A of this DNA is a sequence of 15 to 18 thymidines (T) (see FIG. 18A); in type B of this DNA this sequence is absent.

d) 10 to 40 nucleotides downstream of the poly-T sequence (type A DNA) or 30 to 100 nucleotides downstream of the promoter end (type B DNA) is an 8 to 12-mer nucleotide sequence for the recognition of a rare cutter (e.g. the sequence ATTT/AAAT for the recognition of SwaI) (see FIG. 18A, therein as RNA sequence).

e) 10 to 30 nucleotides downstream of this restriction enzyme recognition sequence is the branch A region of the 3' splice site with the sequence T-(A/G)-(C/T)-T(A/G)-A-(C/T)-(A/G) (FIG. 18A).

f) 10 to 30 nucleotides downstream of this branch A sequence is a polypyrimidine base sequence of 15 to 18-mer T/C, followed by the splice site dinucleotide AG towards the end of the outron (FIG. 18A).

g) In the following sequence, from the beginning of the exon on, but at least 10 nucleotides downstream of the 3' splice site and at least 10 nucleotides upstream of the polyadenylation site, is an A/G-rich region or another specific region serving as splice enhancer region (see FIG. 10B, therein as RNA sequence).

h) The following sequence starting from the beginning of the exon, being a cDNA in addition, can encode a short, in situ easily detectable, incomplete protein, the sequence of which in the exon beginning e.g. with amino acid 2, and which is completed by a termination signal (TAG etc.), which exon, however, does not include the translation start codon ATG.

i) 80 to 140 nucleotides or, if an incomplete protein is encoded, some hundred nucleotides downstream of the splice site dinucleotide AG is the primary polyadenylation site A-A-T-A-A-A, followed by a downstream G/T-rich region (second polyadenylation site, e.g. from SV40) (cf., e.g. FIGS. 7A, 8A).

With reference to an example, the invention will be explained in more detail with respect to case of application 2, without limiting the invention thereto.

EXAMPLE

Trans-splicing between an artificially created, incomplete RNA, which encodes the HSV-TK protein, and an alpha-fetoprotein RNA (AFP-RNA) from tumor cells for the selective destruction of these tumor cells:

Initially, the RNA encoding the HSV-TK protein is generated in the cells by incorporating an appropriate DNA in all cells (tumor cells and normal cells), which transcribes said RNA. To achieve strong transcription, this DNA likewise includes a strong promoter with appropriate enhancer regions, e.g. from SV40 (see FIG. 11A). To generate a pre-mRNA stable at the 3' end thereof, this DNA also includes a strong polyadenylation recognition site (e.g. likewise from SV40) with an AATAAA region upstream and a poly-GT region downstream of the polyadenylation cleavage site (see FIG. 11A).

In its essential far portion this DNA also includes the complete DNA sequence encoding the cell death protein from amino acid 2 on. Said DNA sequence is obtained via a cDNA sequence derived from the mRNA (see FIG. 11A). In the case of the HSV-TK DNA construct, this is the coding nucleotide sequence for the amino acid 2 (=Ala) up to the last amino acid 376 (=Val), which is followed by the termination signal UAG or TAG (see FIG. 13A).

Upstream of the region encoding the HSV-TK protein from amino acid 2 on, this DNA has a region encoding a peptide stretch (protease linker) which is cleaved by specific cellular proteases invariably present. Depending on the type of protease, this sequence has a length of up to 15 amino acids, i.e., is therefore encoded by up to 45 nucleotides on the DNA (see FIG. 13A).

Upstream of this protease linker region, immediately at the exon border of the 3' splice site, is an optional reading frame linker of 1 or 2 nucleotides to compensate a frame shift with respect to the translated nucleotide sequence from the trans-spliced coding exon 1 of the tumor-specific RNA. When trans-splicing to the exon 1 of the AFP, as in this exemplary case, a correction by 2 nucleotides by means of 2 additional bases (here: CU or CT is selected) is necessary (see FIG. 13A). In the case of trans-splicing, the trans-spliced RNA in this particular case has the sequence GCU (coding for Ala) in the splice junction thereof (see FIG. 13B), so that frame shifting by a "surplus" single nucleotide (here: G) from exon 1 of the AFP-RNA is compensated.

Upstream of the reading frame linker is the outron region which is terminated by the 3' splice site. Again, this 3' splice site should have high splicing competence. This implies the presence of a marked polypyrimidine base (U/C or T/C) stretch immediately upstream of the splice site dinucleotide AG and, about 10 to 30 nucleotides upstream thereof, of a strong branch A region (not depicted in FIG. 13A, cf., FIG. 10B).

A trans-splicing reaction from the singular, artificial 3' splice site on the HSV-TK pre-mRNA to the 5' splice site of exon 1 of the AFP pre-mRNA in a specific and selective fashion is achieved in that this HSV-TK pre-mRNA—because of the demanded substrate specificity—in the outron region upstream of the branch A region has a sequence of at least 18 bases which undergoes specific pairing to the AFP pre-mRNA via antisense structures. In this way, stable binding between the two RNA molecules is furnished, thereby increasing the trans-splicing efficiency by several powers of ten. In addition, such RNA-RNA hybridization should be such that the 3' splice site following exon 1 is blocked in the poly-U/C region and in the AG region (situated at the border to exon 2) on the AFP pre-mRNA (see FIG. 13A). In this way, the trans-splicing efficiency is further increased because competing cis-splicing reaction between exon 1 and exon 2 of the AFP RNA is no longer possible.

Ultimately, trans-splicing between exon 1 of the AFP RNA of the tumor cells and the exon portion of the incomplete, artificially generated cell death RNA (=HSV-TK RNA) produces an mRNA bearing an AUG start codon in the appropriate, correct reading frame for amino acid 2 (=Ala) of the HSV-TK RNA. In this particular exemplary case, the hybrid protein produced upon reading of the trans-spliced RNA (see FIG. 13B) ultimately includes the amino acids from Met 1 to Ile 28 from the AFP RNA, followed by 3 nucleotides (GCU) in the splice junction ultimately providing for reading frame compensation, and followed by a region of up to 15 amino acids, which bears a specific protease recognition region. This region is followed by the actual HSV-TK protein region (from amino acid 2=Ala to amino acid 376=Val). The final hybrid protein is then cleaved in the specific protease recognition region by a cellular protease (see FIG. 13C) to remove foreign protein portions (from the AFP portion) which might interfere with the HSV-TK enzyme function. Thereafter, the HSV-TK enzyme is present in the cancer cells only, but not in healthy cells. (It is only in cancer cells where corresponding trans- splicing to the AFP RNA exclusively present therein is possible, which trans-splicing ultimately provides said protein.) In the cancer cells this enzyme then converts the supplied medicament ganciclovir into a phosphorylated derivative, thereby ultimately achieving termination of any DNA replication of the cancer cell which is destroyed in this way.

---

What is claimed is:

1. A modified, shortened cell death pre-mRNA-encoding DNA of a Herpes Simplex Virus-Thymidine Kinase (HSV-TK) protein comprising a nucleotide sequence including a replication origin, an RNA polymerase-II promoter, a signal sequence at a 3' end for pre-mRNA polyadenylation, an anterior 5' outron, and an exon having a nucleotide sequence encoding from a second amino acid Ala (alanine) and up to a last amino acid Val (valine) at position 376 of the HSV-TK protein.

2. The modified, shortened cell death pre-mRNA-encoding DNA according to claim 1, wherein a 5' end of the exon has a frame shift sequence of 1 or 2 nucleotides.

3. The modified, shortened cell death pre-mRNA-encoding DNA according to claim 1, further comprising an exon downstream of a frame shift nucleotide sequence and upstream of the nucleotide sequence encoding from a second amino acid Ala (alanine) and up to a last amino acid Val (valine) at position 376 of the HSV-TK protein, this exon including a protease recognition region encoding a peptide sequence which can be cleaved by naturally-occurring cellular proteases.

4. The modified, shortened cell death pre-mRNA-encoding DNA according to claim 1, further comprising an exon having an exonic splice enhancer (ESE) sequence in a region of a protease recognition region or in a region of the nucleotide encoding from a second amino acid Ala (alanine) and up to a last amino acid Val (valine) at position 376 of the HSV-TK protein, this exon having no additional or other amino acids being coded for by the ESE sequence.

5. The modified, shortened cell death pre-mRNA-encoding DNA according to claim 1, wherein the outron has a 3' splice site comprising a branch A site, a polypyrimidine base stretch, and an AG dinucleotide at a border to the exon.

6. The modified, shortened cell death pre-mRNA-encoding DNA according to claim 5, wherein the branch A site has an 8-mer sequence U-A/G-C/U-U-A/G-A-C/U-A/G, and the polypyrimidine base stretch has a 15-18-mer (U/C) sequence.

7. The modified, shortened cell death pre-mRNA-encoding DNA according to claim 1, further comprising an outron upstream of a 3' splice site thereof, the outron including a sequence of at least 18 nucleotides in length, the nucleotides undergoing specific pairing with a tumor pre-mRNA.

8. The modified, shortened cell death pre-mRNA-encoding DNA according to claim 1, further comprising a sequence in a 5' outron which pairs to a specific tumor cell pre-mRNA in its polypyrimidine base sequence of a 3' splice site upstream of a second coding exon of the specific tumor cell pre-mRNA.

9. The modified, shortened cell death pre-mRNA-encoding DNA according to claim 1, further comprising an outron having a translation start AUG which is not a reading frame of an exon for the nucleotide sequence encoding from a second amino acid Ala (alanine) and up to a last amino acid Val (valine) at position 376 of the HSV-TK protein, the translation start AUG initiating a short nonsense protein.

10. The modified, shortened cell death pre-mRNA-encoding DNA according to claim 7, wherein the tumor pre-mRNA encodes for alpha-fetoprotein (AFP).

* * * * *